(12) United States Patent
Koussa et al.

(10) Patent No.: US 11,198,900 B2
(45) Date of Patent: Dec. 14, 2021

(54) NUCLEIC ACID-BASED LINKERS FOR DETECTING AND MEASURING INTERACTIONS

(71) Applicants: Children's Medical Center Corporation, Boston, MA (US); President and Fellows of Harvard College, Cambridge, MA (US)

(72) Inventors: Mounir Ahmad Koussa, Somerville, MA (US); Kenneth Anders Halvorsen, Glenmont, NY (US); Andrew Ward, Boston, MA (US); Wesley Philip Wong, Cambridge, MA (US)

(73) Assignees: Children's Medical Center Corporation, Boston, MA (US); President and Fellows of Harvard College, Cambridge, MA (US)

( * ) Notice: Subject to any disclaimer, the term of this patent is extended or adjusted under 35 U.S.C. 154(b) by 130 days.

(21) Appl. No.: 15/533,473

(22) PCT Filed: Nov. 16, 2015

(86) PCT No.: PCT/US2015/060952
§ 371 (c)(1),
(2) Date: Jun. 6, 2017

(87) PCT Pub. No.: WO2016/089588
PCT Pub. Date: Jun. 9, 2016

(65) Prior Publication Data
US 2017/0369935 A1 Dec. 28, 2017

Related U.S. Application Data

(60) Provisional application No. 62/088,592, filed on Dec. 6, 2014.

(51) Int. Cl.
*C12Q 1/68* (2018.01)
*C12Q 1/6818* (2018.01)
(Continued)

(52) U.S. Cl.
CPC ............ *C12Q 1/6818* (2013.01); *C12P 19/34* (2013.01); *G01N 27/447* (2013.01); *C12Q 2563/131* (2013.01); *C12Q 2565/125* (2013.01)

(58) Field of Classification Search
USPC .................. 435/6.1, 6.11, 91.1; 436/94, 501; 204/450, 456
See application file for complete search history.

(56) References Cited

U.S. PATENT DOCUMENTS 5,571,677 A 11/1996 Gryaznov
5,635,352 A 6/1997 Urdea et al.
(Continued)

FOREIGN PATENT DOCUMENTS

JP H06-508753 A 10/1994
JP 2000-312589 A 8/2000
(Continued)

OTHER PUBLICATIONS

International Search Report and Written Opinion for Application No. PCT/US2015/060952 dated Feb. 4, 2016.
(Continued)

*Primary Examiner* — Frank W Lu
(74) *Attorney, Agent, or Firm* — Wolf, Greenfield & Sacks, P.C.

(57) ABSTRACT

The invention provides compositions comprising nucleic acid complexes for use in monitoring binding interactions and in measuring association and/or dissociation kinetics, detecting analytes including low concentration analytes, and screening library members. In some instances, the nucleic
(Continued)

acid complexes are double-stranded nicked nucleic acids comprising a scaffold nucleic acid hybridized to one or more oligonucleotides. In some instances, a first, a second, a third, and optionally a fourth oligonucleotide are linked to moieties that are known to interact with each other or which are suspected of interacting with each other or of interacting with a common moiety such as an analyte. Changes in topology of the complex are used to determine the binding interactions of the various binding partners.

11 Claims, 20 Drawing Sheets

Specification includes a Sequence Listing.

(51) Int. Cl.
  *C12P 19/34* (2006.01)
  *G01N 27/447* (2006.01)

(56) References Cited

U.S. PATENT DOCUMENTS

| | | | |
|---|---|---|---|
| 5,888,731 | A | 5/1999 | Yager et al. |
| 5,902,724 | A | 5/1999 | Lane et al. |
| 6,143,504 | A | 11/2000 | Das et al. |
| 6,232,066 | B1 | 5/2001 | Felder et al. |
| 6,251,660 | B1 | 6/2001 | Muir et al. |
| 6,569,306 | B1 | 5/2003 | Read et al. |
| 6,770,698 | B1 | 8/2004 | Chu et al. |
| 8,491,454 | B2 | 7/2013 | Wong et al. |
| 8,795,143 | B2 | 8/2014 | Wong et al. |
| 9,255,905 | B1 | 2/2016 | Mellors et al. |
| 9,914,958 | B2 | 3/2018 | Wong et al. |
| 9,994,839 | B2 | 6/2018 | Lo et al. |
| 10,919,037 | B2 | 2/2021 | Wong et al. |
| 2002/0177144 | A1 | 11/2002 | Remacle et al. |
| 2003/0143549 | A1 | 7/2003 | Yang et al. |
| 2006/0257958 | A1 | 11/2006 | Bruno |
| 2007/0026423 | A1 | 2/2007 | Koehler et al. |
| 2007/0037152 | A1 | 2/2007 | Drmanac |
| 2007/0117109 | A1 | 5/2007 | Rothemund |
| 2007/0154899 | A1 | 7/2007 | Coull et al. |
| 2007/0155017 | A1 | 7/2007 | Wyatt |
| 2008/0038725 | A1 | 2/2008 | Luo et al. |
| 2008/0131870 | A1 | 6/2008 | Allawi et al. |
| 2008/0312103 | A1 | 12/2008 | Nemoto et al. |
| 2009/0087838 | A1 | 4/2009 | Reif et al. |
| 2009/0286694 | A1 | 11/2009 | Zainiev et al. |
| 2010/0015608 | A1 | 1/2010 | Kolpashchikov |
| 2010/0035247 | A1 | 2/2010 | Burton |
| 2010/0137120 | A1 | 6/2010 | Wong |
| 2010/0206730 | A1 | 8/2010 | Hunkapiller et al. |
| 2010/0216658 | A1 | 8/2010 | Chaput et al. |
| 2011/0086774 | A1 | 4/2011 | Dunaway |
| 2011/0268654 | A1 | 11/2011 | Hilderbrand et al. |
| 2012/0058008 | A1 | 3/2012 | Corbett et al. |
| 2013/0004523 | A1 | 1/2013 | Zubarev et al. |
| 2013/0130884 | A1 | 5/2013 | Wong et al. |
| 2013/0196341 | A1 | 8/2013 | Neely et al. |
| 2013/0225429 | A1 | 8/2013 | Curry |
| 2013/0310260 | A1 | 11/2013 | Kim et al. |
| 2013/0344508 | A1 | 12/2013 | Schwartz et al. |
| 2014/0255939 | A1 | 9/2014 | Wong et al. |
| 2014/0284213 | A1 | 9/2014 | Sabin et al. |
| 2015/0027894 | A1 | 1/2015 | Puleo et al. |
| 2015/0093836 | A1 | 4/2015 | Suzuki et al. |
| 2015/0099650 | A1 | 4/2015 | Sood et al. |
| 2015/0361422 | A1 | 12/2015 | Sampson et al. |
| 2018/0135043 | A1 | 5/2018 | Wong et al. |
| 2018/0223344 | A1 | 8/2018 | Chandrasekaran et al. |
| 2018/0291434 | A1 | 10/2018 | Wong et al. |
| 2019/0048409 | A1 | 2/2019 | Wong et al. |
| 2019/0064056 | A1 | 2/2019 | Yang et al. |
| 2019/0070604 | A1 | 3/2019 | Wong et al. |
| 2020/0116712 | A1 | 4/2020 | Hansen et al. |
| 2020/0340033 | A1 | 10/2020 | Wong et al. |

FOREIGN PATENT DOCUMENTS

| | | |
|---|---|---|
| JP | 2003-219897 A | 8/2003 |
| JP | 2005-536234 A | 12/2005 |
| JP | 2008-259453 A | 10/2008 |
| JP | 2009-521230 A | 6/2009 |
| WO | WO 93/01313 A1 | 1/1993 |
| WO | WO 98/18961 A1 | 5/1998 |
| WO | WO 00/40751 A2 | 7/2000 |
| WO | WO 2004/016767 A2 | 2/2004 |
| WO | WO 2007/076128 A2 | 7/2007 |
| WO | WO 2011/005221 A1 | 1/2011 |
| WO | WO 2011/153211 A1 | 12/2011 |
| WO | WO 2012/058638 A2 | 5/2012 |
| WO | WO 2013/010023 A2 | 1/2013 |
| WO | WO 2013/067489 A1 | 5/2013 |
| WO | WO 2014/011800 A1 | 1/2014 |
| WO | WO 2015/006626 A1 | 1/2015 |
| WO | WO 2015/040009 A1 | 3/2015 |
| WO | WO 2015/164602 A2 | 10/2015 |
| WO | WO 2016/089588 A1 | 6/2016 |
| WO | WO 2016/196824 A1 | 12/2016 |
| WO | WO 2017/003950 A2 | 1/2017 |
| WO | WO 2017/139409 A1 | 8/2017 |
| WO | WO 2017/147398 A1 | 8/2017 |
| WO | WO 2018/106721 A1 | 6/2018 |
| WO | WO 2019/100080 A1 | 5/2019 |

OTHER PUBLICATIONS

International Preliminary Report on Patentability for Application No. PCT/US2015/060952 dated Jun. 15, 2017.
[No Author Listed], Wikipedia Entry, "XhoI." May 14, 2014. Retrieved from the internet. Https://en.wikipedia.org/w/index.php?title=XhoI&oldid=608536958>. Retrieved on Oct. 18, 2016.
Aaij et al., The gel electrophoresis of DNA. Biochim Biophys Acta. May 10, 1972;269(2):192-200.
Baumann et al., Ionic effects on the elasticity of single DNA molecules. Proc Natl Acad Sci U S A. Jun. 10, 1997;94(12):6185-90.
Bellot et al., Recovery of intact DNA nanostructures after agarose gel-based separation. Nat Methods. Mar. 2011;8(3): 192-4. doi: 10.1038/nmeth0311-192.
Bishop et al., Electrophoretic separation of viral nucleic acids on polyacrylamide gels. J Mol Biol. Jun. 28, 1967;26(3):373-87.
Bustamante et al., Entropic elasticity of lambda-phage DNA. Science. Sep. 9, 1994;265(5178):1599-600.
Bustamante et al., Ten years of tension: single-molecule DNA mechanics. Nature. Jan. 23, 2003;421(6921):423-7.
Chandrasekaran et al., Label-free detection of specific nucleic acid sequences using dna nanoswitches. The RNA Institute, University at Albany, State University of New York.
Chandrasekaran et al., Programmable DNA nanoswitches for detection of nucleic acid sequences. ACS Sens., 2016, 1 (2), pp. 120-123.
Cheng et al., Early pregnancy factor in cervical mucus of pregnant women. Am J Reprod Immunol. Feb. 2004;51(2):102-5.
Chilkoti et al., Molecular origins of the slow streptavidin-biotin dissociation kinetics. J Am Chem Soc. 1995; 117(43):10622-8.
Chivers et al., A streptavidin variant with slower biotin dissociation and increased mechanostability. Nat Methods. May 2010;7(5):391-3. doi: 10.1038/nmeth.1450. Epub Apr. 11, 2010.
Cho et al., A genomic-scale view of the cAMP response element-enhancer decoy: a tumor target-based genetic tool. Proc Natl Acad Sci USA. Nov. 26, 2002;99(24):15626-31. Epub Nov. 18, 2002.
Conde et al., Implantable hydrogel embedded dark-gold nanoswitch as a theranostic probe to sense and overcome cancer multidrug resistance. Proc Natl Acad Sci USA. Mar. 17, 2015;112(11):E1278-87. doi: 10.1073/pnas.1421229112. Epub Mar. 2, 2015.
Deniz et al., Single-molecule biophysics: at the interface of biology, physics and chemistry. J R Soc Interface. Jan. 6, 2008;5(18):15-45.

(56) References Cited

OTHER PUBLICATIONS

Doshi et al., In vitro nanobody discovery for integral membrane protein targets. Sci Rep. Oct. 24, 2014;4:6760. doi: 10.1038/srep06760.

Douglas et al., A logic-gated nanorobot for targeted transport of molecular payloads. Science. Feb. 17, 2012;335(6070):831-4. doi: 10.1126/science.1214081.

Douglas et al., Self-assembly of DNA into nanoscale three-dimensional shapes. Nature. May 21, 2009;459(7245):414-8. doi: 10.1038/nature08016.

Evans et al., Dynamic strength of molecular adhesion bonds. Biophys J. Apr. 1997;72(4):1541-55.

Evans et al., Forces and bond dynamics in cell adhesion. Science. May 25, 2007;316(5828):1148-53.

Evans, Probing the relation between force—lifetime—and chemistry in single molecular bonds. Annu Rev Biophys Biomol Struct. 2001;30:105-28.

Fazio et al., DNA curtains and nanoscale curtain rods: high-throughput tools for single molecule imaging. Langmuir. Sep. 16, 2008;24(18):10524-31. doi: 10.1021/la801762h. Epub Aug. 7, 2008.

França et al., A review of DNA sequencing techniques. Q Rev Biophys. May 2002;35(2):169-200.

Green, Avidin and streptavidin. Methods Enzymol. 1990;184:51-67.

Greenleaf et al., High-resolution, single-molecule measurements of biomolecular motion. Annu Rev Biophys Biomol Struct. 2007;36:171-90.

Halvorsen et al., Binary DNA nanostructures for data encryption. PLoS One. 2012;7(9):e44212. doi: 10.1371/journal.pone.0044212. Epub Sep. 11, 2012.

Halvorsen et al., Cross-platform comparison of nucleic acid hybridization: toward quantitative reference standards. Anal Biochem. Nov. 15, 2014;465:127-33. doi: 10.1016/j.ab.2014.08.001. Epub Aug. 12, 2014.

Halvorsen et al., Massively parallel single-molecule manipulation using centrifugal force. Biophys J. Jun. 2, 2010;98(11):L53-5.

Halvorsen et al., Nanoengineering a single-molecule mechanical switch using DNA self-assembly. Nanotechnology. Dec. 9, 2011;22(49):494005. doi:10.1088/0957-4484/22/49/494005. Epub Nov. 21, 2011.

Halvorsen, Probing weak single-molecule interactions: Development and demonstration of a new instrument. Boston University, College of Engineering dissertation. 2007: 102 pages.

Hanke et al., Entropy loss in long-distance DNA looping. Biophys J. Jul. 2003;85(1):167-73.

Hansen et al., Nanoswitch-linked immunosorbent assay (NLISA) for fast, sensitive, and specific protein detection. PNAS. Sep. 26, 2017;114(39):10367-10372. Supporting Information, 4 pages.

Hassur et al., UV shadowing—a new and convenient method for the location of ultraviolet-absorbing species in polyacrylamide gels. Anal Biochem. May 1974;59(1):162-4.

Hellman et al., Electrophoretic mobility shift assay (EMSA) for detecting protein-nucleic acid interactions. Nat Protoc. 2007;2(8):1849-61.

Idili et al., Programmable pH-triggered DNA nanoswitches. J Am Chem Soc. Apr. 23, 2014;136(16):5836-9. doi: 10.1021/ja500619w. Epub Apr. 9, 2014. Abstract only.

Jones et al., Nanomaterials. Programmable materials and the nature of the DNA bond. Science. Feb. 20, 2015;347(6224): 1260901. doi: 10.1126/science.1260901.

Jung et al., Binding and dissociation kinetics of wild-type and mutant streptavidins on mixed biotin-containing alkylthiolate monolayers. Langmuir. Nov. 28, 2000;16(24):9421-32.

Khalil et al., Single M13 bacteriophage tethering and stretching. Proc Natl Acad Sci U S A. Mar. 20, 2007;104(12):4892-7. Epub Mar. 13, 2007.

Kim et al., A mechanically stabilized receptor-ligand flex-bond important in the vasculature. Nature. Aug. 19, 2010;466(7309):992-5. doi: 10.1038/nature09295.

Kim et al., Multiplexed single-molecule assay for enzymatic activity on flow-stretched DNA. Nat Methods. May 2007;4(5):397-9. Epub Apr. 15, 2007.

Klumb et al., Energetic roles of hydrogen bonds at the ureido oxygen binding pocket in the streptavidin-biotin complex. Biochemistry. May 26, 1998;37(21):7657-63.

Koch et al., Prospects and limitations of the rosette inhibition test to detect activity of early pregnancy factor in the pig. J Reprod Fertil. May 1985;74(1):29-38.

Koussa et al., DNA nanoswitches: a quantitative platform for gel-based biomolecular interaction analysis. Nat Methods. Feb. 2015;12(2):123-6. doi: 10.1038/nmeth.3209. Epub Dec. 8, 2014.

Koussa et al., Protocol for sortase-mediated construction of DNA-protein hybrids and functional nanostructures. Methods. May 15, 2014;67(2):134-41. doi: 10.1016/j.ymeth.2014.02.020. Epub Feb. 22, 2014.

Kufer et al., Single-molecule cut-and-paste surface assembly. Science. Feb. 1, 2008;319(5863):594-6. doi:10.1126/science.1151424.

Leier et al., Cryptography with DNA binary strands. Biosystems. Jun. 2000;57(1):13-22.

McDonell et al., Analysis of restriction fragments of T7 DNA and determination of molecular weights by electrophoresis in neutral and alkaline gels. J Mol Biol. Feb. 15, 1977;110(1):119-46.

Modi et al., A DNA nanomachine that maps spatial and temporal pH changes inside living cells. Nat Nanotechnol. May 2009;4(5):325-30. doi: 10.1038/nnano.2009.83. Epub Apr. 6, 2009. Abstract only.

Morton et al., Rosette inhibition test: A multicentre investigation of early pregnancy factor in humans. J Reprod Immunol. Sep. 1982;4(5):251-61.

Morton et al., Early pregnancy factor. Semin Reprod Endocrinol. May 1992;10(2):72-82.

Nelson et al., Tethered particle motion as a diagnostic of DNA tether length. J Phys Chem B. Aug. 31, 2006;110(34):17260-7. Abstract only.

Neuman et al., Single-molecule force spectroscopy: optical tweezers, magnetic tweezers and atomic force microscopy. Nat Methods. Jun. 2008;5(6):491-505. doi: 10.1038/nmeth.1218.

Park et al., Dual blockade of cyclic AMP response element—(CRE) and AP-1-directed transcription by CRE-transcription factor decoy oligonucleotide, gene-specific inhibition of tumor growth. J Biol Chem. Jan. 15, 1999;274(3):1573-80.

Pei et al., A DNA nanostructure-based biomolecular probe carrier platform for electrochemical biosensing. Adv Mater. Nov. 9, 2010;22(42):4754-8. doi: 10.1002/adma.201002767.

Quek et al., Mechanically controlled binary conductance switching of a single-molecule junction. Nat Nanotechnol. Apr. 2009;4(4):230-4. doi:10.1038/nnano.2009.10. Epub Mar. 1, 2009.

Rief et al., Sequence-dependent mechanics of single DNA molecules. Nat Struct Biol. Apr. 1999;6(4):346-9.

Ritort, Single-molecule experiments in biological physics: methods and applications. J Phys Condens Matter. Aug. 16, 2006;18(32):R531-83. doi:10.1088/0953-8984/18/32/R01. Epub Jul. 25, 2006.

Rothemund, Folding DNA to create nanoscale shapes and patterns. Nature. Mar. 16, 2006;440(7082):297-302.

Sacca et al., DNA origami: the art of folding DNA. Angew Chem Int Ed Engl. Jan. 2, 2012;51(1):58-66. doi: 10.1002/anie. 201105846. Epub Dec. 7, 2011.

Seeman, DNA in a material world. Nature. Jan. 23, 2003;421(6921):427-31.

Seeman, Nanomaterials based on DNA. Annu Rev Biochem. 2010;79:65-87. doi: 10.1146/annurev-biochem-060308-102244.

Shroff et al., Biocompatible force sensor with optical readout and dimensions of 6 nm3. Nano Lett. Jul. 2005;5(7):1509-14.

Shroff et al., Optical measurement of mechanical forces inside short DNA loops. Biophys J. Mar. 15, 2008;94(6):2179-86. Epub Dec. 7, 2007.

Smith et al., Overstretching B-DNA: the elastic response of individual double-stranded and single-stranded DNA molecules. Science. Feb. 9, 1996;271(5250):795-9.

Strunz et al., Dynamic force spectroscopy of single DNA molecules. Proc Natl Acad Sci U S A. Sep. 28, 1999;96(20): 11277-82.

Svoboda et al., Direct observation of kinesin stepping by optical trapping interferometry. Nature. Oct. 21, 1993;365(6448):721-7.

(56) References Cited

OTHER PUBLICATIONS

Thorne, Electrophoretic separation of polyoma virus DNA from host cell DNA. Virology. Jun. 1966;29(2):234-9.

Thuring et al., A freeze-squeeze method for recovering long DNA from agarose gels. Anal Biochem. May 26, 1975;66(1):213-20.

Wiita et al., Force-dependent chemical kinetics of disulfide bond reduction observed with single-molecule techniques. Proc Natl Acad Sci U S A. May 9, 2006;103(19):7222-7. Epub Apr. 27, 2006.

Williams et al., Entropy and heat capacity of DNA melting from temperature dependence of single molecule stretching. Biophys J. Apr. 2001;80(4):1932-9.

Winfree et al., Design and self-assembly of two-dimensional DNA crystals. Nature. Aug. 6, 1998;394(6693):539-44.

Wong et al., The effect of integration time on fluctuation measurements: calibrating an optical trap in the presence of motion blur. Opt Express. Dec. 11, 2006;14(25):12517-31.

Zadeh et al., NUPACK: Analysis and design of nucleic acid systems. J Comput Chem. Jan. 15, 2011;32(1):170-3. doi: 10.1002/jcc.21596.

Zhang et al., Mechanoenzymatic cleavage of the ultralarge vascular protein, von Willebrand Factor. Science. Jun. 5, 2009;324(5932):1330-4.

Zheng et al., From molecular to macroscopic via the rational design of a self-assembled 3D DNA crystal. Nature. Sep. 3, 2009;461(7260):74-7. doi: 10.1038/nature08274.

Kleiner et al., Small-molecule discovery from DNA-encoded chemical libraries. Chem Soc Rev. Dec. 2011;40(12):5707-17. doi: 10.1039/c1cs15076f. Epub Jun. 14, 2011.

Yang et al., Multiplexed single-molecule force spectroscopy using a centrifuge. Nat Commun. Mar. 17, 2016;7:11026(1-7). doi: 10.1038/ncomms11026. PubMed PMID: 26984516; PubMed Central PMCID: PMC4800429.

Fang et al., Tuning surface states to achieve the modulated fluorescence of carbon dots for probing the activity of alkaline phosphatase and immunoassay of alpha-fetoprotein. Sensors and Actuators B: Chemical. 2018;257:620-628.

Hopwood et al., Integrated microfluidic system for rapid forensic DNA analysis: sample collection to DNA profile. Anal Chem. Aug. 15, 2010;82(16):6991-9. doi: 10.1021/ac101355r.

Lubken et al., Multiplexed Continuous Biosensing by Single-Molecule Encoded Nanoswitches. Nano Lett. Apr. 8, 2020;20(4):2296-2302. doi: 10.1021/acs.nanolett.9b04561. Epub Mar. 12, 2020.

Papadakis et al., Acoustic characterization of nanoswitch structures: application to the DNA Holliday Junction. Nano Lett. Dec. 8, 2010;10(12):5093-7. doi: 10.1021/nl103491v. Epub Nov. 1, 2010.

Ping, High Performing assay using antibody-conjugated DNA nanoswitches detects proteins. MRS Bulletin. 2017;42:780. 1 page.

Porchetta et al., Programmable Nucleic Acid Nanoswitches for the Rapid, Single-Step Detection of Antibodies in Bodily Fluids. J Am Chem Soc. Jan. 24, 2018;140(3):947-953. doi: 10.1021/jacs.7b09347. Epub Jan. 9, 2018.

Yang et al., An integratable microfluidic cartridge for forensic swab samples lysis. Forensic Sci Int Genet. Jan. 2014;8(1):147-58. doi: 10.1016/j.fsigen.2013.08.012. Epub Sep. 8, 2013.

U.S. Appl. No. 14/356,282, filed May 5, 2014, Published, 2014-0255939.

U.S. Appl. No. 15/578,962, filed Dec. 1, 2017, Pending.

PCT/US2015/060952, Feb. 4, 2016, International Search Report and Written Opinion.

PCT/US2015/060952, Jun. 15, 2017, International Preliminary Report on Patentability.

PCT/US2018/062141, Nov. 20, 2018, Published, WO 2019/100080.

FIG. 1A

121 Plain oligos spanning the entire M13 template
001 AACATCCAATAAATCATACAGGCAAGGCAAAGAATTAGCAAAATTAAGCAATAAAGCCTC
002 AGAGCATAAAGCTAAATCGGTTGTACCAAAACATTATGACCCTGTAATACTTTTGCGGG
003 AGAAGCCTTTATTTCAACGCAAGGATAAAAATTTTTAGAACCCTCATATATTTTAAATGC
004 AATGCCTGAGTAATGTGTAGGTAAAGATTCAAAAGGGTGAGAAAGGCCGGAGACAGTCAA
005 ATCACCATCAATATGATATTCAACCGTTCTAGCTGATAAATTAATGCCGGAGAGGGTAGC
006 TATTTTTGAGAGATCTACAAAGGCTATCAGGTCATTGCCTGAGAGTCTGGAGCAAACAAG
007 AGAATCGATGAACGGTAATCGTAAAACTAGCATGTCAATCATATGTACCCCGGTTGATAA
008 TCAGAAAAGCCCCAAAAACAGGAAGATTGTATAAGCAAATATTTAAATTGTAAACGTTAA
009 TATTTTGTTAAAATTCGCATTAAATTTTTGTTAAATCAGCTCATTTTTTAACCAATAGGA
010 ACGCCATCAAAAATAATTCGCGTCTGGCCTTCCTGTAGCCAGCTTTCATCAACATTAAAT
011 GTGAGCGAGTAACAACCCGTCGGATTCTCCGTGGGAACAAACGGCGGATTGACCGTAATG
012 GGATAGGTCACGTTGGTGTAGATGGGCGCATCGTAACCGTGCATCTGCCAGTTTGAGGGG
013 ACGACGACAGTATCGGCCTCAGGAAGATCGCACTCCAGCCAGCTTTCCGGCACCGCTTCT
014 GGTGCCGGAAACCAGGCAAAGCGCCATTCGCCATTCAGGCTGCGCAACTGTTGGGAAGGG
015 CGATCGGTGCGGGCCTCTTCGCTATTACGCCAGCTGGCGAAAGGGGGATGTGCTGCAAGG
016 CGATTAAGTTGGGTAACGCCAGGGTTTTCCCAGTCACGACGTTGTAAAACGACGGCCAGT
017 GCCAAGCTTGCATGCCTGCAGGTCGACTCTAGAGGATCCCCGGGTACCGAGCTCGAATTC
018 GTAATCATGGTCATAGCTGTTTCCTGTGTGAAATTGTTATCCGCTCACAATTCCACACAA
019 CATACGAGCCGGAAGCATAAAGTGTAAAGCCTGGGGTGCCTAATGAGTGAGCTAACTCAC
020 ATTAATTGCGTTGCGCTCACTGCCCGCTTTCCAGTCGGGAAACCTGTCGTGCCAGCTGCA
021 TTAATGAATCGGCCAACGCGCGGGGAGAGGCGGTTTGCGTATTGGGCGCCAGGGTGGTTT
022 TTCTTTTCACCAGTGAGACGGGCAACAGCTGATTGCCCTTCACCGCCTGGCCCTGAGAGA
023 GTGCAGCAAGCGGTCCACGCTGGTTTGCCCCAGCAGGCGAAAATCCTGTTTGATGGTGG
024 TTCCGAAATCGGCAAAATCCCTTATAAATCAAAAGAATAGCCCGAGATAGGGTTGAGTGT
025 TGTTCCAGTTTGGAACAAGAGTCCACTATTAAAGAACGTGGACTCCAACGTCAAAGGGCG
026 AAAAACCGTCTATCAGGGCGATGGCCCACTACGTGAACCATCACCCAAATCAAGTTTTTT
027 GGGGTCGAGGTGCCGTAAAGCACTAAATCGGAACCCTAAAGGGAGCCCCCGATTTAGAGC
028 TTGACGGGGAAAGCCGGCGAACGTGGCGAGAAAGGAAGGGAAGAAAGCGAAAGGAGCGGG
029 CGCTAGGGCGCTGGCAAGTGTAGCGGTCACGCTGCGCGTAACCACCACACCCGCCGCGCT
030 TAATGCGCCGCTACAGGGCGCGTACTATGGTTGCTTTGACGAGCACGTATAACGTGCTTT FIG. 1A (continued)

```
031 CCTCGTTAGAATCAGAGCGGGAGCTAAACAGGAGGCCGATTAAAGGGATTTTAGACAGGA
032 ACGGTACGCCAGAATCCTGAGAAGTGTTTTATAATCAGTGAGGCCACCGAGTAAAAGAG
033 TCTGTCCATCACGCAAATTAACCGTTGTAGCAATACTTCTTTGATTAGTAATAACATCAC
034 TTGCCTGAGTAGAAGAACTCAAACTATCGGCCTTGCTGGTAATATCCAGAACAATATTAC
035 CGCCAGCCATTGCAACAGGAAAAACGCTCATGGAAATACCTACATTTTGACGGCTCAATCG
036 TCTGAAATGGATTATTTACATTGGCAGATTCACCAGTCACACGACCAGTAATAAAAGGGA
037 CATTCTGGCCAACAGAGATAGAACCCTTCTGACCTGAAAGCGTAAGAATACGTGGCACAG
038 ACAATATTTTTGAATGGCTATTAGTCTTTAATGCGCGAACTGATAGCCCTAAAACATCGC
039 CATTAAAAATACCGAACGAACCACCAGCAGAAGATAAAACAGAGGTGAGGCGGTCAGTAT
040 TAACACCGCCTGCAACAGTGCCACGCTGAGAGCCAGCAGCAAATGAAAAATCTAAAGCAT
041 CACCTTGCTGAACCTCAAATATCAAACCCTCAATCAATATCTGGTCAGTTGGCAAATCAA
042 CAGTTGAAAGGAATTGAGGAAGGTTATCTAAAATATCTTTAGGAGCACTAACAACTAATA
043 GATTAGAGCCGTCAATAGATAATACATTTGAGGATTTAGAAGTATTAGACTTTACAAACA
044 ATTCGACAACTCGTATTAAATCCTTTGCCCGAACGTTATTAATTTTAAAAGTTTGAGTAA
045 CATTATCATTTGCGGAACAAAGAAACCACCAGAAGGAGCGGAATTATCATCATATTCCT
046 GATTATCAGATGATGGCAATTCATCAATATAATCCTGATTGTTGGATTATACTTCTGAA
047 TAATGGAAGGGTTAGAACCTACCATATCAAAATTATTTGCACGTAAAACAGAAATAAAGA
048 AATTGCGTAGATTTTCAGGTTTAACGTCAGATGAATATACAGTAACAGTACCTTTTACAT
049 CGGGAGAAACAATAACGGATTCGCCTGATTGCTTTGAATACCAAGTTACAAAATCGCGCA
050 GAGGCGAATTATTCATTTCAATTACCTGAGCAAAAGAAGATGATGAAACAAACATCAAGA
051 AAACAAAATTAATTACATTTAACAATTTCATTTGAATTACCTTTTTTAATGGAAACAGTA
052 CATAAATCAATATATGTGAGTGAATAACCTTGCTTCTGTAAATCGTCGCTATTAATTAAT
053 TTTCCCTTAGAATCCTTGAAAACATAGCGATAGCTTAGATTAAGACGCTGAGAAGAGTCA
054 ATAGTGAATTTATCAAAATCATAGGTCTGAGAGACTACCTTTTAACCTCCGGCTTAGGT
055 TGGGTTATATAACTATATGTAAATGCTGATGCAAATCCAATCGCAAGACAAAGAACGCGA
056 GAAACTTTTTCAAATATATTTTAGTTAATTTCATCTTCTGACCTAAATTTAATGGTTTG
057 AAATACCGACCGTGTGATAATAAGGCGTTAAATAAGAATAAACACCGGAATCATAATTA
058 CTAGAAAAGCCTGTTTAGTATCATATGCGTTATACAAATTCTTACCAGTATAAAGCCAA
059 CGCTCAACAGTAGGGCTTAATTGAGAATCGCCATATTTAACAACGCCAACATGTAATTTA
060 GGCAGAGGCATTTTCGAGCCAGTAATAAGAGAATATAAAGTACCGACAAAAGGTAAAGTA
```

FIG. 1A (continued)

061 ATTCTGTCCAGACGACGACAATAAACAACATGTTCAGCTAATGCAGAACGCGCCTGTTTA
062 TCAACAATAGATAAGTCCTGAACAAGAAAAATAATATCCCATCCTAATTTACGAGCATGT
063 AGAAACCAATCAATAATCGGCTGTCTTTCCTTATCATTCCAAGAACGGGTATTAAACCAA
064 GTACCGCACTCATCGAGAACAAGCAAGCCGTTTTTATTTTCATCGTAGGAATCATTACCG
065 CGCCCAATAGCAAGCAAATCAGATATAGAAGGCTTATCCGGTATTCTAAGAACGCGAGGC
066 GTTTTAGCGAACCTCCCGACTTGCGGGAGGTTTTGAAGCCTTAAATCAAGATTAGTTGCT
067 ATTTTGCACCCAGCTACAATTTTATCCTGAATCTTACCAACGCTAACGAGCGTCTTTCCA
068 GAGCCTAATTTGCCAGTTACAAAATAAACAGCCATATTATTTATCCCAATCCAAATAAGA
069 AACGATTTTTTGTTTAACGTCAAAAATGAAAATAGCAGCCTTTACAGAGAGAATAACATA
070 AAAACAGGGAAGCGCATTAGACGGGAGAATTAACTGAACACCCTGAACAAAGTCAGAGGG
071 TAATTGAGCGCTAATATCAGAGAGATAACCCACAAGAATTGAGTTAAGCCCAATAATAAG
072 AGCAAGAAACAATGAAATAGCAATAGCTATCTTACCGAAGCCCTTTTTAAGAAAAGTAAG
073 CAGATAGCCGAACAAAGTTACCAGAAGGAAACCGAGGAAACGCAATAATAACGGAATACC
074 CAAAAGAACTGGCATGATTAAGACTCCTTATTACGCAGTATGTTAGCAAACGTAGAAAAT
075 ACATACATAAAGGTGGCAACATATAAAGAAACGCAAAGACACCACGGAATAAGTTTATT
076 TTGTCACAATCAATAGAAAATTCATATGGTTTACCAGCGCCAAAGACAAAAGGGCGACAT
077 TCAACCGATTGAGGGAGGGAAGGTAAATATTGACGGAAATTATTCATTAAAGGTGAATTA
078 TCACCGTCACCGACTTGAGCCATTTGGGAATTAGAGCCAGCAAAATCACCAGTAGCACCA
079 TTACCATTAGCAAGGCCGGAAACGTCACCAATGAAACCATCGATAGCAGCACCGTAATCA
080 GTAGCGACAGAATCAAGTTTGCCTTTAGCGTCAGACTGTAGCGCGTTTTCATCGGCATTT
081 TCGGTCATAGCCCCCTTATTAGCGTTTGCCATCTTTTCATAATCAAAATCACCGGAACCA
082 GAGCCACCACCGGAACCGCCTCCCTCAGAGCCGCCACCCTCAGAACCGCCACCCTCAGAG
083 CCACCACCCTCAGAGCCGCCACCAGAACCACCACCAGAGCCGCCGCCAGCATTGACAGGA
084 GGTTGAGGCAGGTCAGACGATTGGCCTTGATATTCACAAACAAATAAATCCTCATTAAAG
085 CCAGAATGGAAAGCGCAGTCTCTGAATTTACCGTTCCAGTAAGCGTCATACATGGCTTTT
086 GATGATACAGGAGTGTACTGGTAATAAGTTTTAACGGGGTCAGTGCCTTGAGTAACAGTG
087 CCCGTATAAACAGTTAATGCCCCCTGCCTATTTCGGAACCTATTATTCTGAAACATGAAA
088 GTATTAAGAGGCTGAGACTCCTCAAGAGAAGGATTAGGATTAGCGGGGTTTTGCTCAGTA
089 CCAGGCGGATAAGTGCCGTCGAGAGGGTTGATATAAGTATAGCCCGGAATAGGTGTATCA
090 CCGTACTCAGGAGGTTTAGTACCGCCACCCTCAGAACCGCCACCCTCAGAACCGCCACCC

FIG. 1A (continued)

```
091  TCAGAGCCACCACCCTCATTTTCAGGGATAGCAAGCCCAATAGGAACCCATGTACCGTAA
092  CACTGAGTTTCGTCACCAGTACAAACTACAACGCCTGTAGCATTCCACAGACAGCCCTCA
093  TAGTTAGCGTAACGATCTAAAGTTTTGTCGTCTTTCCAGACGTTAGTAAATGAATTTCT
094  GTATGGATTTTGCTAAACAACTTTCAACAGTTTCAGCGGAGTGAGAATAGAAAGGAACA
095  ACTAAAGGAATTGCGAATAATAATTTTTTCACGTTGAAAATCTCCAAAAAAAGGCTCCA
096  AAGGAGCCTTTAATTGTATCGGTTTATCAGCTTGCTTTCGAGGTGAATTTCTTAAACAG
097  CTTGATACCGATAGTTGCGCCGACAATGACAACAACCATCGCCCACGCATAACCGATATA
098  TTCGGTCGCTGAGGCTTGCAGGGAGTTAAAGGCCGCTTTTGCGGGATCGTCACCCTCAGC
099  AGCGAAAGACAGCATCGGAACGAGGGTAGCAACGGCTACAGAGGCTTTGAGGACTAAAGA
100  CTTTTCATGAGGAAGTTTCCATTAAACGGGTAAAATACGTAATGCCACTACGAAGGCAC
101  CAACCTAAAACGAAAGAGGCAAAGAATACACTAAAACACTCATCTTTGACCCCCAGCGA
102  TTATACCAAGCGCGAAACAAAGTACAACGGAGATTTGTATCATCGCCTGATAAATTGTGT
103  CGAAATCCGCGACCTGCTCCATGTTACTTAGCCGGAACGAGGCGCAGACGGTCAATCATA
104  AGGAACCGAACTGACCAACTTTGAAAGAGGACAGATGAACGGTGTACAGACCAGGCGCA
105  TAGGCTGGCTGACCTTCATCAAGAGTAATCTTGACAAGAACCGGATATTCATTACCCAAA
106  TCAACGTAACAAAGCTGCTCATTCAGTGAATAAGGCTTGCCCTGACGAGAAACACCAGAA
107  CGAGTAGTAAATTGGGCTTGAGATGGTTTAATTTCAACTTTAATCATTGTGAATTACCTT
108  ATGCGATTTTAAGAACTGGCTCATTATACCAGTCAGGACGTTGGGAAGAAAAATCTACGT
109  TAATAAAACGAACTAACGGAACAACATTATTACAGGTAGAAAGATTCATCAGTTGAGATT
110  TAGGAATACCACATTCAACTAATGCAGATACATAACGCCAAAAGGAATACGAGGCATAG
111  TAAGAGCAACACTATCATAACCCTCGTTTACCAGACGACGATAAAAACCAAAATAGCGAG
112  AGGCTTTTGCAAAAGAAGTTTTGCCAGAGGGGGTAATAGTAAAATGTTTAGACTGGATAG
113  CGTCCAATACTGCGGAATCGTCATAAATATTCATTGAATCCCCCTCAAATGCTTTAAACA
114  GTTCAGAAAACGAGAATGACCATAAATCAAAAATCAGGTCTTTACCCTGACTATTATAGT
115  CAGAAGCAAAGCGGATTGCATCAAAAAGATTAAGAGGAAGCCCGAAAGACTTCAAATATC
116  GCGTTTTAATTCGAGCTTCAAAGCGAACCAGACCGGAAGCAAACTCCAACAGGTCAGGAT
117  TAGAGAGTACCTTAATTGCTCCTTTTGATAAGAGGTCATTTTGCGGATGGCTTAGAGC
118  TTAATTGCTGAATATAATGCTGTAGCTCAACATGTTTTAAATATGCAACTAAAGTACGGT
119  GTCTGGAAGTTTCATTCCATATAACAGTTGATTCCCAATTCTGCGAACGAGTAGATTTAG
120  TTTGACCATTAGATACATTTCGCAAATGGTCAATAACCTGTTTAGCTATATTTTCATTTG
121  GGGCGCGAGCTGAAAAGGTGGCATCAATTCTACTAATAGTAGTAGCATT
```

Oligo for M13 linearization
```
000A  CTACTAATAGTAGTAGCATTAACATCCAATAAATCATACA   BtsCI cut site oligo
```

Labeled oligos
```
001A  5' dual biotin - AACATCCAATAAATCATACAGGCAAGGCAAAGAATTAGCAAAATTAAGCAATAAAGCCTC
033A  TCTGTCCATCACGCAAATTAACCGTTGTAGCAATACTTCTTTGATTAGTAATAACATCAC - 3'thiol
044A  5' dig - ATTCGACAACTCGTATTAAATCCTTTGCCCGAACGTTATTAATTTAAAAGTTTCAGTAA
121A  GGGCCCGAGCTGAAAAGGTGGCATCAATTCTACTAATAGTAGTAGCATT - dT internal biotin 3' biotin
```

FIG. 1A (continued)

Bridge oligos

Binds M13 from bases 1950-1980

Binds M13 starting at:
base 2500 (short loop)
base 4560 (long loop)

033-044A  CAATACTTCTTTGATTAGTAATAACATCACATTCGACAACTCGTATTAAATCCTTTGCCC (60bp short loop bridge oligo)

033-044B  CAATACTTCTTTGATTAGTAATAACATCACATTCGACAACTCGTATTAAA (50bp short loop bridge oligo)

033-044C  CAATACTTCTTTGATTAGTAATAACATCACATTCGACAACTCGTA (45bp short loop bridge oligo)

033-044D  CAATACTTCTTTGATTAGTAATAACATCACATTCGACAAC (40bp short loop bridge oligo)

033-077A  CAATACTTCTTTGATTAGTAATAACATCACTCAACCGATTGAGGGAGGAAAGGTAAATAT (60bp short loop bridge oligo)

033-077B  CAATACTTCTTTGATTAGTAATAACATCACTCAACCGATTGAGGGAGGGA (50bp short loop bridge oligo)

033-077C  CAATACTTCTTTGATTAGTAATAACATCACTCAACCGATTGAGGG (45bp short loop bridge oligo)

033-077D  CAATACTTCTTTGATTAGTAATAACATCACTCAACCGATT (40bp short loop bridge oligo)

tau = 6.4 minutes

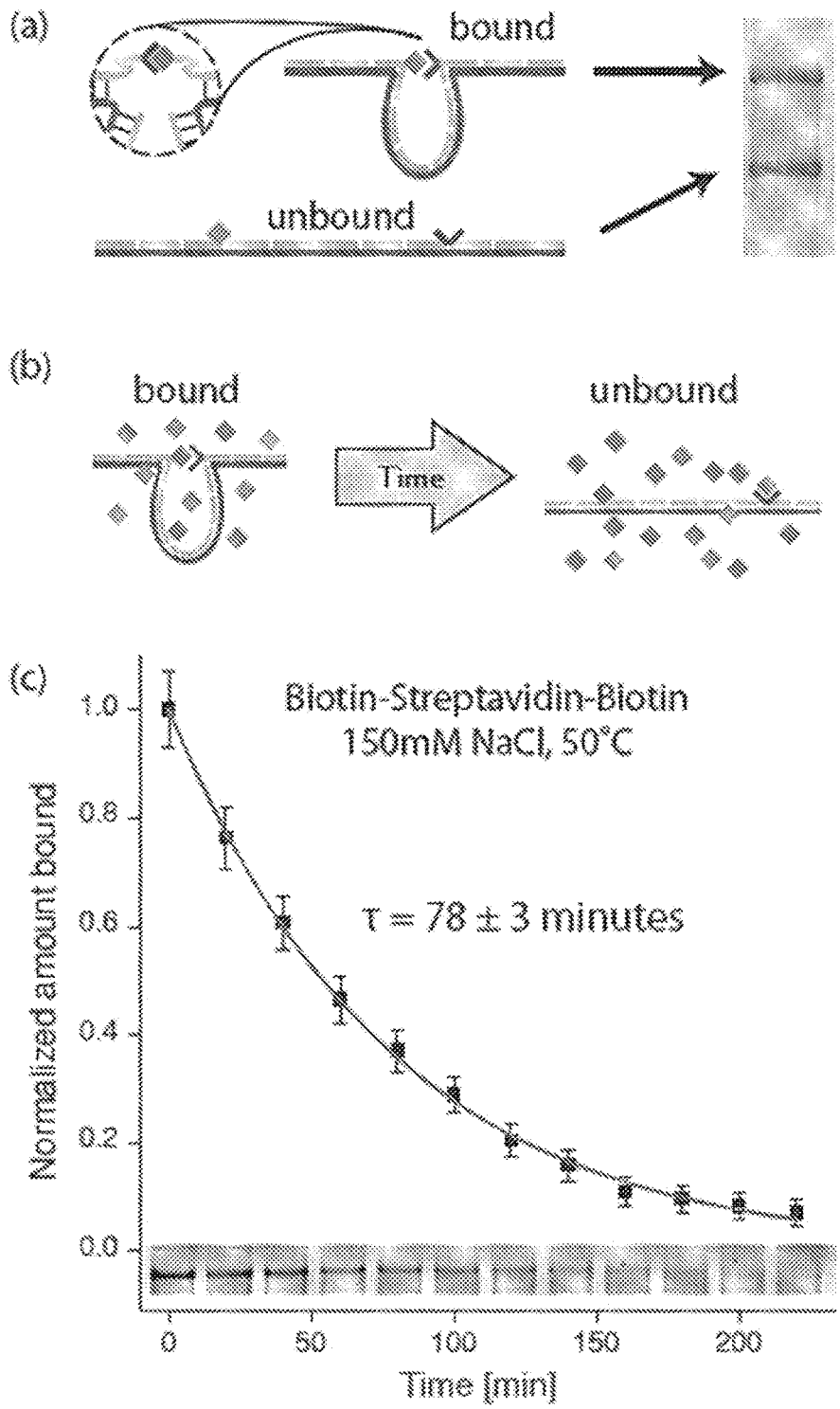
FIGs. 7A-C

Biotin-Streptavidin-Biotin dissociation time (hours)

| NaCl | 4°C | 25°C | 37°C | 50°C |
|---|---|---|---|---|
| 5 mM | 490 | 93 | 9.6 | 0.6 |
| 25 mM | 670 | 97 | 9.7 | 1.1 |
| 150 mM | >1000 | 148 | 11.2 | 1.4 |
| 500 mM | 130 | 85 | 12.9 | 1.3 |

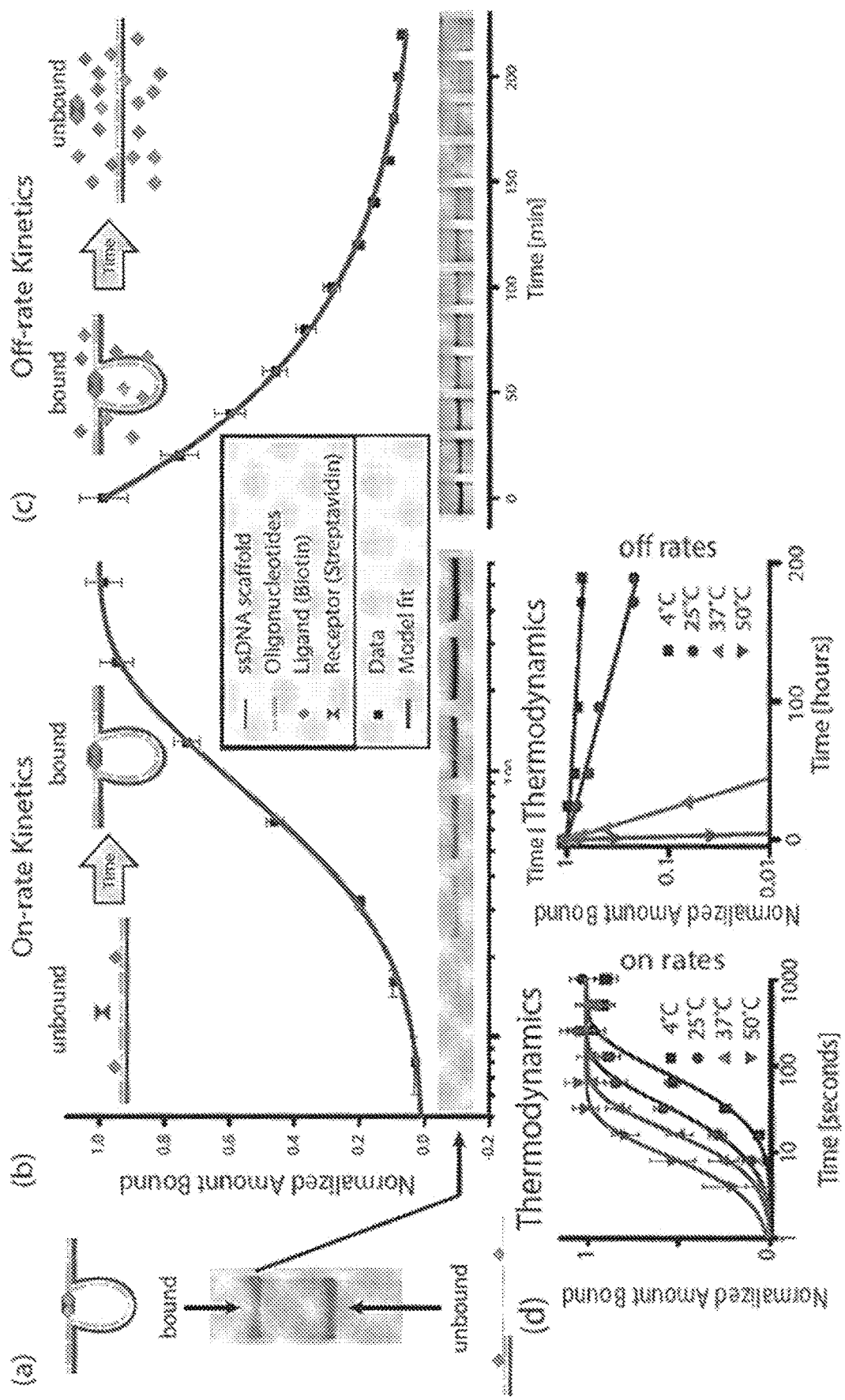
FIGs. 9A-D

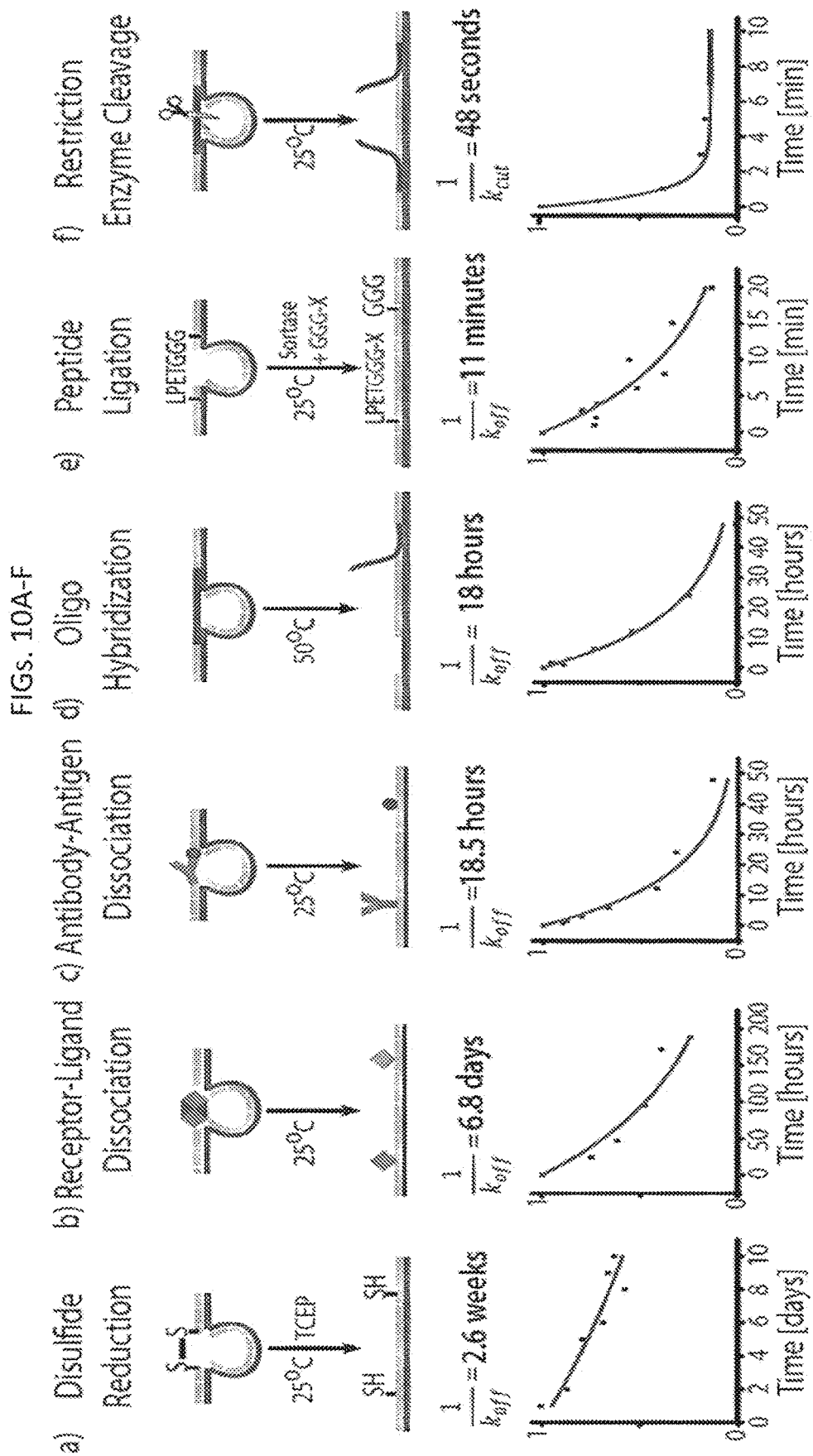
FIGs. 10A-F

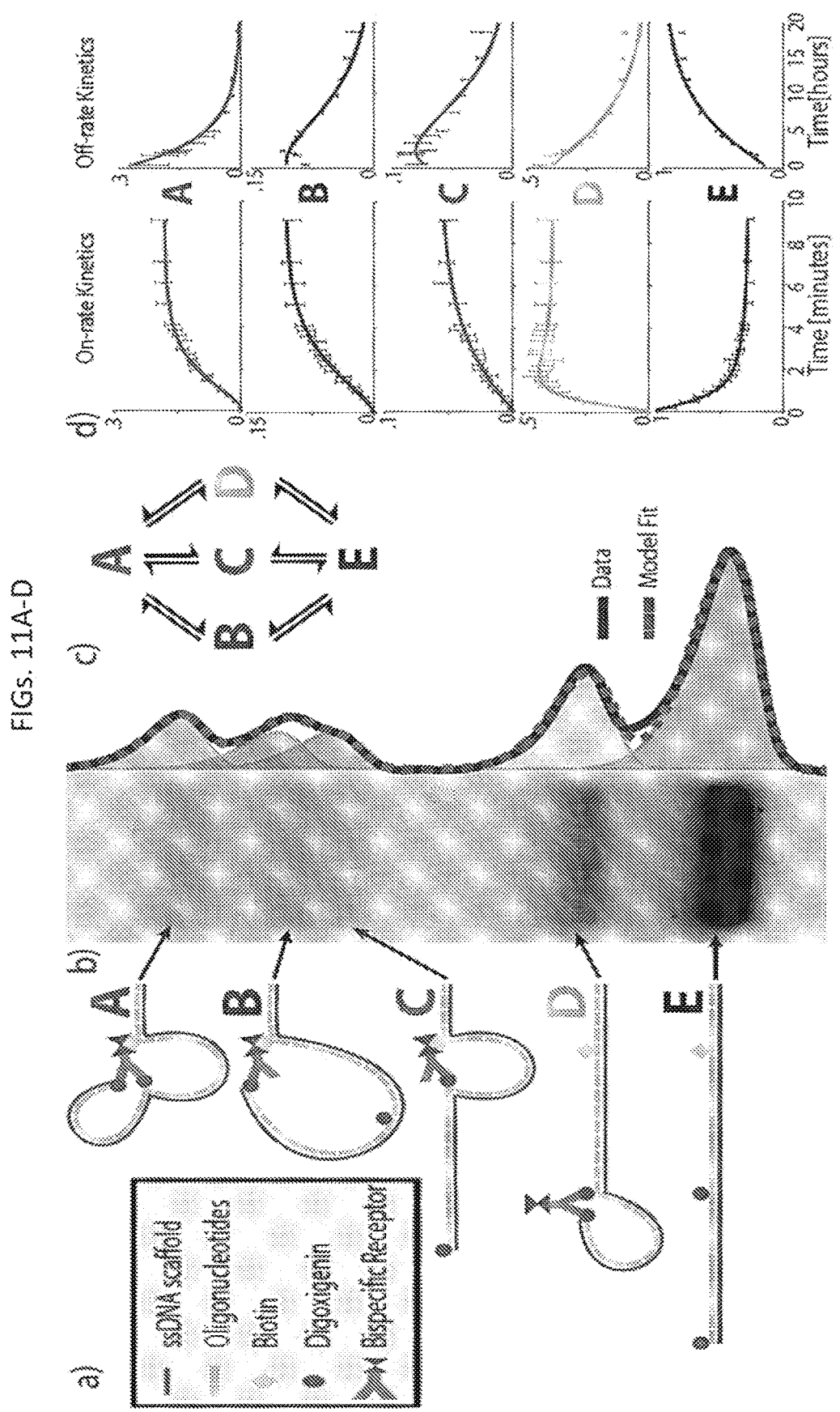
FIGs. 11A-D

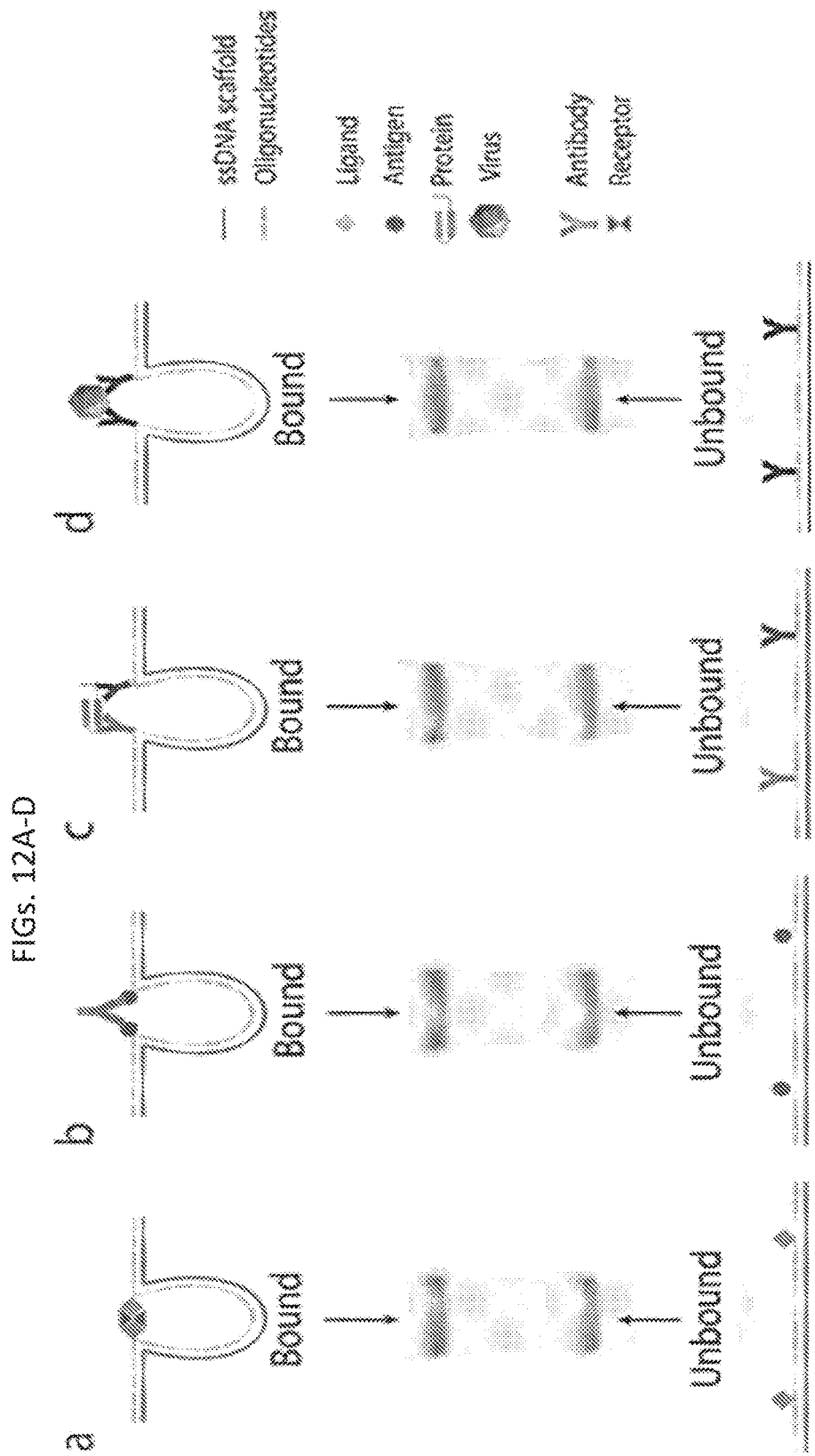
FIGs. 12A-D

SEQUENCE LISTING

<160> NUMBER OF SEQ ID NOS: 134

<210> SEQ ID NO 1
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 1
aacatccaat aaatcataca ggcaaggcaa agaattagca aaattaagca ataaagcctc     60

<210> SEQ ID NO 2
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 2
agagcataaa gctaaatcgg ttgtaccaaa aacattatga ccctgtaata cttttgcggg     60

<210> SEQ ID NO 3
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 3
agaagccttt atttcaacgc aaggataaaa atttttagaa ccctcatata ttttaaatgc     60

<210> SEQ ID NO 4
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 4
aatgcctgag taatgtgtag gtaaagattc aaaagggtga gaaaggccgg agacagtcaa     60

<210> SEQ ID NO 5
<211> LENGTH: 60

```
<212> TYPE: DNA
<213> ORGANISM: Artificial Sequence
<220> FEATURE:
<223> OTHER INFORMATION: Synthetic Oligonucleotide

<400> SEQUENCE: 5
atcaccatca atatgatatt caaccgttct agctgataaa ttaatgccgg agagggtagc    60

<210> SEQ ID NO 6
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 6 tattttgag agatctacaa aggctatcag gtcattgcct gagagtctgg agcaaacaag    60

<210> SEQ ID NO 7
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 7
agaatcgatg aacggtaatc gtaaaactag catgtcaatc atatgtaccc cggttgataa    60

<210> SEQ ID NO 8
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 8
tcagaaaagc cccaaaaaca ggaagattgt ataagcaaat atttaaattg taaacgttaa    60

<210> SEQ ID NO 9
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 9
tattttgtta aaattcgcat taaattttttg ttaaatcagc tcattttta accaatagga    60

<210> SEQ ID NO 10
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 10
acgccatcaa aaataattcg cgtctggcct tcctgtagcc agctttcatc aacattaaat    60

<210> SEQ ID NO 11
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 11
```
gtgagcgagt aacaacccgt cggattctcc gtgggaacaa acggcggatt gaccgtaatg    60

<210> SEQ ID NO 12
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 12
ggataggtca cgttggtgta gatgggcgca tcgtaaccgt gcatctgcca gtttgagggg    60

<210> SEQ ID NO 13
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 13
acgacgacag tatcggcctc aggaagatcg cactccagcc agctttccgg caccgcttct    60

<210> SEQ ID NO 14
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 14
ggtgccggaa accaggcaaa gcgccattcg ccattcaggc tgcgcaactg ttgggaaggg    60

<210> SEQ ID NO 15
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 15
cgatcggtgc gggcctcttc gctattacgc cagctggcga aggggggatg tgctgcaagg    60

<210> SEQ ID NO 16
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 16
cgattaagtt gggtaacgcc agggttttcc cagtcacgac gttgtaaaac gacggccagt    60

<210> SEQ ID NO 17
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 17
gccaagcttg catgcctgca ggtcgactct agaggatccc cgggtaccga gctcgaattc    60

<210> SEQ ID NO 18
<211> LENGTH: 60
<212> TYPE: DNA
<213> ORGANISM: Artificial Sequence

```
<220> FEATURE:
<223> OTHER INFORMATION: Synthetic Oligonucleotide

<400> SEQUENCE: 18
gtaatcatgg tcatagctgt ttcctgtgtg aaattgttat ccgctcacaa ttccacacaa    60

<210> SEQ ID NO 19
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 19
catacgagcc ggaagcataa agtgtaaagc ctggggtgcc taatgagtga gctaactcac    60

<210> SEQ ID NO 20
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 20
attaattgcg ttgcgctcac tgcccgcttt ccagtcggga aacctgtcgt gccagctgca    60

<210> SEQ ID NO 21
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 21
ttaatgaatc ggccaacgcg cggggagagg cggtttgcgt attgggcgcc agggtggttt    60

<210> SEQ ID NO 22
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 22
ttcttttcac cagtgagacg ggcaacagct gattgcccct caccgcctgg ccctgagaga    60

<210> SEQ ID NO 23
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 23
gttgcagcaa gcggtccacg ctggtttgcc ccagcaggcg aaaatcctgt ttgatggtgg    60

<210> SEQ ID NO 24
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 24
ttccgaaatc ggcaaaatcc cttataaatc aaaagaatag cccgagatag ggttgagtgt    60
```

<210> SEQ ID NO 25
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 25
tgttccagtt tggaacaaga gtccactatt aaagaacgtg gactccaacg tcaaagggcg    60

<210> SEQ ID NO 26
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 26
aaaaaccgtc tatcagggcg atggcccact acgtgaacca tcacccaaat caagtttttt    60

<210> SEQ ID NO 27
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 27
ggggtcgagg tgccgtaaag cactaaatcg gaaccctaaa gggagccccc gatttagagc    60

<210> SEQ ID NO 28
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 28
ttgacgggga agccggcga acgtggcgag aaggaaggg aagaaagcga aggagcggg    60

<210> SEQ ID NO 29
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 29
cgctagggcg ctggcaagtg tagcggtcac gctgcgcgta accaccacac ccgccgcgct    60

<210> SEQ ID NO 30
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 30
taatgcgccg ctacagggcg cgtactatgg ttgctttgac gagcacgtat aacgtgcttt    60

<210> SEQ ID NO 31
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 31
cctcgttaga atcagagcgg gagctaaaca ggaggccgat taaagggatt ttagacagga    60

<210> SEQ ID NO 32
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 32
acggtacgcc agaatcctga gaagtgtttt tataatcagt gaggccaccg agtaaaagag    60

<210> SEQ ID NO 33
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 33
tctgtccatc acgcaaatta accgttgtag caatacttct ttgattagta ataacatcac    60

<210> SEQ ID NO 34
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 34
ttgcctgagt agaagaactc aaactatcgg ccttgctggt aatatccaga acaatattac    60

<210> SEQ ID NO 35
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 35
cgccagccat tgcaacagga aaaacgctca tggaaatacc tacattttga cgctcaatcg    60

<210> SEQ ID NO 36
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 36
tctgaaatgg attatttaca ttggcagatt caccagtcac acgaccagta ataaaggga    60

<210> SEQ ID NO 37
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 37
cattctggcc aacagagata gaaccttct gacctgaaag cgtaagaata cgtggcacag    60

<210> SEQ ID NO 38

```
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 38
acaatatttt tgaatggcta ttagtcttta atgcgcgaac tgatagccct aaaacatcgc    60

<210> SEQ ID NO 39
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 39
cattaaaaat accgaacgaa ccaccagcag aagataaaac agaggtgagg cggtcagtat    60

<210> SEQ ID NO 40
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 40
taacaccgcc tgcaacagtg ccacgctgag agccagcagc aaatgaaaaa tctaaagcat    60

<210> SEQ ID NO 41
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 41
caccttgctg aacctcaaat atcaaaccct caatcaatat ctggtcagtt ggcaaatcaa    60

<210> SEQ ID NO 42
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 42
cagttgaaag gaattgagga aggttatcta aaatatcttt aggagcacta caactaata     60

<210> SEQ ID NO 43
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 43
gattagagcc gtcaatagat aatacatttg aggatttaga agtattagac tttacaaaca    60

<210> SEQ ID NO 44
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 44
```

```
attcgacaac tcgtattaaa tcctttgccc gaacgttatt aattttaaaa gtttgagtaa    60

<210> SEQ ID NO 45
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 45
cattatcatt ttgcggaaca aagaaaccac cagaaggagc ggaattatca tcatattcct    60

<210> SEQ ID NO 46
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 46
gattatcaga tgatggcaat tcatcaatat aatcctgatt gtttggatta tacttctgaa    60

<210> SEQ ID NO 47
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 47
taatggaagg gttagaacct accatatcaa aattatttgc acgtaaaaca gaaataaaga    60

<210> SEQ ID NO 48
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 48
aattgcgtag attttcaggt ttaacgtcag atgaatatac agtaacagta cctttacat    60

<210> SEQ ID NO 49
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 49
cgggagaaac aataacggat tcgcctgatt gctttgaata ccaagttaca aaatcgcgca    60

<210> SEQ ID NO 50
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 50
gaggcgaatt attcatttca attacctgag caaaagaaga tgatgaaaca aacatcaaga    60

<210> SEQ ID NO 51
<211> LENGTH: 60
<212> TYPE: DNA
```

```
<213> ORGANISM: Artificial Sequence
<220> FEATURE:
<223> OTHER INFORMATION: Synthetic Oligonucleotide

<400> SEQUENCE: 51
aaacaaaatt aattacattt aacaatttca tttgaattac cttttttaat ggaaacagta        60

<210> SEQ ID NO 52
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 52
cataaatcaa tatatgtgag tgaataacct tgcttctgta aatcgtcgct attaattaat        60

<210> SEQ ID NO 53
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 53
tttcccttag aatccttgaa aacatagcga tagcttagat taagacgctg agaagagtca        60

<210> SEQ ID NO 54
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 54
atagtgaatt tatcaaaatc ataggtctga gagactacct ttttaacctc cggcttaggt        60

<210> SEQ ID NO 55
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 55
tgggttatat aactatatgt aaatgctgat gcaaatccaa tcgcaagaca aagaacgcga        60

<210> SEQ ID NO 56
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 56
gaaaactttt tcaaatatat tttagttaat ttcatcttct gacctaaatt taatggtttg        60

<210> SEQ ID NO 57
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 57
aaataccgac cgtgtgataa ataaggcgtt aaataagaat aaacaccgga atcataatta        60
```

<210> SEQ ID NO 58
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 58
ctagaaaaag cctgtttagt atcatatgcg ttatacaaat tcttaccagt ataaagccaa        60

<210> SEQ ID NO 59
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 59
cgctcaacag tagggcttaa ttgagaatcg ccatatttaa caacgccaac atgtaattta        60

<210> SEQ ID NO 60
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 60
ggcagaggca ttttcgagcc agtaataaga gaatataaag taccgacaaa aggtaaagta        60

<210> SEQ ID NO 61
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 61
attctgtcca gacgacgaca ataaacaaca tgttcagcta atgcagaacg cgcctgttta        60

<210> SEQ ID NO 62
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 62
tcaacaatag ataagtcctg aacaagaaaa ataatatccc atcctaattt acgagcatgt        60

<210> SEQ ID NO 63
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 63
agaaaccaat caataatcgg ctgtctttcc ttatcattcc aagaacgggt attaaaccaa        60

<210> SEQ ID NO 64
<211> LENGTH: 60
<212> TYPE: DNA
<213> ORGANISM: Artificial Sequence
<220> FEATURE:

<223> OTHER INFORMATION: Synthetic Oligonucleotide

<400> SEQUENCE: 64
gtaccgcact catcgagaac aagcaagccg tttttatttt catcgtagga atcattaccg    60

<210> SEQ ID NO 65
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 65
cgcccaatag caagcaaatc agatatagaa ggcttatccg gtattctaag aacgcgaggc    60

<210> SEQ ID NO 66
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 66
gttttagcga acctcccgac ttgcgggagg ttttgaagcc ttaaatcaag attagttgct    60

<210> SEQ ID NO 67
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 67
attttgcacc cagctacaat tttatcctga atcttaccaa cgctaacgag cgtctttcca    60

<210> SEQ ID NO 68
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 68
gagcctaatt tgccagttac aaaataaaca gccatattat ttatcccaat ccaaataaga    60

<210> SEQ ID NO 69
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 69
aacgattttt tgtttaacgt caaaaatgaa aatagcagcc tttacagaga gaataacata    60

<210> SEQ ID NO 70
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 70
aaaacaggga agcgcattag acgggagaat taactgaaca ccctgaacaa agtcagaggg    60

<210> SEQ ID NO 71
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 71
taattgagcg ctaatatcag agagataacc cacaagaatt gagttaagcc caataataag    60

<210> SEQ ID NO 72
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 72
agcaagaaac aatgaaatag caatagctat cttaccgaag ccctttttaa gaaaagtaag    60

<210> SEQ ID NO 73
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 73
cagatagccg aacaaagtta ccagaaggaa accgaggaaa cgcaataata acggaatacc    60

<210> SEQ ID NO 74
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 74
caaaagaact ggcatgatta agactcctta ttacgcagta tgttagcaaa cgtagaaaat    60

<210> SEQ ID NO 75
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 75
acatacataa aggtggcaac atataaaaga aacgcaaaga caccacggaa taagtttatt    60

<210> SEQ ID NO 76
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 76
ttgtcacaat caatagaaaa ttcatatggt ttaccagcgc caaagacaaa agggcgacat    60

<210> SEQ ID NO 77
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 77
tcaaccgatt gagggaggga aggtaaatat tgacggaaat tattcattaa aggtgaatta    60

<210> SEQ ID NO 78
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 78
tcaccgtcac cgacttgagc catttgggaa ttagagccag caaaatcacc agtagcacca    60

<210> SEQ ID NO 79
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 79
ttaccattag caaggccgga aacgtcacca atgaaaccat cgatagcagc accgtaatca    60

<210> SEQ ID NO 80
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 80
gtagcgacag aatcaagttt gcctttagcg tcagactgta gcgcgttttc atcggcattt    60

<210> SEQ ID NO 81
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 81
tcggtcatag cccccttatt agcgtttgcc atcttttcat aatcaaaatc accggaacca    60

<210> SEQ ID NO 82
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 82
gagccaccac cggaaccgcc tccctcagag ccgccaccct cagaaccgcc accctcagag    60

<210> SEQ ID NO 83
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 83
ccaccaccct cagagccgcc accagaacca ccaccagagc cgccgccagc attgacagga    60

<210> SEQ ID NO 84
<211> LENGTH: 60

```
<212> TYPE: DNA
<213> ORGANISM: Artificial Sequence
<220> FEATURE:
<223> OTHER INFORMATION: Synthetic Oligonucleotide

<400> SEQUENCE: 84
ggttgaggca ggtcagacga ttggccttga tattcacaaa caaataaatc ctcattaaag      60

<210> SEQ ID NO 85
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 85
ccagaatgga aagcgcagtc tctgaattta ccgttccagt aagcgtcata catggctttt      60

<210> SEQ ID NO 86
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 86
gatgatacag gagtgtactg gtaataagtt ttaacggggt cagtgccttg agtaacagtg      60

<210> SEQ ID NO 87
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 87
cccgtataaa cagttaatgc cccctgccta tttcggaacc tattattctg aaacatgaaa      60

<210> SEQ ID NO 88
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 88
gtattaagag gctgagactc ctcaagagaa ggattaggat tagcggggtt ttgctcagta      60

<210> SEQ ID NO 89
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 89
ccaggcggat aagtgccgtc gagagggttg atataagtat agcccggaat aggtgtatca      60

<210> SEQ ID NO 90
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 90
```
ccgtactcag gaggtttagt accgccaccc tcagaaccgc caccctcaga accgccaccc    60

<210> SEQ ID NO 91
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 91
tcagagccac caccctcatt ttcagggata gcaagcccaa taggaaccca tgtaccgtaa    60

<210> SEQ ID NO 92
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 92
cactgagttt cgtcaccagt acaaactaca acgcctgtag cattccacag acagccctca    60

<210> SEQ ID NO 93
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 93
tagttagcgt aacgatctaa agttttgtcg tctttccaga cgttagtaaa tgaattttct    60

<210> SEQ ID NO 94
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 94
gtatgggatt tgctaaaca actttcaaca gtttcagcgg agtgagaata gaaaggaaca    60

<210> SEQ ID NO 95
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 95
actaaaggaa ttgcgaataa taattttttc acgttgaaaa tctccaaaaa aaaggctcca    60

<210> SEQ ID NO 96
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 96
aaaggagcct ttaattgtat cggtttatca gcttgctttc gaggtgaatt tcttaaacag    60

<210> SEQ ID NO 97
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 97
cttgataccg atagttgcgc cgacaatgac aacaaccatc gcccacgcat aaccgatata    60

<210> SEQ ID NO 98
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 98
ttcggtcgct gaggcttgca gggagttaaa ggccgctttt gcgggatcgt caccctcagc    60

<210> SEQ ID NO 99
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 99
agcgaaagac agcatcggaa cgagggtagc aacggctaca gaggctttga ggactaaaga    60

<210> SEQ ID NO 100
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 100
ctttttcatg aggaagtttc cattaaacgg gtaaaatacg taatgccact acgaaggcac    60

<210> SEQ ID NO 101
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 101
caacctaaaa cgaaagaggc aaaagaatac actaaaacac tcatctttga cccccagcga    60

<210> SEQ ID NO 102
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 102
ttataccaag cgcgaaacaa agtacaacgg agatttgtat catcgcctga taaattgtgt    60

<210> SEQ ID NO 103
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 103
cgaaatccgc gacctgctcc atgttactta gccggaacga ggcgcagacg gtcaatcata    60

<210> SEQ ID NO 104
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 104
agggaaccga actgaccaac tttgaaagag gacagatgaa cggtgtacag accaggcgca    60

<210> SEQ ID NO 105
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 105
taggctggct gaccttcatc aagagtaatc ttgacaagaa ccggatattc attacccaaa    60

<210> SEQ ID NO 106
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 106
tcaacgtaac aaagctgctc attcagtgaa taaggcttgc cctgacgaga acaccagaa    60

<210> SEQ ID NO 107
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 107
cgagtagtaa attgggcttg agatggttta atttcaactt taatcattgt gaattacctt    60

<210> SEQ ID NO 108
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 108
atgcgatttt aagaactggc tcattatacc agtcaggacg ttgggaagaa aaatctacgt    60

<210> SEQ ID NO 109
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 109
taataaaacg aactaacgga acaacattat tacaggtaga aagattcatc agttgagatt    60

<210> SEQ ID NO 110
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 110
taggaatacc acattcaact aatgcagata cataacgcca aaaggaatta cgaggcatag    60

<210> SEQ ID NO 111
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 111
taagagcaac actatcataa ccctcgttta ccagacgacg ataaaaacca aaatagcgag    60

<210> SEQ ID NO 112
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 112
aggcttttgc aaaagaagtt ttgccagagg gggtaatagt aaaatgttta gactggatag    60

<210> SEQ ID NO 113
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 113
cgtccaatac tgcggaatcg tcataaatat tcattgaatc cccctcaaat gctttaaaca    60

<210> SEQ ID NO 114
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 114
gttcagaaaa cgagaatgac cataaatcaa aaatcaggtc tttaccctga ctattatagt    60

<210> SEQ ID NO 115
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 115
cagaagcaaa gcggattgca tcaaaaagat taagaggaag cccgaaagac ttcaaatatc    60

<210> SEQ ID NO 116
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 116
gcgttttaat tcgagcttca aagcgaacca gaccggaagc aaactccaac aggtcaggat    60

<210> SEQ ID NO 117

```
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 117
tagagagtac ctttaattgc tcctttgat aagaggtcat ttttgcggat ggcttagagc    60

<210> SEQ ID NO 118
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 118
ttaattgctg aatataatgc tgtagctcaa catgttttaa atatgcaact aaagtacggt    60

<210> SEQ ID NO 119
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 119
gtctggaagt ttcattccat ataacagttg attcccaatt ctgcgaacga gtagatttag    60

<210> SEQ ID NO 120
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 120
tttgaccatt agatacattt cgcaaatggt caataacctg tttagctata ttttcatttg    60

<210> SEQ ID NO 121
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 121
gggcgcgagc tgaaaaggtg gcatcaattc tactaatagt agtagcatt                49

<210> SEQ ID NO 122
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 122
ctactaatag tagtagcatt aacatccaat aaatcataca                          40

<210> SEQ ID NO 123
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 123
```
aacatccaat aaatcataca ggcaaggcaa agaattagca aaattaagca ataaagcctc    60

<210> SEQ ID NO 124
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 124
tctgtccatc acgcaaatta accgttgtag caatacttct ttgattagta ataacatcac    60

<210> SEQ ID NO 125
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 125
attcgacaac tcgtattaaa tcctttgccc gaacgttatt aattttaaaa gtttgagtaa    60

<210> SEQ ID NO 126
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 126
gggcgcgagc tgaaaaggtg gcatcaattc tactaatagt agtagcatt                49

<210> SEQ ID NO 127
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 127
caatacttct tgattagta ataacatcac attcgacaac tcgtattaaa tcctttgccc    60

<210> SEQ ID NO 128
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 128
caatacttct ttgattagta ataacatcac attcgacaac tcgtattaaa                50

<210> SEQ ID NO 129
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 129
caatacttct ttgattagta ataacatcac attcgacaac tcgta                    45

<210> SEQ ID NO 130
<211> LENGTH: 40
<212> TYPE: DNA

<213> ORGANISM: Artificial Sequence
<220> FEATURE:
<223> OTHER INFORMATION: Synthetic Oligonucleotide

<400> SEQUENCE: 130
caatacttct tgattagta ataacatcac attcgacaac           40

<210> SEQ ID NO 131
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 131
caatacttct tgattagta ataacatcac tcaaccgatt gagggaggga aggtaaatat           60

<210> SEQ ID NO 132
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 132
caatacttct tgattagta ataacatcac tcaaccgatt gagggaggga           50

<210> SEQ ID NO 133
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 133
caatacttct tgattagta ataacatcac tcaaccgatt gaggg           45

<210> SEQ ID NO 134
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 134
caatacttct tgattagta ataacatcac tcaaccgatt           40

NUCLEIC ACID-BASED LINKERS FOR DETECTING AND MEASURING INTERACTIONS

RELATED APPLICATIONS

This application is a national stage filing under 35 U.S.C. § 371 of International Application PCT/US2015/060952, filed Nov. 16, 2015, entitled "NUCLEIC ACID-BASED LINKERS FOR DETECTING AND MEASURING INTERACTIONS," which claims the benefit under 35 U.S.C. § 119(e) of U.S. provisional application Ser. No. 62/088,592, filed Dec. 6, 2014, the contents of each of which are incorporated by reference herein in their entireties.

FEDERALLY SPONSORED RESEARCH

This invention was made with U.S. Government support under grant number R01DC02281 awarded by the National Institutes of Health. The U.S. Government has certain rights in the invention.

BACKGROUND

The ability to precisely manipulate individual molecules has led to stunning new discoveries in physics, biology, and medicine (Deniz A. A. et al. (2008) J. R. Soc. Interface, 5: 15; Ritort F. et al. (2006) J. Phys.: Condens. Matter 18: R531), as well as powerful new methods in nanoscale engineering. For example, single-molecule force measurements have revealed the basic mechanical properties of nucleic acids (Bustamante C. et al. Nature 421: 423-7), the dynamics and functioning of molecular motors (Svoboda K. et al. (1993) Nature 365: 721-7; Greenleaf W. J. et al. (2007) Annu. Rev. Biophys. Biomol. Struct. 36: 171), and the role of hydrodynamic forces in the circulatory system in regulating enzymatic activity (Zhang X. et al. (2009) Science 324: 1330). In addition, these measurements have yielded fundamental insights into the dynamical strength of molecular interactions (Evans E. (2001) Annu. Rev. Biophys. Biomol. Struct. 30: 105-28), which have led to the development of creative new tools for nanoscale assembly (Kufer S. K. et al. (2008) Science 319: 594).

Mechanical forces can be applied to individual molecules using a broad range of tools, including optical traps, magnetic tweezers, mechanical cantilevers, and the centrifuge force microscope (Neuman K. C. et al. (2008) Nature Methods 5: 491-505; Halvorsen K. et al. (2010) Biophys. J. 98: L53-5). Yet a common requirement of these methods is that single-molecule constructs must be specifically tethered between two surfaces (e.g., beads, cover slips or cantilevers) to enable their manipulation and detection. This leads to one of the major challenges in single-molecule experimentation—verifying that exactly one molecular tether is being pulled, and distinguishing this tether from non-specific and unintended interactions that may occur (e.g., surface-surface interactions, formation of multiple bonds). The success and reliability of single-molecule experiments depends upon the creation of reliable, verifiable and robust linking techniques. This is particularly important for bond rupture studies (e.g., characterizing the strength of molecular adhesion bonds (Evans E. et al. (1997) Biophys. J. 72: 1541-55), DNA base pairing (Strunz T. et al. Proc. Natl Acad. Sci. 96: 11277), and cell adhesion and signaling (Evans E. A. et al. (2007) Science 316: 1148)), as the dissociation between two molecules can be difficult to positively identify due to the lack of an obvious mechanical signature.

SUMMARY

The invention provides, inter alia, compositions comprising a switchable single-molecule linker comprised of two members of a binding pair, such as a receptor and a ligand, integrated onto a nucleic acid (e.g., DNA backbone), methods of making such linkers, and methods of using such linkers, including for example in single-molecule force studies and as molecular on-rate or off-rate sensors using, for example, standard gel electrophoresis. In important embodiments, the complexes provided herein comprise three of more binding partners, wherein the three binding partners interact with each other and/or with other binding partners provided in soluble form or themselves linked to the complex.

The ability to manipulate and observe single biological molecules has led to both fundamental scientific discoveries and new methods in nanoscale engineering. A common challenge in many single-molecule experiments is reliably linking molecules to surfaces and identifying and monitoring their interactions. The invention overcomes this challenge by providing a novel nano-engineered nucleic acid based linker (e.g., a DNA-based linker) that behaves as a force-activated switch, providing a molecular signature that can eliminate errant data arising from non-specific and multiple interactions.

It is to be understood that, for convenience, the invention may refer to the linker of the invention as being "DNA-based". These recitations are not to be construed as limiting the nature of the linker to solely DNA. Accordingly, the DNA-based compositions of the invention are to be construed as exemplary embodiments of the nucleic acid based compositions of the invention.

By integrating both members of a binding pair, such as a receptor and a ligand, into a single piece of DNA using for example DNA self-assembly, a single tether can be positively identified by topological changes (as observed through gel electrophoresis), and binding pair interactions, such as receptor-ligand binding and unbinding, can be easily identified by a gel shifts. Additionally, under proper conditions the exact same pair of molecules can be repeatedly bound and unbound. The approach is simple, versatile and modular, and can be easily implemented using standard commercial reagents and laboratory equipment. This single-molecule mechanical switch paves the way for high-throughput serial measurements, high-throughput identification of binding partners for targets of interest, single-molecule on-rate and off-rate studies, investigations of population heterogeneity, and detection of analytes in samples including low concentration analytes not easily detected heretofore and diagnostic applications relating thereto.

As an example, the linker of the invention, which is referred to herein interchangeably as a nucleic acid complex, may be used as a molecular off-rate (and possibly on-rate) sensor. It was discovered that the two states of the linker (which may be referred to herein as the bound and unbound states or the closed and open states) migrate differently on a standard electrophoresis gel, giving a direct measure of the percentage of bound and unbound product. The following protocol can then be used to measure the off-rate between the receptor and ligand: 1) create stock of linker molecule, 2) add excess ligand or receptor to force all unbound linkers to remain unbound, 3) use a crosslinking agent (e.g., photoactive crosslinker) to "freeze" the bound product at different times, 4) run a gel and measure the decrease in bound products over time. This has been demonstrated successfully, inter alia, where the receptor and ligand are opposite DNA strands that hybridize to each other, and for antigen and antibody binding.

Accordingly, in one aspect, the invention provides a nucleic acid complex comprising a single-stranded scaffold nucleic acid hybridized to a plurality of single-stranded oligonucleotides, wherein a first single-stranded oligonucleotide in the plurality is linked to a first binding partner, a second single-stranded oligonucleotide in the plurality is linked to a second binding partner, and a third single-stranded oligonucleotide in the plurality is linked to a third binding partner. It is to be understood that the scaffold nucleic acid and the oligonucleotides are referred to as being single-stranded prior to their hybridization to each other.

As used herein, regions that are internal to the scaffold, exclude the most 5' and the most 3' nucleotides of the scaffold.

The second binding partner may be known to have affinity for the first binding partner. The second binding partner may be known or unknown (e.g., it may be a library member that is being screened for binding affinity for the first binding partner). The third binding partner may be known to have affinity for the first binding partner or the second binding partner.

In some embodiments, the first, second and/or third binding partners are not nucleic acid in nature. In some embodiments, the first, second and/or third binding partners are amino acid in nature (e.g., they may be peptides, proteins or protein fragments).

In some embodiments, the binding partners may be receptors and ligands of the receptors. In some embodiments, the binding partners may be antibody or an antigen-binding antibody fragment and antigen pairs. It is to be understood that the binding partners may be used in an isolated form (e.g., physically separate from components or moieties with which they naturally occur). In some embodiments, they may be bound to a support such as a cell (e.g., a cell surface receptor or ligand).

In some embodiments, the functionalized single-stranded oligonucleotides such as the first, second, third, and optionally fourth single-stranded oligonucleotides, are separated from each other by at least about 500, 1000, 1500, 2000, 2500, 3000, 3500, 4000, 5000 or more nucleotides. In some embodiments, the functionalized single-stranded oligonucleotides such as the first single-stranded oligonucleotide and the second single-stranded oligonucleotide are located about equi-distant about the center of the scaffold nucleic acid. In some embodiments, the functionalized single-stranded oligonucleotides bind to regions of the scaffold nucleic acid that are internal to the scaffold (i.e., such regions exclude the most 5' and the most 3' nucleotides of the scaffold).

In some embodiments, a third single-stranded oligonucleotide in the plurality is linked to a third binding partner. In some embodiments, a fourth single-stranded oligonucleotide in the plurality is linked to a fourth binding partner. It is to be understood that the terms first, second, third and fourth, are intended to distinguish between the various binding partners being discussed and are not intended to limit the number, arrangement, or combination of binding partners bound to the scaffold nucleic acid (and thus incorporated into the complex) or to connote the position of the binding partner relative to the other binding partner(s) or to the complex as a whole (e.g., the first oligonucleotide or the first binding partner need not be at the 5' or 3' end of the complex, and rather may be internally located). In some embodiments, the "internal" binding partners may be different between complexes in a plurality. In some embodiments, the internal binding partners may be the same between complexes in a plurality. The internal binding partners may interact with each other or with other moieties in the complex, or they may interact with moieties in the sample.

In some embodiments, the nucleic acid complex may comprise three or more internal binding partners.

In some embodiments, the oligonucleotides of the plurality may be of equal or about equal length. The oligonucleotides may be at least about 20, 30, 40, 50, 60, 70, 80, 90, 100, 110, 120, or more nucleotides in length. The complexity of the plurality of oligonucleotides (i.e., the number of different oligonucleotides in the plurality) will depend in part on the length of the oligonucleotides. In some embodiments, the plurality will consist of at least 20, 30, 40, 50, 60, 70, 80, 90, 100, 110, 120, 130, 140, 150, or more different oligonucleotides. In some embodiments, the single-stranded oligonucleotides are about 60 nucleotides in length.

In various aspects and embodiments described herein, the scaffold nucleic acid is the single-stranded M13 bacteriophage genome.

Also provided herein is a method comprising placing a nucleic acid complex comprising a first and a second binding partner and a third and a fourth binding partner under conditions that allow for binding of the first and second binding partners to each other and the third and fourth binding partners to each other, and detecting binding or a change in binding between the first and second binding partners and/or between the third and fourth binding partners using gel electrophoresis, wherein binding of the first and second binding partners to each other results in formation of a first loop and binding of the third and fourth binding partners to each other results in formation of a second loop, wherein the first and second loop are asymmetric to each other. In this as in other embodiments described herein, the nucleic acid complex comprises a single-stranded scaffold nucleic acid hybridized to a plurality of single-stranded oligonucleotides, wherein a first single-stranded oligonucleotide in the plurality is linked to the first binding partner, a second single-stranded oligonucleotide in the plurality is linked to the second binding partner, a third single-stranded oligonucleotide in the plurality is linked to the third binding partner, and a fourth single-stranded oligonucleotide in the plurality is linked to the fourth binding partner. Binding includes direct binding between two binding partners as well as indirect binding in which two binding partners bind to an intermediate moiety such as an analyte.

Also provided is a method comprising placing a nucleic acid complex comprising first, second and third second binding partners under conditions that allow for binding of the first and third binding partners to each other and/or binding of the second and third binding partners to each other, and detecting binding or a change in binding between the first and third binding partners and/or between the second and third binding partners using gel electrophoresis, wherein binding of the first and third binding partners to each other results in formation of a first loop and binding of the second and third binding partners to each other results in formation of a second loop, wherein the first and second loop are asymmetric to each other. The nucleic acid complex comprises a single-stranded scaffold nucleic acid hybridized to a plurality of single-stranded oligonucleotides, wherein a first single-stranded oligonucleotide in the plurality is linked to the first binding partner, a second single-stranded oligonucleotide in the plurality is linked to the second binding partner, and a third single-stranded oligonucleotide in the plurality is linked to the third binding partner.

Also provided is a method comprising determining two or more molecular interactions by detecting topological changes in a nucleic acid complex that comprises a single-stranded scaffold nucleic acid hybridized to a plurality of single-stranded oligonucleotides, wherein three or more binding partners are separately linked to single-stranded oligonucleotides, using gel electrophoresis, wherein the complex assumes a distinct topology for each molecular interaction.

Also provided is use of a nucleic acid complex comprising a single-stranded scaffold nucleic acid hybridized to a plurality of single-stranded oligonucleotides, wherein a first single-stranded oligonucleotide in the plurality is linked to a first binding partner, a second single-stranded oligonucleotide in the plurality is linked to a second binding partner, and a third single-stranded oligonucleotide in the plurality is linked to a third binding partner, for measuring association and/or dissociation kinetics between the first and second binding partners and/or between the first and second binding partners.

Also provided is use of a nucleic acid complex comprising a single-stranded scaffold nucleic acid hybridized to a plurality of single-stranded oligonucleotides, for measuring association and/or dissociation kinetics for a plurality of binding pairs, wherein each member of a binding pair is linked to a separate single-stranded oligonucleotide.

Also provided is a nucleic acid complex comprising a single-stranded scaffold nucleic acid hybridized to a plurality of single-stranded oligonucleotides, and wherein a first single-stranded oligonucleotide in the plurality is linked to a first binding partner, a second single-stranded oligonucleotide in the plurality is linked to a second binding partner, and a third single-stranded oligonucleotide in the plurality is linked to a third binding partner, and optionally wherein a fourth single-stranded oligonucleotide in the plurality is linked to a fourth binding partner.

In some embodiments, the first, second, third and fourth binding partners are covalently linked to separate oligonucleotides that are hybridized to a single scaffold nucleic acid.

In some embodiments, the first or second binding partner is a library member, and/or wherein the third or fourth binding partner is a library member.

In some embodiments, the single-stranded oligonucleotides are each about 60 nucleotides in length.

In some embodiments, the binding partners are ligands, antigens, and receptors. In some embodiments, the binding partners are proteins or nucleic acids. In some embodiments, the binding partners are antibodies or antibody fragments.

In some embodiments, the binding pair is comprised of a receptor and a ligand for the receptor. In some embodiments, the binding pair is comprised of two nucleic acids. In some embodiments, the first binding partner and the second binding partner are a binding pair. In some embodiments, the first binding partner is an antibody or an antigen-binding antibody fragment and the second binding partner is an antigen bound by the antibody or the antigen-binding fragment.

In some embodiments, the first binding partner and the second binding partner are identical to each other. In some embodiments, the first and second binding partners have binding affinity for an analyte that is neither the first nor the second binding partner.

In some embodiments, the first single-stranded oligonucleotide and the second single-stranded oligonucleotide are separated from each other by about 1000, 2000, 2500, or 3000 nucleotides.

In some embodiments, the first single-stranded oligonucleotide and the second single-stranded oligonucleotide are located about equi-distant from the center of the scaffold nucleic acid.

Also provided is a composition comprising a plurality of any of the foregoing nucleic acid complexes. In some embodiments, the nucleic acid complexes in the plurality comprise the same binding partners.

Also provided is a composition comprising any of the foregoing nucleic acid complexes, and a solid support. In some embodiments, the nucleic acid complex is linked to the solid support. In some embodiments, the solid support is a bead.

Also provided is a kit comprising a single-stranded scaffold nucleic acid, and a plurality of single-stranded oligonucleotides, and further comprising a first single-stranded oligonucleotide linked to a first binding partner, a second single-stranded oligonucleotide linked to a second binding partner, a third single-stranded oligonucleotide linked to a third binding partner, and optionally a fourth single-stranded oligonucleotide linked to a fourth binding partner.

In some embodiments, the first, second, third and/or fourth single-stranded oligonucleotides are housed separately from the plurality of single-stranded oligonucleotides. In some embodiments, the kit further comprises a solid support. In some embodiments, the solid support is a bead.

Also provided is a method comprising combining any of the foregoing nucleic acid complexes comprising a first and a second binding partner with a sample, under conditions that allow for binding of the first and second binding partners to an analyte that is neither the first nor the second binding partner, and detecting binding of the first and the second binding partners to the analyte, if present in the sample, wherein the analyte is present at an attomolar concentration.

In some embodiments, binding of the first and the second binding partners to the analyte is detected using gel electrophoresis.

In some embodiments, the analyte is early pregnancy factor, and the method is a method of determining pregnancy.

In some embodiments, a binding partner is linked covalently to an oligonucleotide. In some embodiments, a binding partner is linked non-covalently to an oligonucleotide.

In another aspect, the invention provides a composition comprising one or more of any of the foregoing nucleic acid complexes. The plurality may be homogeneous (where all the complexes are identical) or it may be heterogeneous (where at least one complex is different from the others).

In another aspect, the invention provides a kit comprising a single-stranded scaffold nucleic acid, and a plurality of single-stranded oligonucleotides, each having a sequence complementary to a sequence on the scaffold nucleic acid, wherein when the oligonucleotides are hybridized to the scaffold nucleic acid no overlap exists between the oligonucleotides.

In some embodiments, the kit comprises oligos 001-121, as provided in FIG. 1A. In some embodiments, the kit comprises oligos 001A, 002-120 and 121A as provided in FIG. 1A. In some embodiments, the kit further comprises a solid support, such as but not limited to a bead (e.g., a magnetic bead).

In some embodiments, one or both binding partners are known. In some embodiments, one binding partner is a member of a library of putative binding partners and the method is intended as a screening method to identify binding partners with affinity for a particular target (i.e., the other binding partner) or as a comparison of a plurality of putative or known binding partners based on affinity. Accordingly, in some embodiments, the binding partners are known to have affinity for each other, while in other embodiments, it may not be known a priori whether they have affinity for each other, or the degree of affinity (i.e., the binding strength) in a given pair may not be known.

These and other aspects and embodiments of the invention will be described in greater detail herein.

BRIEF DESCRIPTION OF DRAWINGS

FIG. 1A. Sequences of all oligonucleotides used. The numbered oligonucleotides cover the entire sequence of the M13 scaffold strand, and the lettered strands are functionalized or special purpose oligonucleotides. The bridge oligonucleotides are labeled red for regions that bind M13 bases 1950-1980, green for regions that bind starting at M13 base 2580, and blue for regions that bind starting at M13 base 4560. Oligonucleotides numbers 001-121 (corresponding to SEQ ID NOs. 1-121) are those used to form the nucleic acid complexes of the invention. These oligonucleotides span the entire length of the M13 template. The nucleotide sequence of the M13 template can be found in US Patent Application Publication 20070117109 and in Rothemund P. W. K. (2006) Nature 440: 297-302. Oligonucleotide numbers 000A, 001A, 033A, 044A and 121A correspond to SEQ ID NOs. 122-126, respectively. Oligonucleotide numbers 033-044A-D and 033-077A-D correspond to SEQ ID NOs. 127-134, respectively.

FIG. 9: Kinetic measurements using DNA nanoswitches. a) The two states of the DNA nanoswitches can be distinguished by gel electrophoresis. b) With two integrated biotins, loop formation begins when unlabeled streptavidin is introduced, and progresses over time as evidenced by increasing brightness in the bound (looped) band across different lanes of a gel. The growth curve is fit with a kinetic model to determine the on rate. c) Addition of excess biotin blocks loop formation, making bond rupture irreversible, which leads to the exponential decay of nanoswitches from the bound state into the unbound state. d) Temperature dependence of on rates and off rates at 150 mM NaCl. Horizontal error bars represent uncertainty in mixing time (±2 seconds), and vertical error bars indicate ±7% uncertainty in the intensity (this is the one-sigma confidence interval determined from 48 repeated measurements of the same construct).

FIG. 10. Various biological measurements using the nanoswitch platform. Schematic representation of each measurement, with data and model fit shown beneath. a) Disulfide bond reduction in 10 µM TCEP at room temperature (koff=2.6±0.4 weeks). b) Biotin-streptavidin dissociation in 300 mM NaCl at room temperature (koff=6.8±0.8 days). c) Dissociation kinetics of digoxigenin and its antibody at room temperature (koff=18.5±2.0 hours). d) Melting kinetics of a 20 nt oligonucleotide at 50° C. (koff=18±1.6 hours). e) Sortase-catalyzed transpeptidation at room temperature (kligation=11±1.3 min). f) XhoI restriction-enzyme kinetics at room temperature (kcut=48±2 sec). Each value is reported as an error-weighted fit parameter ±its one-sigma confidence interval).

FIG. 11. Multistate kinetic analysis. a) A nanoswitch functionalized with two digoxigenin molecules and one biotin molecule can adopt 5 discernable states upon addition of a bispecific receptor. All 5 topological states, A-E, can be resolved within a single lane of an agarose gel. These bands can be fit globally with a single fit of a sum of skewed Gaussian curves. The black curve represents the median pixel intensity, the dashed red curve represents the fit which is the sum of 5 skewed Gaussians, and the individual skewed Gaussians are shaded by state. b) A reaction diagram illustrating the possible transitions between each of the 5 states. c) (left) on-rate measurements indicating the value of each state at 20 different time points. Solid curves indicate the result of a global fit of all states to the kinetic model illustrated in c. (right) off-rate measurements indicating the value of each state at 12 different time points. Solid curves indicate the result of a global fit of all states to the kinetic model illustrated in b. These fits taken together allowed for the determination of all rate constants from 32 lanes which can be run on a single gel. Error bars are based on one-sigma confidence-intervals of the least squares fit to each band. The on-rate model was fit using 100 measurements while the off-rate model was fit using 60 measurements.

FIG. 12. DNA nanoswitch analyte detection platform schematic. Functionalized DNA undergoes a conformational change in the presence of the target analyte. The band locations, and signal per-molecule are constant and largely independent of the size of the analyte of interest. The scenarios provided in A-C have been verified with seven different interacting molecular pairs.

DETAILED DESCRIPTION

The invention relates broadly to nucleic acid based complexes comprising double-stranded nucleic acid and one or more various types of binding partners for targets of interest. Also provided are methods of using such complexes to determine kinetics of binding interactions, such as on- and/or off-rates, to determine affinities of binding interactions, to identify new binding partners for targets of interest, to detect one or more targets in a sample, and to encrypt and decrypt messages, among other things.

The invention provides in part a single-molecule attachment technique that facilitates reliable and accurate single-molecule force measurements. Using DNA self-assembly techniques, a unique linker has been nano-engineered that behaves as a force-activated single-molecule switch. This switch changes conformation under force to signify bond rupture, providing an identifiable molecular signature that distinguishes between the presence and absence of a binding interaction between binding partners, thereby eliminating the possibility of accidentally measuring nonspecific, multiple and unknown interactions. Furthermore, this construct enables the same pair of binding partners to be brought back together following rupture, opening the way to at least high-throughput serial measurements, single-molecule on-rate and off-rates determination, analysis of population heterogeneity, and identification of new binding partners for targets of interest. The approach provided herein is simple, versatile and modular, and can be easily implemented using standard commercial reagents and laboratory equipment.

Also presented herein in various aspects are applications and methods that utilize the linker construct to measure chemical kinetics and force-dependent kinetics of molecular interactions, to detect the presence of molecules and reagents, to screen collections of molecules for particular targets of interest, and to encrypt and decrypt information, inter alia.

Figure 2A:
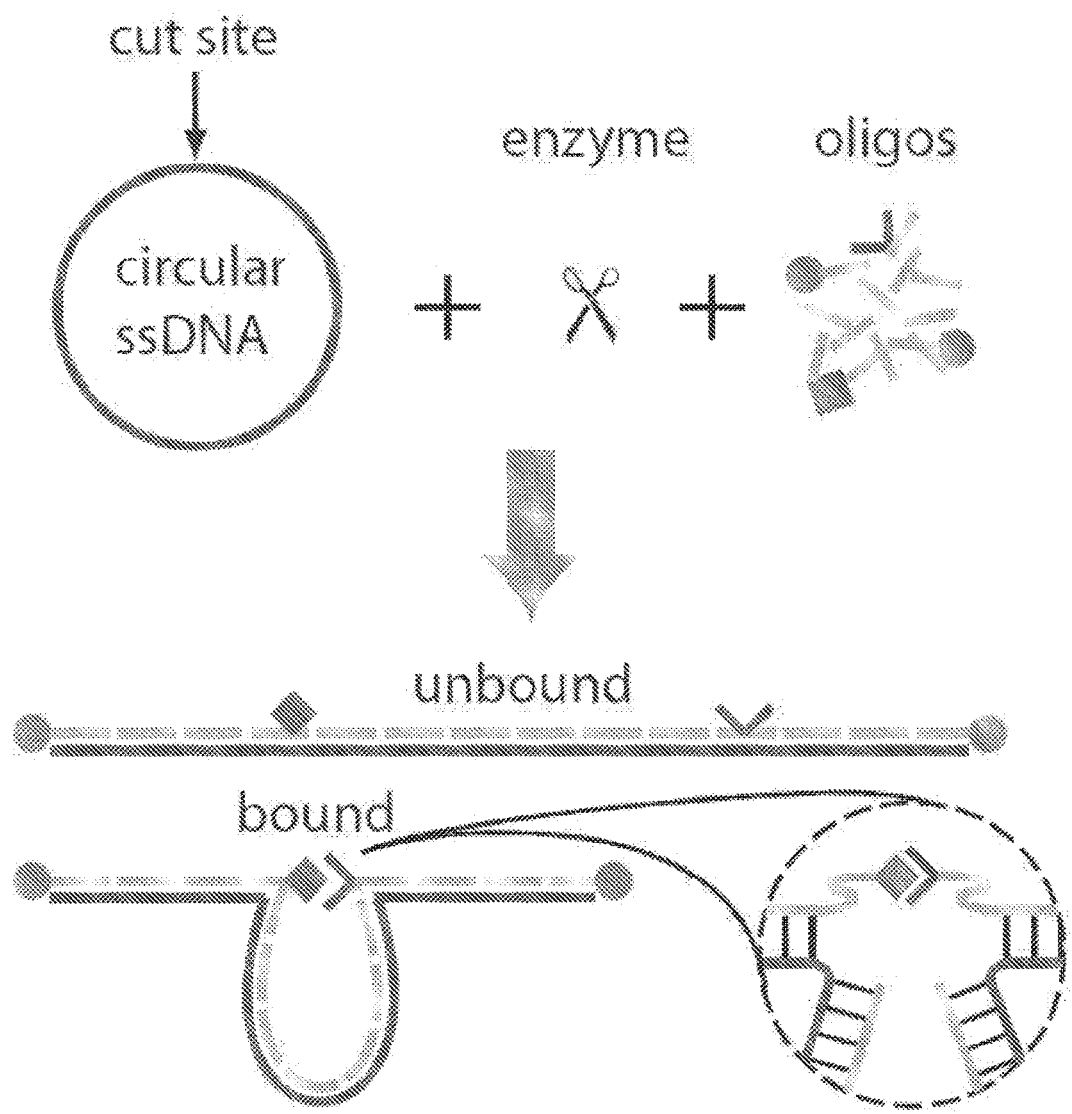
FIG. 2A. Looped linker construction using DNA origami: circular single-stranded DNA is enzymatically cleaved at a single site and mixed with over 100 oligonucleotides to self-assemble into a looped linker with functional groups.
Figure 2B:
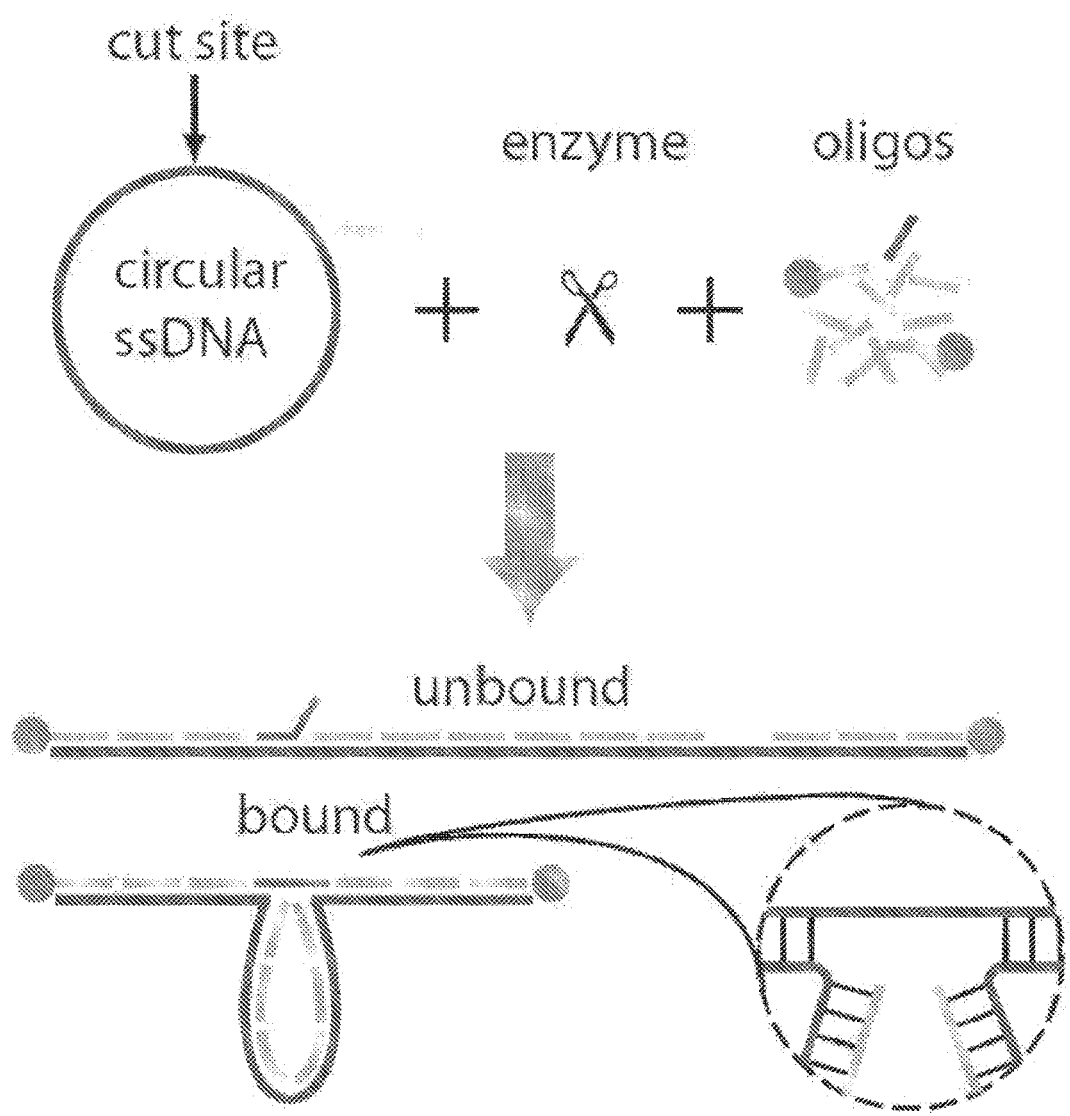
FIG. 2B. Looped linker construction using DNA origami. Circular single-stranded DNA is enzymatically cleaved at a single site and mixed with over 100 oligonucleotides to self-assemble into a looped linker held together by a single "bridge" or "staple" oligonucleotide.

Certain complexes of the invention are constructed using DNA origami methods (Rothemund P. W. K. (2006) Nature 440: 297-302; Douglas S. M. et al. (2009) Nature 459: 414-8). By mixing a long piece of single-stranded DNA with a carefully designed mixture of oligonucleotides, looped single-molecule linkers are constructed via DNA self-assembly. In some embodiments, the complexes comprise an integrated binding pair (e.g., a receptor-ligand pair) (for example, FIG. 2A). As used herein, the terms linker and complex are used interchangeably.

Certain complexes (or linkers) of the invention are each comprised of a single "scaffold" nucleic acid and a plurality of oligonucleotides hybridized thereto. The scaffold nucleic acid and the oligonucleotides are single-stranded prior to hybridization to each other. Accordingly, the scaffold nucleic acid and the oligonucleotides may be referred to herein as being "single-stranded" and it is to be understood that this refers to their state prior to such hybridization.

The invention refers to the scaffold nucleic acid hybridized to a plurality of oligonucleotides as a nucleic acid complex. Such complexes may be at least 50%, at least 60%, at least 70%, at least 80%, at least 90%, at least 95%, at least 96%, at least 97%, at least 98%, at least 99%, or 100% double-stranded. In some embodiments, they are at least 80% double stranded. The complexes of the invention may therefore comprise double-stranded and single-stranded regions. As used herein, a double-stranded region is a region in which all nucleotides on the scaffold are hybridized to their complementary nucleotides on the oligonucleotide. These double-stranded regions may comprise "single-stranded nicks" as the hybridized oligonucleotides are not ligated to each other. The single-stranded regions are scaffold sequences that are not hybridized to oligonucleotides. The invention contemplates the use of complexes having one or more single-stranded regions in between double-stranded regions (typically as a result of unhybridized nucleotides in between adjacent hybridized oligonucleotides).

In some instances, the nucleic acid complex is formed by first hybridizing unmodified (or fixed) oligonucleotides to the scaffold nucleic acid to form a nucleic acid complex intermediate, and then hybridizing modified (or variable) oligonucleotides to the scaffold nucleic acid to form the nucleic acid complex. The modified oligonucleotides may be combined with (and typically hybridized to) the scaffold simultaneously or sequentially. As used herein, a nucleic acid complex intermediate refers to a scaffold that is hybridized to some but not the entire complement of oligonucleotides that is designed to bind to the entire length of the scaffold.

The scaffold nucleic acid may be of any length sufficient to allow association (i.e., binding) and dissociation (i.e., unbinding) of binding partners to occur, to be detected, and to be distinguished from other events. In some instances, the scaffold nucleic acid is at least 1000 nucleotides in length, and it may be as long as 20,000 nucleotides in length (or it may be longer).

The scaffold nucleic acid may therefore be 1000-20,000 nucleotides in length, 2000-15,000 nucleotides in length, 5000-12,000 in length, or any range therebetween. The scaffold may be a naturally occurring nucleic acid (e.g., M13 scaffolds such as M13mp18). M13 scaffolds are disclosed by Rothemund 2006 Nature 440:297-302, the teachings of which are incorporated by reference herein. In some embodiments, including those involving a gel electrophoresis readout, the scaffold nucleic acid may be at least 40, at least 50, at least 60, at least 70, at least 80, at least 90, at least 100, at least 200, at least 300, at least 400, at least 500, at least 600, at least 700, at least 800, or at least 900 nucleotides in length. The scaffold nucleic acid may therefore be 100-1000 nucleotides in length, or 100-300 nucleotides in length, without limitation. In some embodiments, the scaffold is about or less than 200 nucleotides in length. In some embodiments, the scaffold and oligonucleotides are chosen and the binding partners are positioned to yield loops of about 40-100 base pairs. The scaffold nucleic acid may also be non-naturally occurring nucleic acids such as polymerase chain reaction (PCR)-generated nucleic acids, rolling circle amplification (RCA)-generated nucleic acids, etc. It is important that the scaffold nucleic acid is rendered single-stranded either during or post synthesis. Methods for generating a single-stranded scaffold include asymmetric PCR. Alternatively, double-stranded nucleic acids may be subjected to strand separation techniques in order to obtain the single-stranded scaffold nucleic acids. The scaffold nucleic acid may comprise DNA, RNA, DNA analogs, RNA analogs, or a combination thereof, provided it is able to hybridize in a sequence-specific and non-overlapping manner to the oligonucleotides. In some instances, the scaffold nucleic acid is a DNA.

The scaffold nucleic acid is hybridized to a plurality of oligonucleotides. Each of the plurality of oligonucleotides is able to hybridize to the scaffold nucleic acid in a sequence-specific and non-overlapping manner (i.e., each oligonucleotide hybridizes to a distinct sequence in the scaffold). The complex may comprise varying lengths of double-stranded regions. As a non-limiting example, 90% or more, including 95%, 96%, 97%, 98%, 99% and 100% of the scaffold nucleic acid may be hybridized to oligonucleotides. It is to be understood that the scaffold may also comprise a plurality of nicks that are typically located between bound oligonucleotides. The length and the number of oligonucleotides used may vary. It will be understood that the greater the length of the oligonucleotides, the fewer that will be needed to hybridize to the scaffold nucleic acid. In some instances, the length and sequence of the oligonucleotides is chosen so that each oligonucleotide is bound to the scaffold nucleic acid at a similar strength. This is important if a single condition is used to hybridize a plurality of oligonucleotides to the scaffold nucleic acid. In some instances, the oligonucleotides are designed to be of approximately equal length. The oligonucleotides may be about 10, about 15, about 20, about 30, about 40, about 50, about 60, about 70, about 80, about 90 or about 100 nucleotides in length. The number of oligonucleotides in the plurality may be about 50, about 60, about 70, about 80, about 90, about 100, about 110, about 120, about 130, about 140, about 150, about 160, about 170, about 180, about 190, or about 200, without limitation.

The number of oligonucleotides hybridized to a particular scaffold may vary depending on the application. Accordingly, there may be 2 or more oligonucleotides hybridized to the scaffold, including 3, 4, 5, 6, 7, 8, 9, 10, 20, 30, 40, 50, 60, 70, 80, 90, 100, 200, 300, 400, 500, 600, 700, 800, 900, or 1000 or more oligonucleotides. It will be understood that the number of oligonucleotides will depend in part on the application, the length of the scaffold, and the length of the oligonucleotides themselves.

According to the invention, certain of the oligonucleotides hybridized to the scaffold nucleic acid will be unmodified. Unmodified oligonucleotides include oligonucleotides that are not linked to binding partners such as the binding partners that the linkers are designed to test (e.g., an antibody or an antigen) and the binding partners used to immobilize the linker onto a solid support such as but not limited to a bead (e.g., biotin). The majority of oligonucleotides hybridized to a scaffold nucleic acid may be unmodified. Unmodified oligonucleotides may be referred to herein as "fixed" oligonucleotides.

Other oligonucleotides hybridized to the scaffold may be modified. Modified oligonucleotides include those that are linked to binding partners that the linkers are designed to test (e.g., a receptor and/or its ligand, an antibody and/or its antigen, etc.). Modified oligonucleotides also include those that are modified and thus used to immobilize the complex (or linker) onto a solid support such as but not limited to a bead. Such modified oligonucleotides including biotinylated oligonucleotides. Modified oligonucleotides may be referred to herein as "variable" oligonucleotides since these oligonucleotides may be modified by linking to a variety of binding partners depending on the method of use.

Regions comprising scaffold hybridized to unmodified oligonucleotides may be referred to herein as "fixed" regions. Regions comprising scaffold hybridized to modified oligonucleotides may be referred to herein as "variable" regions.

The spacing of modified (or variable) oligonucleotides along the length of the scaffold nucleic acid may vary. In some embodiments, the nucleic acid complex may comprise three or four variable regions (e.g., three or four modified oligonucleotides). As an example, a nucleic acid complex may comprise modified oligonucleotides at one or both of its ends as well as two internal modified oligonucleotides. The modified oligonucleotides at the ends of the complex may be used to immobilize the complex to a solid support such as a bead. The modified oligonucleotides internal to the complex may be linked individually to members of a binding pair (i.e., each of the two oligonucleotides is linked to a member of the binding pair such that the complex comprises the binding pair, with each member of the pair on a different oligonucleotide). The internal modified oligonucleotides may be symmetrically or quasi-symmetrically located around the center of the linker. In other words, they may be positioned equi-distant from the center of the scaffold (or the complex).

In some embodiments, the invention contemplates the use of a plurality of complexes each comprising the same binding pair. The difference between the complexes in the plurality is the distance between the binding pair members (i.e., the binding partners). For example, the plurality may comprise complexes in which the distance between the binding pair members is 300 base pairs, 200 base pairs, 150 base pairs, 100 base pairs, 80 base pairs, 60 base pairs, and 40 base pairs. The complexes are then analyzed for their ability to form looped structures based on interaction between the binding partners. It is expected that as the distance between the binding partners decreases, a greater internal force is exerted on the binding interaction. Accordingly, the binding interaction will continue until the internal force becomes too great and the complex assumes the more energetically favorable linear state. The kinetics and strength of a binding interaction between two binding partners can be analyzed using this approach.

Figure 3A:
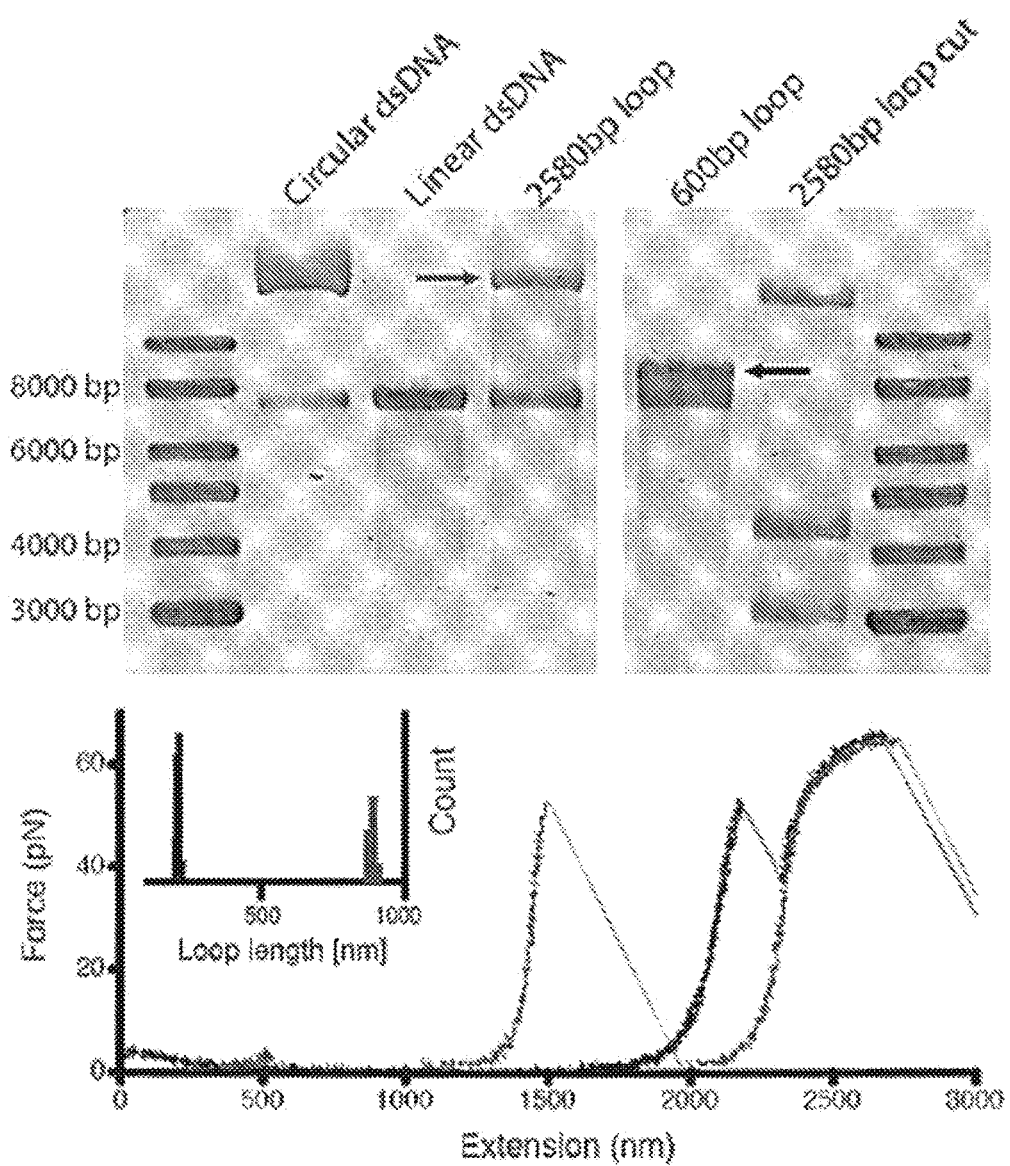
FIG. 3A. Verification of DNA bridge looped linker. Top: gel electrophoresis on a 0.7% agarose gel at 5 V cm-1 for 2 h, stained with SYBR® gold. Bottom: single-molecule pulling trajectories demonstrating the sudden increase in tether length that signifies bond rupture events. The inset shows a histogram of the change in tether length for the 2580 bp (red) and 600 bp (black) looped linkers.

Importantly, the distance between the internal modified oligonucleotides will be used to distinguish association and dissociation between binding partners linked to the complex. This is because when the binding partners are associated with each other, a loop will be formed comprising the double-stranded, nicked nucleic acid sequence that exists between the binding partners. When the binding partners are not associated to each other (i.e., unbound), then the loop does not form and the complex length is different. The complex length may be detected by direct measurements, for example, under tension, as described herein. When measured under tension, the transition from associated to dissociated binding partners is indicated by an increase in length of the complex. The length of the complex, in this and related aspects, intends the shortest distance between the two ends of the complex and is to be distinguished from the apparent length (discussed below) which is determined using gel electrophoresis and the length of the scaffold nucleic acid (which will not change as a result of association and disassociation of a binding pair). When measured using gel electrophoresis, the transition from associated to dissociated binding partners (or vice versa) is indicated by a difference in migration distance through the gel. In some instances, the transition from associated to dissociated binding partners (and thus closed to open states) is indicated by an increase in the migration distance through the gel (e.g., akin to a shorter nucleic acid). As shown in FIG. 3A, a circular scaffold such as circular M13 migrates the slowest, a linearized double-stranded version of M13 (without binding partner association) migrates fastest, and complexes having associated binding partners (i.e., having looped conformations) migrate in between. Importantly, the migration pattern differs based on the length of the loop, with loops that are on the order of about 2590 base pairs clearly distinguishable from loops that are on the order of about 600 base pairs.

The ability to distinguish loops of differing sizes facilitates the use of multiple complexes in a single assay where one or subsets of complexes (all having the same loop size) are specific for a particular analyte in a sample. In these aspects of the invention, the binding partners bound to the complex do not bind to each other but rather bind to the same analyte. Accordingly, in the presence of the analyte a loop is formed while in the absence of the analyte no loop is formed. The looped (or closed or bound) complex migrates to a different degree than does the linear (or open or unbound) complex. Additionally, loops of different sizes can be distinguished from each other and as a result the presence (or absence) of a multiple analytes (each detected by a complex having a loop of a particular size) can be determined simultaneously in a multiplexed assay. Such methods may be used to detect the presence of a single or multiple analytes and may form the basis of a diagnostic assay.

It is to be understood that the invention intends several variations on the nucleic acid complexes described herein. Typically, these variations all commonly comprise a nucleic acid complex having two or more binding partners. The binding partners may have binding specificity for each other or they may have binding specificity for a common analyte. Several of the methods of the invention rely on the association and/or dissociation of binding partners. A change in the complex (e.g., from an open to a closed conformation or from a closed to an open conformation) provides information about the kinetics and strength of the binding interaction. The binding partners may be non-covalently or covalently bound to the complex. Typically, even if the binding partners are not bound to each other, they are nevertheless bound to the nucleic acid complex.

Thus, in a first variation, the nucleic acid complex comprises two binding partners having binding specificity for each other. The binding partners are physically separate and thus spaced apart from each other along the length of the complex (i.e., when not bound to each other). When bound to each other, the nucleic acid complex assumes a looped (or closed or bound) conformation having a different length, including a different apparent length, compared to the nucleic acid complex in an open (or unbound) conformation.

In another variation, the nucleic acid complex comprises two binding partners having binding specificity for a common analyte. The binding partners are physically separate and thus spaced apart from each other (when not bound to the common analyte). When bound to the common analyte, the nucleic acid complex assumes a looped (or closed or bound) conformation having a different length, including a different apparent length, compared to the nucleic acid complex in an open (or unbound) conformation.

The invention further contemplates that a nucleic complex may comprise more than two linked binding partners. The number of binding partners may be 2, 4 or more. In some embodiments, pairs of binding partners are provided, with each pair having binding specificity for each other (i.e., rather than binding specificity for a common analyte). The location or arrangement of the binding partners may vary and may include serially positioned binding pairs or nested binding pairs, or combinations thereof. As an example, assume that A1 and A2 are a binding pair (e.g., first and second binding partners) and B1 and B2 are a different binding pair (e.g., third and fourth binding partners), then these may be arranged as 5'-A1-A2-B1-B2-3', or they may be arranged as 5'-A1-B1-B2-A2-3'.

The invention further contemplates that the binding partners in a pair may be both known, or one may be known and the other may be unknown. As an example of the latter instance, one binding partner may be a known moiety (e.g., a receptor) and the other binding partner may be a member of a library that is being screened for its binding affinity to the known moiety. The library may be an aptamer library and the member that binds with sufficient affinity to the known moiety may be identified by isolating the complex from a gel electrophoresis band, amplifying and sequencing.

In a second variation, the nucleic acid complex is used together with a non-covalently bound nucleic acid (e.g., a bridge oligonucleotide) that hybridizes to two non-contiguous regions of the scaffold nucleic acid, thereby creating a looped conformation in the nucleic acid complex.

The invention contemplates that a single complex may be used together with 1, 2 or more bridge oligonucleotides. As an example, assume that A1 and A2 are the two non-contiguous regions to which a first bridge oligonucleotide binds and B1 and B2 are the two non-contiguous regions to which a second bridge oligonucleotide binds, then these regions may be arranged as 5'-A1-A2-B1-B2-3', or they may be arranged as 5' A1-B1-B2-A2-3'.

The invention contemplates that oligonucleotides bearing binding partners of a binding pair (or alternatively non-contiguous regions to which a bridge oligonucleotide may bind) may be located internally within the complex or they may be located at or near the terminal ends of the nucleic acid complex. Accordingly, in some instances, the oligonucleotide that is most 5' on the complex and the oligonucleotide that is the most 3' on the complex may each be linked to a member of a binding pair (e.g., first and second binding partners having affinity for each other). In similar embodiments, the 5' and/or 3' penultimate oligonucleotides in the complex may each be linked to a member of a binding pair. In these embodiments, the association of the binding partners will circularize or nearly circularize the complex. In these embodiments, the oligonucleotides linked to binding partners may or may not be additionally linked to another moiety such as an immobilization moiety such as biotin (see below). Transitions between associated and dissociated binding partners (and thus closed and open conformations, respectively) may be detected in a variety of ways including but not limited to gel electrophoresis. When gel electrophoresis is used, a transition from closed to open conformations (and vice versa) may be determined by a change in migration distance. Other ways of detecting transition between closed and open conformations (and vice versa) include but are not limited to optical tweezers, magnetic tweezers, tethered particle motion, a centrifuge force microscope as described in published PCT patent application WO2011/153211, atomic force microscopy (AFM), and light microscopy. As an example, if optical tweezers are used, the complex can be designed such that the most 3' oligonucleotide could be linked to one substrate (such as a bead) and the most 5' oligonucleotide could be linked to another substrate (such as a glass coverslip). Changes in length resulting from a change in binding between binding partners can be observed as a change in distance between the two substrates (e.g., between the bead and the coverslip). It is to be understood that the invention contemplates measuring binding changes (and thus changes in length of the complex) in the presence of an external force (e.g., under tension) or in the absence of such force. Still other approaches contemplated by the invention include directly detecting changes in length using single molecule fluorescence imaging, detecting changes in the average rheological properties of a solution of the complexes of the invention, and monitoring changes in hydrodynamic radius using dynamic light scattering.

The invention further contemplates the use of a DNA crosslinking agent to increase the strength of the complex. DNA crosslinking agents are known in the art and include without limitation psoralen. The complexes may also be exposed to crosslinking irradiation. In some embodiments, the crosslinked complexes may less likely to dissociate themselves when under tension or under other conditions that are intended to test the affinity of binding partners linked thereto. In still other instances, the invention contemplates crosslinking amino acid based moieties such as certain binding partners (e.g., to the complex). Protein crosslinking agents are known in the art and include without limitation NHS-diazirine (SDA).

The invention also contemplates labeling of the nucleic acid complex, the scaffold nucleic acid, any of the plurality of oligonucleotides, and/or the binding partners linked thereto. Labeling intends that any of these components are linked to a moiety that may be used to immobilize (permanently or transiently), detect, manipulate and/or modify. Moieties that are used to immobilize are described herein, are known in the art, and include without limitation biotin and avidin or derivatives thereof. Moieties that are used to detect are often times referred to as detectable moieties. Such moieties are also known in the art, and they include without limitation fluorophores, chromophores, radioisotopes, magnetic particles, enzyme substrates, and the like.

The complexes of the invention, in some instances, comprise oligonucleotides that are linked to a binding partner such as for example an antibody or an antigen (and may be referred to herein as modified oligonucleotides). The linkage between the oligonucleotide and the binding partner may be covalent or non-covalent depending on the strength of binding required for a particular application. These modified oligonucleotides may be generated by first incorporating a reactive group (or moiety) into the oligonucleotide, preferably at or near one of its ends, and then reacting this group (or moiety) with the binding partner of interest which may or may not be modified itself. An example of such a conjugation protocol is provided herein. Suitable reactive groups are known in the art. Examples of reactive groups that can covalently conjugate to other reactive groups (leading to an irreversible conjugation) include but are not limited to amine groups (which react to, for example, esters to produce amides), carboxylic acids, amides, carbonyls (such as aldehydes, ketones, acyl chlorides, carboxylic acids, esters and amides) and alcohols. Those of ordinary skill in the art will be familiar with other "covalent" reactive groups. Examples of reactive groups that non-covalently conjugate to other molecules (leading to a reversible conjugation) include biotin and avidin or streptavidin reactive groups (which react with each other), antibody (or antibody fragment) reactive groups and antigens, receptors and receptor ligands, aptamers and aptamer ligands, nucleic acids and their complements, and the like. Virtually any reactive group is amenable to the methods of the invention, provided it participates in an interaction of sufficient affinity to prevent dissociation of the binding partner from its oligonucleotide.

It is to be understood that the scaffold nucleic acid and the oligonucleotides of the invention may be DNA or RNA in nature, or some combination thereof, or some analog or derivative thereof. The term nucleic acid refers to a polymeric form of nucleotides of any length, including deoxyribonucleotides, ribonucleotides, or analogs thereof. In some embodiments, the nucleic acids will be DNA in nature, and may optionally comprise modifications at their 5' end and/or their 3' end.

In some embodiments, the binding partners may include without limitation antibodies (or antibody fragments) and antigens, receptors and ligands, aptamers and aptamer receptors, nucleic acids and their complements, and the like.

Methods of Use

The nucleic acid complexes of the invention, including single-molecule linkers or complexes, can be used in myriad applications, including for example, measuring the kinetics of molecular interactions, identifying molecular binding partners (from a known or unknown candidates), and encrypting and decrypting information. Various additional aspects of the invention are described below.

Various methods of the invention detect changes in binding based on a change in length of the complex. As described herein, changes in length may be measuring using any number of methods including but not limited to gel electrophoresis, single molecule force probes such as optical tweezers, magnetic tweezers, tethered particle motion, atomic force microscope (AFM), centrifuge force microscopy (CFM), and single molecule fluorescence imaging.

Competitive binding assays to measure molecular/chemical kinetics. Some aspects of the invention provide methods of measuring the kinetics of molecular interactions using the nucleic acid complexes described herein. As described above, a nucleic acid complex can exist in one of two conformational states: bound or unbound. These conformational states may be referred to as closed and open, respectively. As an example, a nucleic acid complex that comprises a pair of binding partners having specificity to each other (e.g., ligand and receptor) is in its open state if the binding partners do not bind to each other and the scaffold nucleic acid remains linear. A nucleic acid complex is in its closed state if the binding partners bind to each other and the scaffold nucleic acid forms a looped conformation. By monitoring the change in these states, the kinetics of the binding interaction between the binding partners can be determined. In some embodiments, the conformational state can be resolved on an electrophoretic gel, as described elsewhere herein. In other embodiments, the conformational state can be resolved using single-molecule force probes, including but not limited to optical tweezers, magnetic tweezers, tethered particle motion, atomic force microscopy (AFM), centrifuge force microscope (CFM). In other embodiments, the conformational state can be observed directly using single-molecule fluorescence imaging.

The following protocol can be used to measure the kinetics (e.g., off-rate) of molecular binding partners on a linker: 1) providing a nucleic acid complex that comprises two binding partners (e.g., A and A') bound to each other (i.e., in a closed conformation), 2) add excess of a soluble form of one binding partner (A) that will bind to its binding complement (A') when the A-A' bound to the complex dissociate from each other, essentially fixing the dissociated complex in an open conformation, 3) determine the conformational state of the complexes over a period of time in order to determine the off-rate of the A-A' interaction. With time, the closed conformation will convert to the open conformation. The rate at which that conversion occurs is an indicator of the strength of binding between those binding partners. The soluble form of the binding partner (A) may be present at a 2-fold, 3-fold, 5-fold, 10-fold, 50-fold, 100-fold, or more excess over the amount (or concentration) of the complex-bound form of the binding partner (A).

Figure 7D:
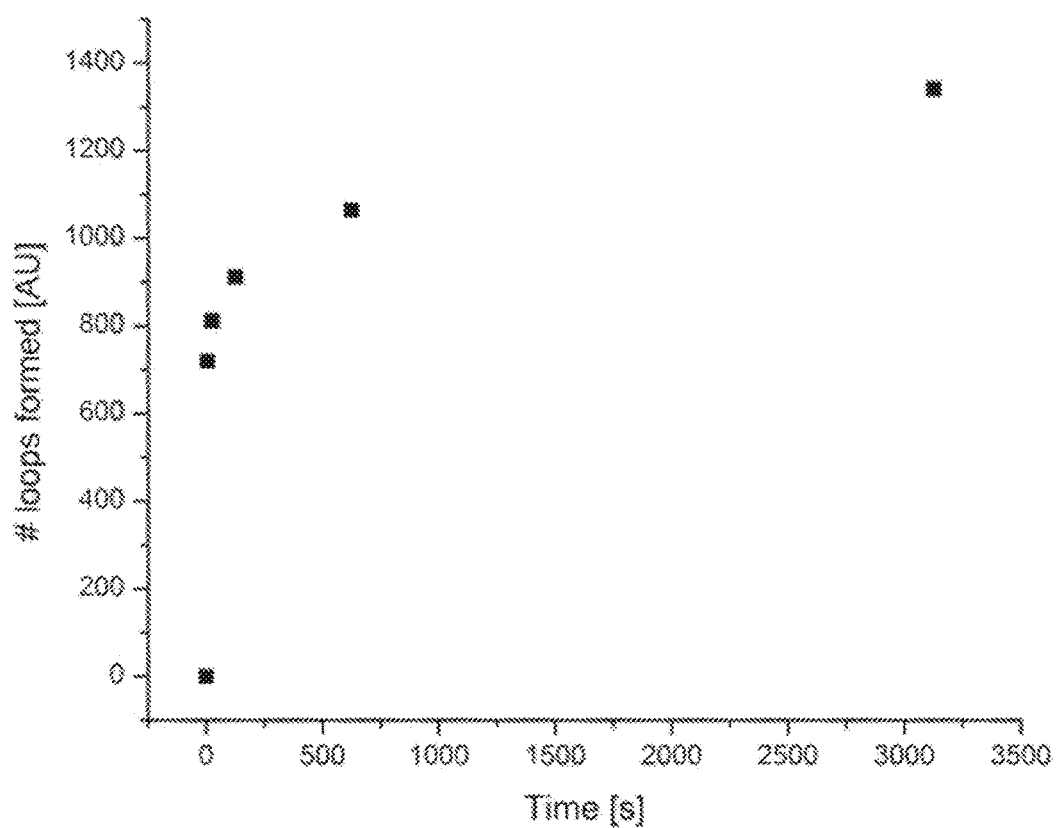
FIG. 7. Demonstration of molecular kinetics with a nanoswitch. (A) The DNA nanoswitch has two distinct states, depending on the binding of a receptor-ligand pair, that can be distinguished by gel electrophoresis, (B) In the presence of excess ligand, a nanoswitch in the bound state will become trapped in the unbound state upon dissociation. (C) Dissociation of biotin-streptavidin at 50° C. and 150 mM NaCl causes the amount of looped product to decrease over time (see gel image). The amount of looped construct is quantified from the gel to determine the kinetics of dissociation. (D) Looped constructs comprising two biotin oligos were made in the presence of streptavidin (t=0), followed by quenching in the presence of excess biotin at various time. These data can be used to determine on-rate and dissociation constant Kd.
Figure 8:
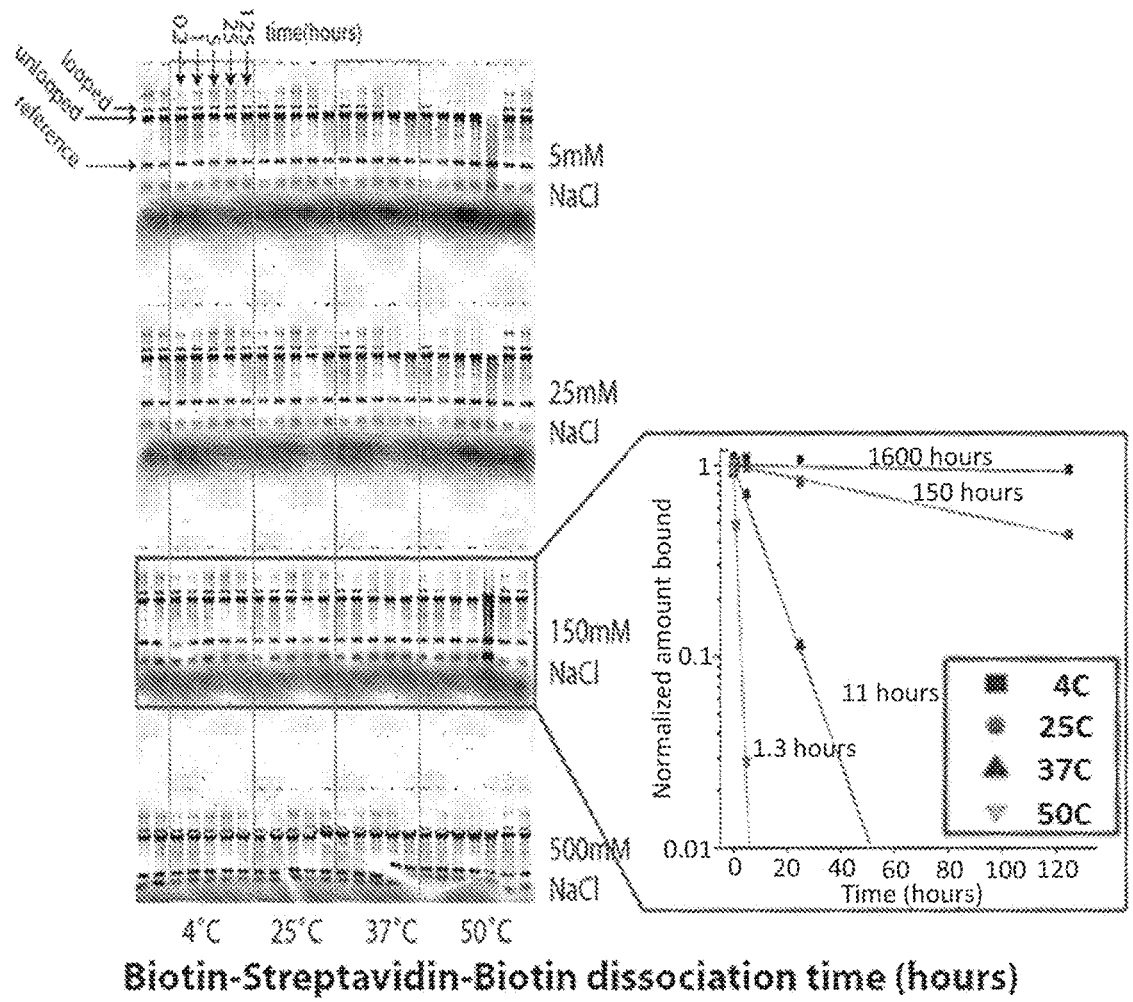
FIG. 8. Biotin-Streptavidin-Biotin dissociation kinetics. An array of 16 different experimental conditions were tested on a single 96-well gel. Each of four combs has a different salt, and within each comb are experiments at four temperatures. Dissociation was measured at 5 different times: 0.2, 1, 5, 25, and 125 hours. An expanded view of one salt condition shows widely varying off-rates with temperature. The resulting data are summarized in the table, showing time constants ranging from less than 1 hour to over 1000 hours.

FIGS. 7 and 8 demonstrate the formation of looped constructs. FIG. 7D, for example, illustrates the formation of looped constructs having two biotins in the presence of streptavidin (t=0). Excess biotin was added at various times in order to quench the re-formation of looped constructs following their natural dissociation under the particular conditions. These data can be used to determine the on-rate, and thus also the dissociation constant Kd, of binding pairs such as biotin and streptavidin. Preliminary analysis of these particular data yields a Kd on the order of $10^{-14}$, which is the same as reported in the literature.

Figure 6A:
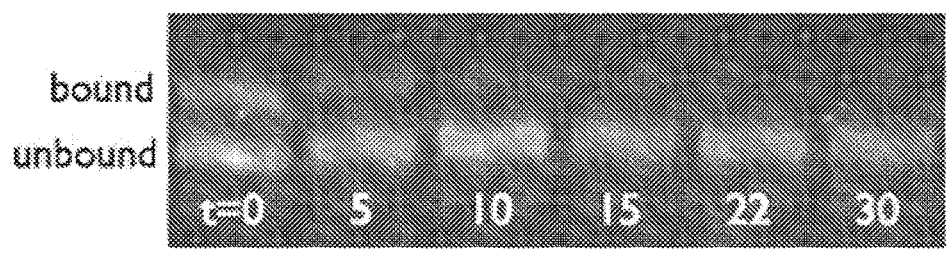
FIG. 6. (A) is a photograph of an electrophoretic gel showing the bound and unbound conformations in the presence of psoralen at various times. (B) is a graph of the fraction of complex that is bound (or looped) as a function of time. (C) is a photograph of an electrophoretic gel showing the closed conformation of a complex comprising digoxin and anti-digoxigenin binding partners (left lane) and the loss of the closed conformation upon addition of excess anti-digoxigenin antibody.
Figure 6B:
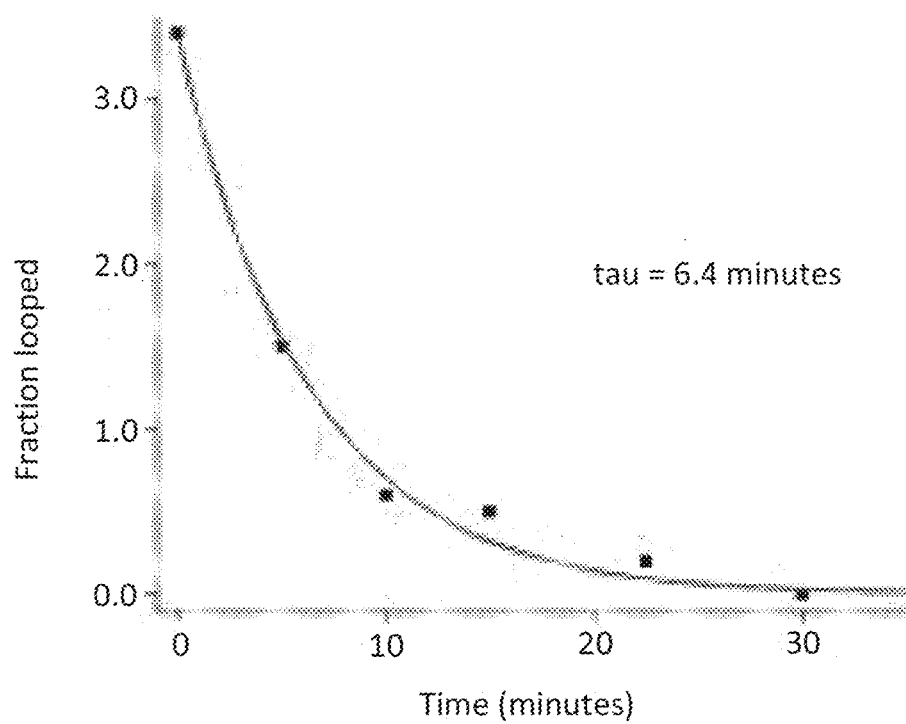

FIGS. 6A and B show the results of an assay using an excess of bridge oligonucleotide. The excess bridge oligonucleotide competes with the hybridized bridge oligonucleotide for binding to the complex. This experiment was carried out at elevated temperature in order to accelerate the kinetics. The bridge oligonucleotide was 50 nucleotides in length. The competition assay could also be carried out using excess oligonucleotide that is complementary to the bridge oligonucleotide.

Figure 6C:
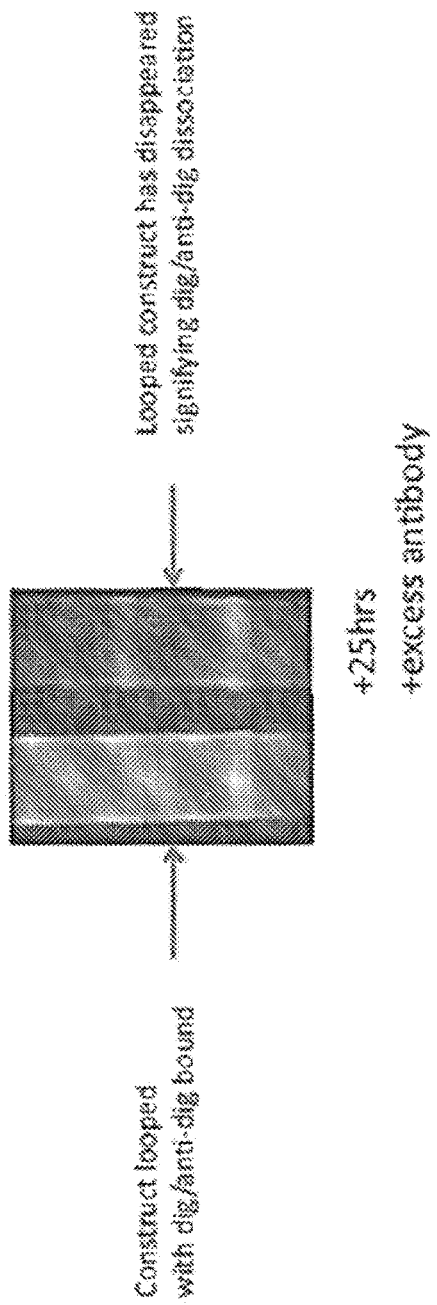

FIG. 6C shows the results of an assay using an excess of antibody. In this assay, the binding partners bound to the complex are digoxin and anti-digoxigenin antibody. In the absence of excess anti-digoxigenin antibody, the closed complex is formed, as shown by the presence of a band in FIG. 6C (left lane). In the presence of excess anti-digoxigenin antibody, the complex converts to an open state as indicated by the loss of the band corresponding to the closed state, as shown in FIG. 6C (right lane).

In some embodiments, the protocol may include the use a photoactive crosslinker such as psoralen to preserve the complex conformation at different times prior to sampling. Crosslinking provides a "snapshot" of how much of the complex is in a bound/closed state at any given time and may be necessary to preserve the conformation in instances where the kinetics are faster than the gel running time. Other photoactive or non-photoactive crosslinking agents can be used in the methods provided herein.

Internal Mechanical Force as a Measure of Force-Dependent Kinetics.

Some aspects of the invention provide methods of measuring force-dependent kinetics of binding interactions using the nucleic acid complexes described herein by creating a force that is internal to the complex (rather than applying an external force as can be done using optical tweezers or magnetic tweezers, for example). This method takes advantage of "internal" mechanical forces that are created when a double-stranded nucleic acid is circularized. (Shroff et al. Biophysical Society (2008) 94:2179-86) Changing the length of a nucleic acid loop varies the internal force of the complex, with force increasing as the length decreases. For example, binding partners on a scaffold nucleic acid that are separated by approximately 200 to 300 nucleotides will easily bind to form a closed loop configuration because there is very little, if any, internal force created by the loop. On the other hand, the same binding partners when separated by shorter distances will less readily form a closed loop conformation (and when formed, may more readily dissociate) as the force imposed by the scaffold nucleic acid approaches, is similar to, and/or exceeds the binding strength between the binding partners.

The following protocol can be used to measure the force-dependent kinetics of binding partners on a complex: 1) provide a plurality of complexes, each complex within the plurality comprising the same binding partner pair, wherein the number of nucleotides separating the binding partners on a scaffold nucleic acid varies within the plurality, and 2) determine the presence of bound versus unbound complexes as a function of separating distance, using for example gel electrophoresis. It is expected that as the loop length decreases, the ratio of bound to unbound complexes will decrease also. In some embodiments, the protocol may include the use a photoactive crosslinker such as psoralen to "freeze" complex conformation at different times prior to sampling the complexes. Other photoactive or non-photoactive crosslinking agents can be used in the methods provided herein. In some embodiments, the protocol can include the initial formation of a loop that predominantly consists of single-stranded DNA. To generate tension within these loops, oligonucleotides complimentary to portions of the looped scaffold regions are added and allowed to hybridize to the scaffold, thereby generated a mechanical force upon hybridization and formation of double-stranded regions within the loop. The force can be therefore be precisely and finely varied in time and magnitude by varying the amount of double-stranded versus single-stranded nucleic acid in the loop. (Shroff, Liphardt et al., Nano Letters 2005.)

A similar approach may be taken using bridge oligonucleotides. Thus, in some embodiments, a nucleic acid complex comprises a bridge oligonucleotide that hybridizes to two non-contiguous sequences of the scaffold nucleic acid. In embodiments where the bridge oligonucleotides binds to non-contiguous regions of the linker, the distance between the non-contiguous sequences may be varied among the complexes such that the internal force of the closed loop configuration varies, accordingly.

In some embodiments, the number of nucleotides separating the binding partners, or separating the two non-contiguous sequences to which a bridge oligonucleotide binds, is at least 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more nucleotides. In some embodiments, the distance is 40-100 nucleotides. Suitable distances will vary based on the application and will depend on the size of the binding partners, the degree of single- and double-strandedness of the looped region, the use of linkers to attach the binding partners to oligonucleotides within the complex, and the like.

Analyte Detection.

Some aspects of the invention provide methods for detecting the presence of an analyte of interest in a sample using the nucleic acid complexes described herein. In these aspects, the complex comprises two binding partners that have specificity for the same analyte. The binding partners may be identical to each other, provided that they can both bind to the analyte simultaneously. As an example, they may be identical antibodies provided the antigen to which they bind has several epitopes that can be bound by the antibodies simultaneously without interference. The binding partners may be different from each other but have binding affinity for the same analyte. As an example, they may be antibodies that bind to different epitopes on the same antigen provided they can bind to the antigen simultaneously without interference. The bound and unbound conformation of the complex can be used to determine the presence and absence of an analyte in a sample, respectively. If the analyte is present, the binding partners that are attached to the scaffold nucleic acid will bind to the analyte to form a closed loop conformation. In the absence of the analyte, binding will not occur, and the complex will remain open.

The following protocol can be used to detect an analyte in a sample: 1) combine a sample with a complex comprising binding partners of the analyte (e.g., antibodies to the analyte), and 2) determine the conformation of the complex for example by gel electrophoresis. Detection of a closed loop conformation is an indication that the analyte is present in the sample and binds to the two binding partners bound to the scaffold nucleic acid. As described herein, in other embodiments, the conformational state can be resolved using single-molecule force probes, including but not limited to optical tweezers, magnetic tweezers, tethered particle motion, atomic force microscopy (AFM), centrifuge force microscope (CFM). In other embodiments, the conformational state can be observed directly using single-molecule fluorescence imaging.

Screening Methods and Identification of Binding Partners.

Some aspects of the invention provide methods for screening a collection of nucleic acid based binding partners such as but not limited to aptamers for a target binding partner using the nucleic acid complexes described herein. By attaching a known moiety and a candidate binding partner to different regions of the scaffold nucleic acid, and determining whether a looped conformation is formed between the two, a binding partner to the known moiety can be identified. If the candidate binding partner is a true binding partner of the known moiety, then it will bind to the known moiety, and the complex will form a closed loop conformation. If the candidate binding partner has virtually no affinity for the known moiety, the complex will remain open.

The following protocol can be used to screen for binding partners on a complex: 1) provide a collection of complexes that comprise a known moiety (e.g., a target molecule) and a unknown candidate binding partner (e.g., an aptamer from a library of aptamers), and 2) determine the conformation of the complex at one or more times for example by gel electrophoresis. Detection of a closed loop conformation is an indication that the candidate binding partner has affinity for the known moiety. It is also possible to order a number of candidate binding partners based on their degree of affinity for the known moiety. In other embodiments, the conformational state can be resolved using single-molecule force probes, including but not limited to optical tweezers, magnetic tweezers, tethered particle motion, atomic force microscopy (AFM), centrifuge force microscope (CFM). In other embodiments, the conformational state can be observed directly using single-molecule fluorescence imaging.

Force-Measuring Technologies

As discussed herein, various methods of the invention involve detecting interactions between binding partners by detecting changes in length of the nucleic acid complexes. Binding interactions, changes in complex length, transitions from open to closed (or closed to open) conformations, and kinetic modifications, inter alia, may be detected or determined using a number of methodologies including but not limited to gel electrophoresis, atomic force microscopy (AFM), optical tweezers, magnetic tweezers, tethered particle motion, centrifuge force microscopes (CFM), mechanical cantilevers, and the like. These methodologies are known in the art and some are described briefly below. It is to be understood that any of these methodologies can be used in conjunction with the various methods provided herein.

Atomic Force Microscopy.

The force between two binding partners on a linker can be measured by atomic force microscopy (AFM) or scanning force microscopy (SFM). In some embodiments, AFM can be used to measure single molecule linker stretching and rupture forces. In some embodiments, the force measured may be on the order of a few picoNewtons (pN). In some embodiments, AFM is performed with either static or dynamic modes.

Optical Tweezers.

The force between two binding partners on a linker can be measured using optical tweezers (also referred to as a "single-beam gradient force trap"). Optical tweezers use a highly focused laser beam to provide an attractive or repulsive force (typically on the order of pN), depending on the refractive index mismatch, to physically hold and move microscopic dielectric objects, such as nucleic acids. In some embodiments, optical tweezers are used to manipulate a linker by exerting extremely small forces via a highly focused laser beam.

In some embodiments, optical traps can be used to detect nucleic acid displacement as a measure of molecular force. The optical trap may be used herein to manipulate and study single molecule linkers by interacting with a bead that has been attached to the linker.

Magnetic Tweezers.

The force between two binding partners on a linker can be measured using magnetic tweezers (MT). Magnetic tweezers exert force and torque to a molecule such as a nucleic acid complex of the invention. The extension of a molecule corresponds to its response to the applied stress. In some embodiments, a single linker is attached at one end to a tethering surface and at the other to a magnetic microparticle. The magnetic tweezers apparatus is equipped with magnets that are used to manipulate the magnetic particles whose position is measured with a video microscopy.

Centrifuge Force Microscopy.

The force between two binding partners on a linker can be measured using centrifuge force microscopy (CFM). CFM exerts force to a molecule such as a nucleic acid complex of the invention using centrifugal force. The extension of a molecule corresponds to its response to the applied stress. In some embodiments, a complex is attached at one end to a tethering surface and at the other to a particle that can be visualized using for example light microscopy. The position of the particle and its movement relative to the tethering surface may be observed and measured as a function of the centrifugal force applied to the complex.

Other mechanical force-measuring technologies may be used with the embodiments described herein, for example, mechanical cantilevers, and the like.

EXAMPLES

Example 1. Switchable Single Molecular Linkers

Materials and Methods Linker Design and Construction:

All oligonucleotides were purchased from Bioneer, Inc., with the exception of the 5' double-biotin oligonucleotide (Integrated DNA Technologies), the digoxigenin oligonucleotides (Integrated DNA Technologies), and a few plain oligonucleotides ordered with next-day service (Invitrogen).

Figure 1B:
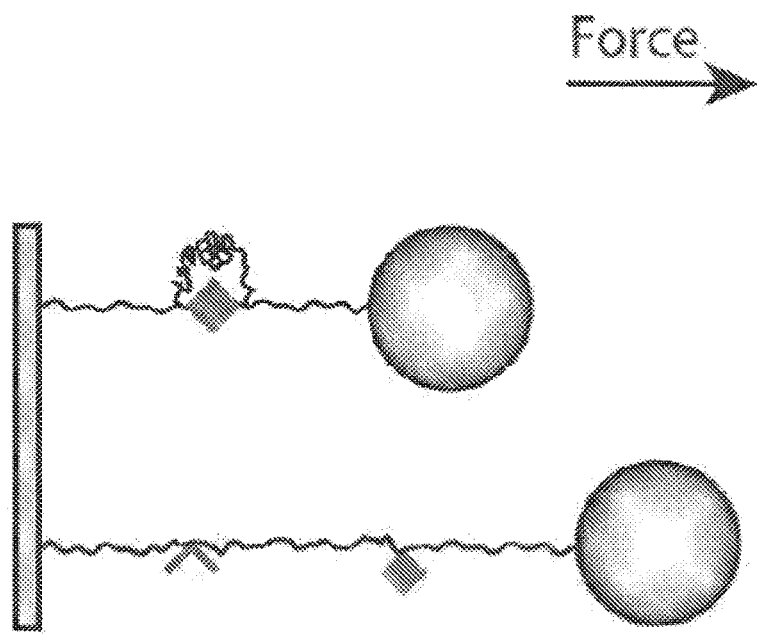
FIG. 1B. Single-molecule linking geometries: a cartoon showing receptor-ligand unbinding using a looped linker.

The full sequence of all the oligonucleotides used are shown in FIG. 1A and are based on the M13 sequence given by New England Biolabs and used for previous DNA origami work.

The oligonucleotides are stored at 100 µM at −20° C., and all mixing of oligonucleotides is done at these stock concentrations unless noted. We will refer to the numbering throughout this section as we explain the construction of the various linkers.

Two different kinds of linkers were designed and assembled based on techniques outlined from previous DNA origami work (Rothemund P. W. K. (2006); Douglas S. M. et al. (2009)). Both linkers incorporate functional 'sticky' ends (we used double biotin on both ends) which act as anchors for single-molecule experiments, as well as two functional sites near the middle of the linker to form the loop. One set of constructs forms the loop by hybridizing a single 'bridge' oligonucleotide across two distinct locations, while the other set used two separate oligonucleotides each functionalized with digoxigenin or anti-digoxigenin, which can bind to each other as a receptor-ligand pair to form the loop.

To make these linkers, M13mp18 single-stranded DNA (New England Biolabs) was first linearized by hybridizing a 40-nucleotide oligonucleotide to form a double-stranded region and then cleaving this region with BtsCI restriction enzyme (New England Biolabs). The linearized single-stranded DNA was then mixed with complimentary oligonucleotides (Bioneer, Inc.) and subjected to a temperature ramp from 90 to 20° C. with a 1° C. min$^{-1}$ ramp in a PCR machine (Bio-Rad) to allow the oligonucleotides to anneal properly. For the linker with the bridge oligonucleotide formed loop, 121 oligonucleotides excluding the bridge oligonucleotides were added in tenfold molar excess, with the bridge oligonucleotides added in equimolar concentration to the scaffold strand. For the receptor-ligand loop construct, 120 oligonucleotides excluding the antibody oligonucleotide were in tenfold molar excess, which was added in equimolar concentration and subjected to a temperature ramp from 40 to 10° C. with a 0.5° C. min$^{-1}$ ramp after the other 120 were linked.

A more detailed protocol for looped linker construction is as follows:

Step 1: Single-Stranded DNA (ssDNA) Linearization.

(1) Mix the following in a clean PCR tube: 5 µL M13mp18 ssDNA (NEB product N4040S Ð 0.25 mg/mL or 100 nM), 2.5 µL 10× buffer 4 (NEB), 0.5 µL 100 µM cut-site oligonucleotide (oligo 000A), and 16.5 µL water. (2) Briefly bring to 95° C. (30 seconds), lower to 50° C., and add 1 µL BtsCI enzyme. (3) Incubate for 1 hour at 50° C. (4) Heat deactivate the BtsCI enzyme by incubating at 95° C. for 1 minute.

To assay the linearization efficiency, add 1.21 µL of a mixture of all numbered oligonucleotides to 5 µL of linearized ssDNA and construct the double-stranded DNA (dsDNA) piece by heating to 90° C. and cooling to 20° C. at 1° C./minute or slower. The product can either be run on a 0.7% agarose gel to separate circular from linear, or the strand can be cut with a single cut enzyme (we added 1µAfeI) to make sure most or all of the ssDNA was linearized.

Step 2: Conjugating Protein to Oligo.

The protocol we used for conjugating protein to oligonucleotide was loosely based on the Pierce protocol provided with the sulfo-SMCC. (1) Deprotect the SH oligonucleotides by mixing the following in a clean PCR tube: 5 µL 0.5M TCEP (Pierce), 40 µL water, and 5 µL oligo 033A at 100 µM. Let the mixture sit for at least 30 minutes at room temperature. (2) Make 10 mM Sulfo-SMCC solution as follows: add 20 µL DMSO to 2 mg Sulfo-SMCC and pipette up and down to mix well, dilute into 450 µL of PBS, and use immediately. (3) Activate the protein as follows: suspend protein in PBS at 1 mg/ml concentration (use desalting column or centrifuge filter if necessary to concentrate or change buffer), use 20× molar excess of Sulfo-SMCC for 1 mg/ml protein (e.g., 1 mg/ml Antibody—20×: 20 µL protein @ 6.7 µM+0.27 µL Sulfo-SMCC @ 10 mM), and react for 30 minutes at room temperature. (4) Wash TCEP from oligonucleotides just before Sulfo-SMCC reaction is finished as follows: use QIAGEN® PCR clean up kit, following the protocol except eluting into 50 µL PBS for 10 µM final concentration. (5) Wash the Sulfo-SMCC from the activated protein as follows: pre-equilibrate a ZEBA™ desalt column (Pierce) with PBS, complete one or two passes of the protein through the column to eliminate Sulfo-SMCC, and re-suspend at 5 µM concentration. (6) Mix the activated protein with the de-protected oligonucleotides as follows: use 1:1 molar ratio or excess of protein (e.g. 1:1-2 µL oligonucleotide @ 10 µM+4 µL antibody @ 5 µM), and react for 30 minutes at room temperature.

Step 3: Purifying Protein Conjugated Oligo.

Once the protein has been conjugated to the oligonucleotides, it may be necessary to purify the conjugated oligonucleotide from unreacted byproducts depending on the yield of the reaction. We were typically able to get 5-50% yields, and even with a 50% yield we had trouble getting the loop to form with the digoxigenin antibody complex without purification. This is probably due to unconjugated oligonucleotides competing with the conjugated ones and due to excess protein reacting with dig-labeled oligonucleotides on the DNA construct.

To purify, the same product was run in a 4-20% polyacrylamide gel (Bio-rad) enough to separate the conjugated and unconjugated oligonucleotides (FIG. 3B), typically 150V for 40 minutes in 1× Tris/Borate/EDTA (TBE) buffer. The gel was then stained for 10-15 minutes in a 1× solution of Sybr Gold (Invitrogen) and used a razor blade to cut out the relevant band(s). Once the gel slices were cut, an electroelution kit and supplied protocol was used to extract the conjugated oligonucleotides from the gel. Briefly, the slices were placed in a midi sized electroelution tube (Gerard biotech) with 600 µL of buffer, and ran them in a horizontal electrophoresis at 150V for an additional hour. The final concentration was estimated based on the known amount of oligonucleotide put into each gel lane, the conjugation yield, and the amount of dilution in the electroelution step.

Step 4: Assembly of DNA Linkers.

Several different linkers have been made over the course of this study. All of these utilize the same basic protocol which was adapted from other DNA origami work (Rothemund P. W. K. (2006)) without further optimization. This involves mixing the oligonucleotides with the M13 ssDNA (typically in a 10× molar excess) and subjecting the mixture to a temperature ramp from 90° C. to 20° C. at 1° C./minute. This protocol may be slower than necessary, as it was based on folding complex 2D shapes rather than simply making a linear piece of dsDNA as we are doing here. A thermal cycler was used to apply the temperature ramp, but heating a water bath and letting it cool to room temperature over the same time provides the similar results.

The following mixtures of oligonucleotides were used in the construction of various linkers: (a) for plain linear, mix of all numbered oligonucleotides; (b) for linear with double biotin ends, mix of all numbered oligonucleotides except substitute 001A for 001 and 121A for 121; (c) for short loop with double biotin ends, same mixture as linear with double biotin ends, but do not include 033 or 044 (or use truncated versions of 033 and 044 to ensure all bases of M13 are paired); (d) for long loop with double biotin ends, same mixture as linear with double biotin ends, but do not include 033 or 077 (or use truncated versions of 033 and 077 to ensure all bases of M13 are paired).

To make the desired construct, mix the following in a clean PCR tube and apply the temperature ramp to anneal oligonucleotides: 5 µL of linearized ssDNA from above, 1.2 µL of one of the above mixtures (for 10:1 oligo:DNA ratio). For looped constructs, additionally add: (a) 1 µL of 1000× dilute digoxigenin oligo 044A for dig-antibody construct (b) 1 µL 1000× dilute bridge oligo 033-044B for short loop with 50 bp oligonucleotide bridge (c) 1 µL 1000× dilute bridge oligo 033-077B for long loop with 50 bp oligonucleotide bridge.

The temperature ramp completes the protocol, except for the dig-antibody construct. For the dig-antibody looped construct, add an additional 1 µL of purified antibody conjugated oligonucleotide at an approximate concentration of 100 nM once the first temperature ramp is complete. Note that if a larger volume of lower concentration oligonucleotide is used, it is important to maintain the proper buffer conditions for hybridization. Additional concentrated buffer may need to be added in this case. To anneal this oligo, we used a temperature ramp from 40° C. to 10° C. at 0.5° C./minute, though we did not exhaustively test simpler or shorter protocols. For the looped constructs, we typically got a 50% looping yield following this protocol. This looped product can be excised and purified from a gel as we did with the antibody conjugated oligo, but we did not find this purification step to be necessary for this study.

DNA Protein Conjugation:

A 3' thiol-modified oligonucleotide was reduced and linked to monoclonal and polyclonal anti-digoxigenin (Roche Applied Science) using sulfo-SMCC (Pierce) and the accompanying protocol. The NHS group on the SMCC was first linked to free amines on the antibody (at 1 mg ml-1) with a 30 min reaction at room temperature using 20-fold molar excess of SMCC in PBS at pH 7.4. At the same time, the thiol oligonucleotide was deprotected and reduced by incubating in 50 mM TCEP (Pierce) for 20 min and then cleaned using a PCR clean up kit (Qiagen). Following the first SMCC reaction, excess SMCC was removed with a Zeba desalting column (Pierce), pre-equilibrated with PBS buffer. The activated protein was then mixed with the reduced thiol oligonucleotide in a 1:1 molar ratio for 30 min at RT.

Figure 3B:
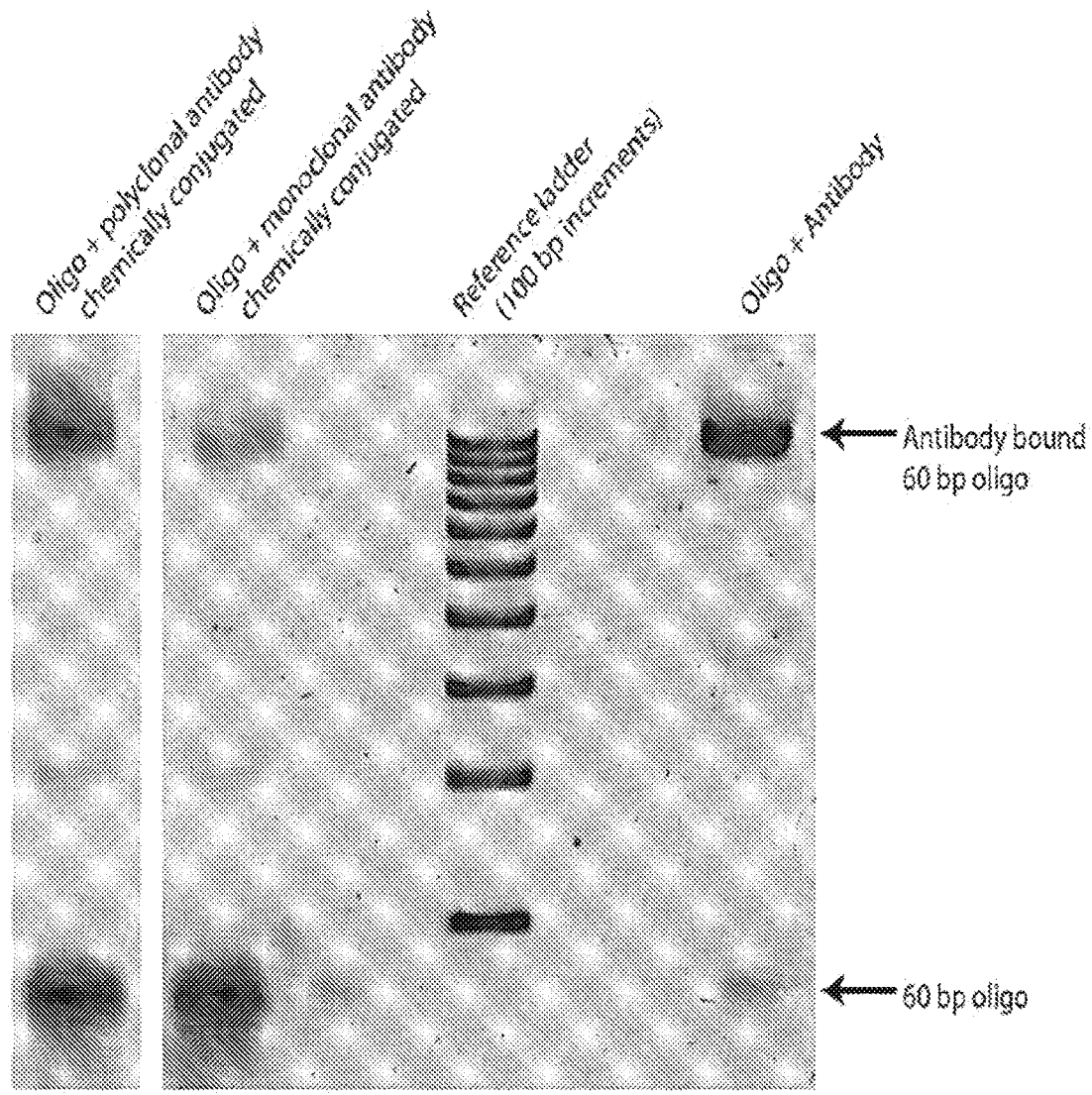
FIG. 3B. Gel verification of antibody-oligonucleotide conjugation. The left hand lanes show chemical conjugation of the oligonucleotide with polyclonal and monoclonal antibody, respectively. The right hand lane is a mixture of digoxigenin labeled oligonucleotide and anti-digoxigenin without chemical conjugation.

Conjugation was verified by visualization on a 4-20% polyacrylamide gel (Bio-Rad) run in 1×TBE buffer at 150 V for 40 min, where a shift from the protein linkage was readily apparent (see FIG. 3B). Typically, 5-50% of the oligonucleotides were conjugated to protein, and purification of the protein—DNA conjugate was accomplished by excising the gel band and using an electro-elution kit with the accompanying protocol (Gerard biotech).

Single-Molecule Force Spectroscopy:

The final unpurified linkers with double-biotin ends were incubated with streptavidin polystyrene beads (Corpuscular) for 15 min, and then injected into a chamber with PBS buffer for use in the optical trap. The optical trap setup consists of a single stationary trap and a piezo-controlled micropipette integrated into an inverted light microscope (Nikon). The setup is functionally identical to previously described instruments (Zhang X et al. (2009) Science 324: 1330; Halvorsen K. (2007) Ph.D. Thesis, Boston University, Massachusetts), but with 160× overall magnification instead of 400×. High-speed video microscopy is used to measure bead positions in 1D with a resolution of ~4 nm at ~2 kHz. The optical trap is calibrated using the blur-corrected power spectrum fit (Wong W. P. et al. (2006) Opt. Express 14: 12517-31), with additional calibration information provided by the dsDNA overstretching transition (Smith S. B. et al. (1996) Science 271: 795).

Single-molecule force measurements are performed by bringing linker functionalized beads held in the optical trap into contact with streptavidin-coated beads held in the micropipette to form molecular tethers. Tension in each tether is applied by moving the bead in the micropipette, and quantified by measuring the displacement of the bead in the optical trap. The observed distance between the beads gives a measure of the tether length.

Results and Discussion

Looped single-molecule linkers were created via DNA self-assembly. Two different kinds of linker constructs were generated and tested: (i) linkers looped by a short complementary strand of DNA to study the kinetics of DNA base pairing, and (ii) linkers looped by a receptor-ligand pair to study protein—protein interactions. As detailed below, the proper assembly and functionality of these linkers was verified using gel-shift assays and optical trap measurements. Their effectiveness for single-molecule force spectroscopy was demonstrated by measuring the kinetics of bond rupture for both DNA hybridization and an antibody-antigen interactions, and by showing how the molecular signature of a looped tether can be used to improve the accuracy of the data.

Verification of the Linker Assembly:

The linkers looped by a single DNA oligonucleotide bridge were tested first, as they served as a good model system for testing and optimizing linker assembly, independent of protein-coupling efficiency. For these oligonucleotide bridge constructs, two different loop lengths were made: 2580 base pairs and 600 base pairs. Additionally, the length of the bridge oligonucleotide on one side was varied to be 30 bp, 20 bp, 15 bp, and 10 bp, while the other side was maintained at 30 bp. The formations of both long and short loops were easily distinguishable from those of unlooped products by a gel shift due to slower migration on a 0.7% agarose gel (FIG. 3A), for both the 30 bp and 20 bp bridge constructs. Looped constructs in the gel were not observed when using the 15 bp or 10 bp bridge oligo, presumably due to the harsh conditions of electrophoresis (e.g. low salt, high temperature, high voltage). Confirmation that the shifted gel band was indeed the looped construct was accomplished by cutting the construct with a single-cut enzyme in the loop region (FIG. 3A). The shifted band (looped DNA) was largely unaffected by the enzyme, while the lower band (unlooped DNA) was completely digested into two separate pieces.

Next, these products (with double-biotin ends) were verified directly in the optical trap by pulling them end to end with linear ramps of force (FIG. 3A). Unlooped linkers show characteristic DNA force-extension behavior with typical contour lengths of 2000-2300 nm, consistent with the number of DNA bases within the construct. The looped linkers initially start with a shorter contour length, then exhibit a sudden increase to this full contour length when the DNA bridge ruptures under the application of mechanical stress. An average increase in contour length of 884 nm and 208 nm was measured for the long and short loops, respectively (FIG. 3A, inset), which is within a few nanometers of the expected length changes of 877 and 204 nm predicted from the worm-like chain polymer model using a contour length of 0.34 nm per base pair (Bustamante C. et al. (1994) Science 265: 1599-600; Bustamante C. et al. (2003) Nature 421 423-7). As can be seen in FIG. 3A, after bridge rupture both curves roughly follow the curve for the unlooped linker. As the linker was stressed above 65 pN, the DNA overstretching transition could be observed, which served as an additional mechanical signature for identifying single-molecule tethers. Pulling the molecule through this transition always resulted in detachment of the linker from the functionalized beads, presumably due to the force-induced melting of the biotinylated anchor oligonucleotides off of the ssDNA scaffold. While this effectively limits the use of this linker to measurements below about 65 pN, this could likely be overcome by covalently cross-linking the DNA linker or by using much longer anchoring oligonucleotides. Regarding the observed length of the linkers, a distribution of lengths is expected from multiple-tether measurements, even if every tether is identical on a molecular level. Because the bead in the pipette is rotationally constrained, tethers may be held at different angles, causing the measured distance between the beads to differ from the molecular tether length.

Receptor-ligand looped linkers were also created in order to measure the force-dependent kinetics of an antibody-antigen interaction. Oligonucleotides coupled to digoxigenin and to its antibody were assembled to form linkers with a loop length of 600 base pairs. The verification of these constructs was conducted in the same way as for the DNA bridge looped linkers, using both gel electrophoresis shift assays and single-molecule pulling experiments. The polyclonal looped construct was readily observed in a gel as a distinct shifted band (identical to the DNA bridge looped construct in FIG. 3A). In some instances, the monoclonal construct was not observed, likely due to the much lower affinity between digoxigenin and its monoclonal antibody and is consistent with the lack of a band for the 10 bp and 15 bp DNA bridge constructs. Both the monoclonal and polyclonal constructs were observed in the optical trap and exhibited force-extension curves that matched those of the 600 bp oligonucleotide bridge construct.

Figure 4:
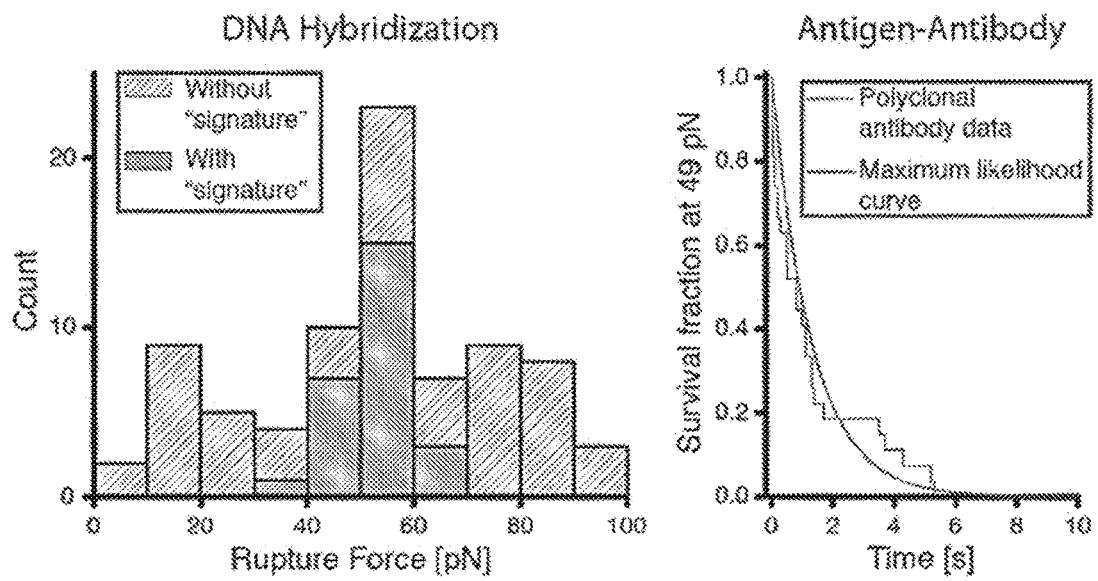
FIG. 4. Single-molecule force spectroscopy results for the rupture of (left) DNA hybridization and (right) antibody-antigen interactions. Left: rupture force histogram for shearing a 20 bp DNA segment, demonstrating the filtering of erroneous data via the looped linker molecular signature. Right: survival trajectory for digoxigenin against its antibody under constant force, with results of maximum likelihood estimation superimposed.

Demonstration of Single-Molecule Force Spectroscopy:

The dynamic strength of DNA hybridization was tested with the optical trap by repeatedly applying linear force ramps to the DNA bridge constructs to determine the distribution of the rupture force. The molecular signature of the looped linker served as a powerful filtering method to distinguish the rupture of the DNA bridge from non-specific, unknown and multiple interactions. This is illustrated in FIG. 4 (left) for the rupture force of the 20 bp bridge, where positive identification of the correct rupture transition (using the change in tether length, overall tether length, and overstretching of the linker) enabled the removal of erroneous data that accounted for 57% (34/60) of the measured events. In the resulting data, a mean rupture force of 52 pN was measured with a standard deviation of 6 pN at a nominal loading rate of 100 pN nm$^{-1}$ (this was a combination of experiments with a mean loading rate of 98 pN nm$^{-1}$ and a standard deviation of 35 pN nm$^{-1}$). This agrees within error with the expected force of 39±15 pN for the mechanical shearing of DNA (based upon their empirical formula) (Strunz T. (1999) Proc. Natl Acad. Sci. 96: 11277).

When testing the other DNA bridge lengths, fewer rupture events were observed for the 30 bp bridge, as the biotin-streptavidin bonds anchoring the linker often ruptured first. In addition, there was evidence of the 15 bp and 10 bp bridges in single-molecule pulling experiments, despite not observing these constructs with the gel-shift assay. While the formation of these loops should be energetically favorable even with the additional entropic cost of closing the loop (Hanke A. et al. (2003) Biophys. J. 85: 167-73), it is possible that the conditions of electrophoresis lower the stability of these constructs leading to their absence in the gel assays.

As another demonstration, the force-dependent unbinding kinetics of digoxigenin with its antibody was measured in the optical trap (FIG. 4 (right)). By recording repeated measurements of bond rupture under a constant force, a characteristic lifetime of 1.3 s (with a 95% confidence band of 0.9-2.0 s) at a force of 49±2 pN for the polyclonal antibody was found, using maximum likelihood estimation with an exponential decay model. This interaction was relatively strong, in agreement with other single-molecule measurements that used it as a molecular anchor (Khalil A. S. et al. (2007) Proc. Natl Acad. Sci. 104: 4892). Without the looped linker, the high bond strength of this interaction can make rupture measurements difficult, as it can be difficult to distinguish the rupture of digoxigenin-antibody from the failure of molecular anchors in the absence of an additional molecular signature.

Figure 5:
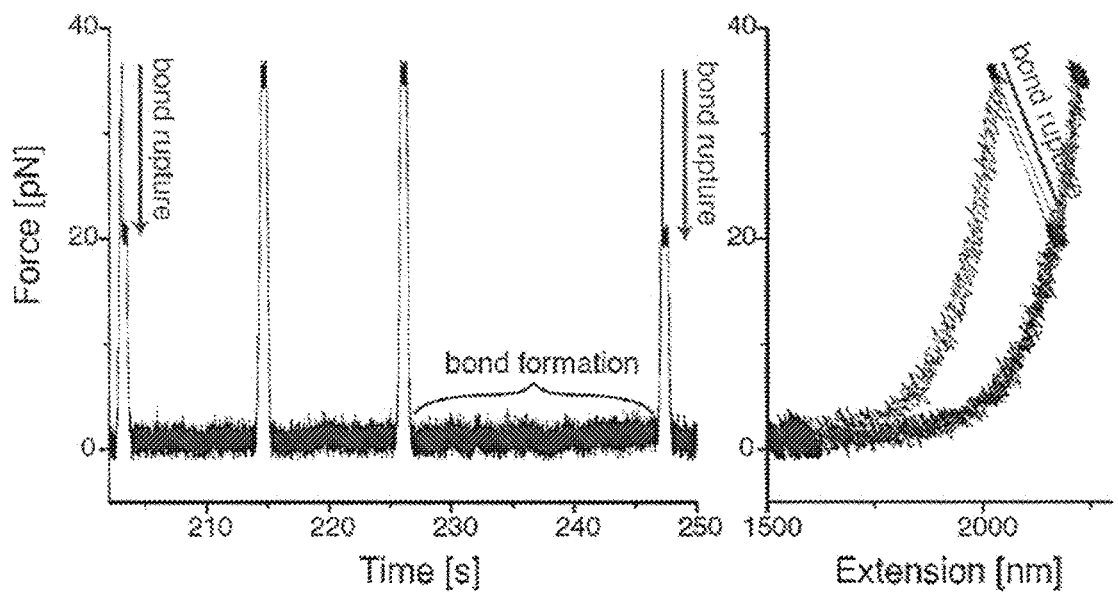
FIG. 5. Trajectory demonstrating repeated rupture and formation of a single receptor-ligand pair (digoxigenin with its monoclonal antibody): (left) force versus time and (right) force versus extension traces for repeated cycles of force application and release. Bond rupture events are observable by a sudden drop in force and an increase in tether length, as demarcated by red arrows. Rebinding/bond formation during a low force clamp can be observed by subsequent bond rupture under the application of force.

Bond rupture was measured, and single-molecule bond formation was observed. In many cases with the digoxigenin-antibody construct, the complex was reformed after dissociation by bringing the beads closer together and waiting for a short time (FIG. 5). Reformation of the oligonucleotide bridge after rupture under similar conditions was not possible, suggesting that the formation of secondary structure or the extra time to diffusively align the two strands slowed the rebinding kinetics. This may be overcome by increasing the concentration of the bridge oligonucleotide in the vicinity of the nucleic acid complex.

Conclusion

Presented herein is a simple and effective method for producing functional looped linkers using DNA self-assembly, which can increase the accuracy and reliability of single-molecule force measurements. The method is versatile enough to be useful for a wide range of molecular interactions, and simple enough to be made by researchers of diverse backgrounds without significant investment of time or money (see Appendix A). This functionality was demonstrated by constructing and testing two different looped linkers, designed for studying the dynamic strength of DNA base pairing and receptor-ligand interactions. In addition, the molecular signature provided by this 'DNA mechanical switch' enables the removal of erroneous data that can arise from non-specific, unknown, and multiple interactions. Not only is this construct useful for traditional bond rupture measurements and force spectroscopy, but it also enables the same pair of interacting molecules to be brought back together following rupture, opening the way toward high-throughput serial measurements, single-molecule on-rate studies, and studies of population heterogeneity.

Example 2. Receptor-Ligand Dissociation Kinetics Elucidated by Electrophoresis of a Binary DNA Nanoswitch Materials and Methods Linkers were designed according to protocols for long (2580 bp) and short (600 bp) loops as described herein. (See also Halvorsen K. et al. (2011) Nanotechnology, 22: 494005 incorporated herein by reference.) Here, modified oligos (Bioneer, Inc.) containing a single biotin were used such that a single streptavidin molecule could close the loop. All other oligos were the same as those used previously. Briefly, looped constructs were made by mixing a long single-stranded DNA (M13mp18, in this case) with over 121 oligos that are complementary along its length. Two oligos spaced apart from each other had biotin modifications, causing a loop to form when streptavidin binds both. The constructs come together by self-assembly with a temperature ramp heating and cooling them.

Results

Recognizing that the nanoswitch conformation informs the receptor-ligand binding state (bound or unbound), and that the conformation can be observed on a gel, an assay to measure bulk interaction kinetics was developed. The assay, conceptually shown in FIG. 7, proceeds as follows: 1) form a looped nucleic acid (DNA) construct that relies on a receptor and a ligand being bound to each other, 2) quench the interaction between the receptor and the ligand, for example, with excess receptor or ligand to prevent rebinding following dissociation, 3) monitor the relative amount of looped construct over time to measure kinetics.

To demonstrate the utility of the technique, nanoswitches were developed to measure the unbinding kinetics of the biotin-streptavidin interaction. Linear double-stranded DNA constructs 7249 base pairs (bp) in length were self-assembled by combining the single-stranded M13 bacteriophage genome with 121 complementary oligos. (See also Halvorsen K et al., 2011.). Two of the oligos were labeled with single biotins and placed 2580 bp from each other, such that interaction with streptavidin induced the formation of a 2580 bp loop in the structure. Working backwards from a predetermined experiment time, the nanoswitches were immersed in excess biotin and various experimental conditions at various times (in this case: 125, 25, 5, 1, and 0.2 hours). The entire array of 16 conditions with five time points each plus controls was then run on a single 96 lane agarose gel (FIG. 8).

To determine the biotin-streptavidin dissociation kinetics, an image of the gel was analyzed using publicly available software (ImageJ). The gel analysis tool in ImageJ was used to measure the integrated intensity of the band containing looped construct, and this quantity was normalized by the integrated intensity of a reference band in the same lane from a DNA ladder, which was added to the construct prior to starting experiments. Individual time constants for each experimental condition were determined by fitting a single exponential decay to the data using an error weighted least squares fitting.

Under the conditions tested, biotin-streptavidin time constants ranged from about half of an hour to two months (FIG. 8, upper right table). The time constants are multiplied by two to represent a single biotin-streptavidin interaction—the time constants for two bonds in series were directly measured. The interaction was highly sensitive to changing temperature and less sensitive to changing salt. At a given salt concentration, the off-rate varied over 100 fold, from 4° C. to 50° C., whereas at a given temperature, the off-rate changed by less than 2 fold from, 5 mM to 500 mM. At physiological salt concentration (150 mM), dissociation times of 148±10 hours at 25° C. and 11.2±3 hours at 37° C. were measured. The values obtained are within range of previously reported values at 25° C. and 37° C. (Chivers C. E. et al. (2010) Nature Methods 7(5): 391-393; Klumb L. A. et al. (1998) Biochemistry (Washington) 37(21): 7657-7663; Chilkoti A. et al. (1995) Journal of the American Chemical Society 117(43): 10622-10628; Jung L. S. et al. (2000) Langmuir 16(24): 9421-9432; Green N. M. (1990) Methods in Enzymology 184: 51-67).

To demonstrate the versatility of the technique, a small suite of nanoswitches was developed to measure different interactions. Antibody-antigen interaction, protein G-antibody interaction, DNA hybridization interaction, and enzymatic cleavage were demonstrated. The antibody-antigen interaction measured was digoxigenin (dig) and its polyclonal antibody. Using a dig-labeled oligonucleotide (oligo) and an anti-dig-labeled oligo, a dissociation time constant of 18.5 hours was measured. For the protein G-antibody interaction, the anti-dig labeled oligo along with a protein G-labeled oligo was used. DNA hybridization kinetics and enzymatic cleavage were both performed using a single oligo to act as the loop closure. For DNA unhybridization kinetics, an oligo with a 30 bp overlap on one side and a 20 bp overlap on the loop closure was used to measure a 20 bp hybridization off-rate. Enzymatic cleavage rates were measured using an oligo similar to that used for DNA hybridization, but with a central 20 bp insertion (and its complement) that includes the specific cleavage site for XhoI.

With these examples, it has been demonstrated that dissociation times range from minutes to weeks, across a variety of molecular systems. Measurements of more slowly dissociating molecules is possible, and is mainly limited by the patience of the experimenter and the ability to keep the molecules from degrading. Measurements of more quickly dissociating molecules is also possible, but the effect of the electrophoresis time needs to be more carefully considered. The method, as outlined, may be used for interactions with dissociation times at the gel running conditions that are comparatively slower than the gel running time. The reason for this is that the looped constructs are free to become unlooped during electrophoresis, which for these experiments, spanned 90 minutes. This effect will cause an overall reduction in the signal of the looped bands, but all gel lanes will be reduced in the same way. Thus, as long as the bands are still resolvable, there should be no major impact on the off-rate measurements. This sets a limitation on the shortest dissociation time that can be measured relative to the electrophoresis time, which would be approximately 1 hour (off-rate of $10^{-4}$).

There are a few simple ways to circumvent this limitation, one of which has been demonstrated by measuring significantly faster off-rates. For the enzymatic cleavage assay, it was possible to measure an off-rate significantly faster than $10^{-4}$ by "quenching" the cleavage with ethylenediaminetetraacetic acid (EDTA). Once the cleavage site was quenched, dissociation in the gel was not an issue. Similarly, it was possible to measure biotin-streptavidin off-rates as fast as 40 minutes at high temperature because the removal of temperature acts to effectively quench the reaction. For reactions that cannot be quenched in this way, dissociation could be chemically quenched by using a crosslinker to hold the loops closed in the gel. For example, the photoactivated DNA crosslinker trimethylpsoralen can be used to hold DNA loops together, even in cases where they normally dissociate during the gel. This strategy may be adopted to increase the range of kinetic measurements.

Conclusion

The method provided herein has at least two useful advantages: high accessibility and multiplexed measurement capability. The method is neither expensive nor difficult. It requires only minimal infrastructure and equipment (e.g., electrophoresis tools), most of which is already available in almost any biology or chemistry lab. While there is an upfront cost of making the nanoswitches (mostly from the cost of oligos), this cost is quite low on a per experiment basis. Overall, these experiments demonstrate the ability to measure molecular kinetics using a nanoengineered molecular switch along with a gel readout of the switch's state. The method provides an accurate, inexpensive, and multiplexed way to measure kinetics for a wide variety of interactions. The minimal infrastructure and equipment requirements offer a distinct advantage over established methods such as surface plasmon resonance or radioligand assays. This method will provide increased accessibility to the measurement of molecular kinetics.

REFERENCES

Kim J, Zhang C Z, Zhang X and Springer T A 2010 A mechanically stabilized receptor-ligand flex-bond important in the vasculature. Nature 466 992-5.

Wiita A P, Ainavarapu S R K, Huang H H and Fernandez J M 2006 Force-dependent chemical kinetics of disulfide bond reduction observed with single-molecule techniques Proc. Natl Acad. Sci. 103 7222-7.

Example 3. DNA Nanoswitches: A Quantitative Platform for Gel-Based Biomolecular Interaction Analysis Abstract We introduce a nanoscale experimental platform that enables kinetic and equilibrium measurements of a wide range of molecular interactions by expanding the functionality of gel electrophoresis. Programmable, self-assembled DNA nanoswitches serve both as templates for positioning molecules, and as sensitive, quantitative reporters of molecular association and dissociation. We demonstrate this low cost, versatile, "lab-on-a-molecule" system by characterizing 10 different interactions, including a complex 4-body interaction with 5 discernable states.

Materials and Methods

General Nanoswitch Formation:

The nanoswitches were constructed as previously described in detail[5]. Circular-single-stranded DNA from the 7249 nt bacteriophage M13 (New England Biolabs) was linearized by enzymatic cleavage of a single site using BtscI (New England Biolabs) and a site specific oligonucleotide. Oligonucleotides (from Bioneer or Integrated DNA Technologies (IDT)) were designed to complement the linearized M13 DNA along the backbone, resulting in 120 60-nt oligonucleotides and a single 49 nt oligonucleotide. The first and last oligonucleotide along with 10 evenly distributed oligonucleotides are intended to be interchangeable and will be referred to as variable oligonucleotides (var 1-12, with var 1 representing the first oligonucleotide and var 12 representing the last oligonucleotide). These variable oligonucleotides were stored separately from the remaining 109, referred to as backbone (bb) oligonucleotides, which were mixed in equimolar concentration in a single tube. Mixing a molar excess of the oligonucleotides (10:1 unless otherwise noted) with the ssDNA scaffold and subjecting the mixture to a temperature ramp (90° C. to 20° C. at 1° C./minute unless otherwise noted) produced double stranded DNA. Final constructs were spiked with a low concentration of DNA ladder (BstNI Digest of pBR322 DNA, New England Biolabs) to aid in quantification. For many experiments the constructs were PEG precipitated after annealing to remove excess oligonucleotides. The PEG precipitation was performed as previously described in[16].

Key Design Considerations:

The nanoswitches were designed with several key design considerations to ensure that they function properly and robustly over a wide range of conditions. The oligonucleotide length was selected to be 60 nt to ensure both site specificity, and to ensure that the oligonucleotides would not spontaneously fall off even at temperatures as high as 50° C. We show that at 50° C. even a 20-mer oligonucleotide has a long lifetime of ~18 hours (FIG. 10d), and the lifetime of a 60-mer oligonucleotide is predicted to be orders of magnitude longer than the 20-mer oligonucleotide[17].

The ligands were positioned at locations that allow for easy resolution of the looped and unlooped bands. Placement of the oligonucleotides on variable regions 4 and 5 yields two bands that are quite close to one another under our standard gel running conditions. The further apart the ligands are, the more easily resolvable the two bands become. The spacing of ligands on the DNA scaffold also controls their effective concentration, with the effective concentration of one ligand to the other generally decreasing as they are spaced further apart (though if the ligands are brought within one persistence length of the polymer, the effective concentration may decrease dramatically). We have found that the use of variable regions 4 and 8 provides a nice middle ground.

Regarding the concentrations, it is important to consider that there are three concentrations that can be independently tuned in an on-rate experiment. There is the concentration of the scaffold, the concentration of the receptor, and the effective concentration between the two ligands on the polymer. If these concentrations are adjusted carefully, many problems can be avoided. For example, if the effective concentration between the two tethered ligands is significantly higher than the concentration of the receptor, then one can minimize capping (the binding of two receptors to a single scaffold resulting in an unloopable construct). We note, however, that since our model accounts for capping, the values obtained outside this optimal regime will still be correct, the looped-band intensities will simply be weaker, resulting in a lower signal-to-noise. Although not usually a problem, one can avoid higher order aggregation by ensuring that the scaffold concentration is significantly lower than the effective concentration between the two ligands on the scaffold. One can also simplify the analysis by selecting a receptor concentration that is significantly higher than the scaffold concentration so that the receptor concentration stays effectively constant over the course of the experiment. Following these experimental design principles, in our experiments using variable oligonucleotides 4 and 8, the effective concentration between the two ligands on the loop is ~30 nM, the scaffolds are used at a concentration of 80 pM, and the receptor is used at a nominal concentration of 3 nM.

In addition to the ratio of concentrations there are some important lower and upper limits of concentration to keep in mind. We have found that working with protein concentrations below 1 nM can be unreliable due to losses of protein to the walls of the tubes. We have performed on-rate experiments with streptavidin concentrations as low as 0.3 nM but losses of protein can be as high as 80% even in protein LoBind tubes (Eppendorf technical data sheet).

Unless a means of eliminating protein loss to tubes and pipette tips is implemented, we do not recommend working below 1 nM. The upper limit is not a hard limit. We have found that the on-rate for streptavidin is very fast at 30 nM, making it difficult to pipette fast enough to take multiple time points before the plateau. If one has a means of more rapidly mixing solutions (i.e. microfluidics), or a protein with a slower on rate, higher protein concentrations can be used. We have found that 3 nM provides a nice middle ground, though one may wish to optimize the protein concentration used based on the speed of mixing, and the solution on-rate of the protein being studied.

Electrophoretic Conditions

All looped constructs were run in 0.7% agarose gels, cast from LE agarose (Seakem) or Ultrapure Agarose (Life Technologies) dissolved in 0.5× Tris-borate EDTA (TBE) (Biorad). Before loading, samples were mixed with a Ficoll-based loading solution (Promega), which we found to give sharper bands than glycerol-based loading dyes, simplifying quantification. Gels were run for 90-100 minutes at 4 V/cm, unless otherwise noted, and subsequently stained in 1× SYBRGold stain (Invitrogen) for a minimum of 30 minutes before being imaged with a gel imager (Biorad) or laser gel-scanner (GE Typhoon). It is important to note that the standard output file of this imager is often set to a .gel file which has a non-linear intensity scaling. .gel images can be linearized using the imageJ Linearize gel Data plugin available at the NIH website. Alternatively the gel image can be saved as a linear .tiff file off of the imager. We would like to point out that these expensive imagers are not required for quantification, and we obtained similar results using a blue transilluminator (Invitrogen) and a point and shoot camera (Canon S95).

Biotin-Streptavidin Nanoswitch Experiments

This construct used biotinylated versions of two oligonucleotides (var 4 and var 8), which were used in 4× molar excess to the scaffold, while all other oligonucleotides were used in a 10× molar excess. The reason for this lesser amount is twofold: 1) to be less wasteful of the more expensive functionalized oligonucleotides, and 2) because excess biotin oligonucleotide in solution could interfere with our measurements. The final DNA construct was then diluted 100× from its original concentration of ~16 nM (to 160 pM), and mixed in equal volumes with streptavidin (Rockland) at 6 nM nominal concentration to form the loops, yielding final nominal concentrations of ~80 pM and 3 nM, respectively.

On-rate experiments were performed by mixing equal volumes of 160 pM DNA construct with a nominal 6 nM streptavidin concentration, followed by taking 10 µL aliquots of the mixture at various times and mixing them with 1 µL of a saturated biotin solution to quench the formation of loops. The 25° C. experiment was performed at room temperature, the 4° C. experiment was performed in a cold room, and the 37° C. and 50° C. experiments were performed using a thermal cycler. It is important to note that for on-rate experiments, using low binding tubes (Eppendorf LoBind) was important for getting repeatable results due to significant streptavidin adsorption to the tubes when incubated at 6 nM. Actual concentrations used to determine the on-rates were measured using spectrophotometry and a HABA assay to determine streptavidin activity. We found that the actual streptavidin concentration was within 10% of the nominal concentration, and over 85% of the protein was active based on the HABA assay.

Off-rate measurements were performed by forming looped construct as described above, and letting the solution sit for at least 24 hours to allow the system to reach equilibrium. Aliquots of the looped construct were mixed at various times with a quenching solution consisting of biotin and sodium chloride to achieve the proper experimental salt concentrations, and immediately put at the experimental temperature. The 4° C. condition was done in a refrigerator, the 25° C. sample was done in a water bath, and the 37° C. and 50° C. temperatures were done in a thermal cycler. To run all the samples on a single gel, the quenching times were determined relative to the predetermined gel running time.

Preparations with avidin and neutravidin were prepared in the same way, but protein concentrations were sometimes altered to enable on-rate measurements over a similar time scale as the streptavidin experiments.

Desthiobiotin-Streptavidin

Desthiobiotin experiments were conducted in a similar manner as the biotin experiments with slight modifications. The var 4 oligonucleotide was changed to a desthiobiotin-functionalized oligonucleotide while the var 8 oligonucleotide remained biotin functionalized. The off-rate of the desthiobiotin interaction is much faster than the typical 100 minute gel run time. Noting that once a loop opens in the gel, the reptation of the DNA prevents the loop from closing again, we ran samples for different amounts of time in the gel at 15 V/cm and 4° C., and quantified the fraction looped as a function of running time. In addition to allowing the determination of the desthiobiotin-streptavidin off rate, this gel also allowed us to determine the minimum amount of time required to achieve separation of the looped and unlooped bands in the gel. This enabled the use of the standard quenching technique for measuring desthiobiotin off-rates as described in the previous section; these gels were run at 15 V/cm for 10 minutes in pre-chilled electrophoresis buffer.

DNA Hybridization Experiments

This construct used a 50 nt "bridge" oligonucleotide to span the last 30 nt of the var 4 region and the first 20 nt of the var 8 region. Thus, the normal var 4 and var 8 oligonucleotides were omitted from the mixture and replaced with 3 oligonucleotides: the aforementioned "bridge" oligonucleotide and two small "filler" oligonucleotides to fill the remaining bases so that the M13 scaffold would be fully hybridized. In this case, the bridge oligonucleotide was added in equimolar concentration with the scaffold strand, while the other oligonucleotides remained at 10× molar excess. Off-rate measurements were quenched with 500 nM 20 nt oligonucleotide corresponding to the loop closure site. Kinetics were accelerated by performing the measurement at 50° C.

Enzyme Cleavage Experiments

These constructs were made as described above, but with a bridge oligonucleotide containing an inserted sequence recognized by the XhoI enzyme (New England Biolabs). The compliment to this restriction sequence was also added to ensure that this region was double stranded. Cleavage measurements were performed by adding enzyme to the loops (with final concentrations of 2.2 nM and 1,000 units/mL for the loops and enzyme, respectively) in the recommended buffer (New England Biolabs) and quenching the enzyme activity with 75 mM EDTA at various times at room temperature.

Antibody-Antigen Experiments

This construct used a 3' digoxigenin labeled version of the var 8 oligonucleotide (Integrated DNA Technologies) and a 5' anti-dig labeled version of the var 4 oligonucleotide. The antibody labeled oligonucleotide was made by chemically crosslinking a free amine on the antibody (Polyclonal Sheep Antibody from Roche) to a thiol labeled oligonucleotide, and purified by electroelution as described previously[5]. The construct was made with two annealing steps. First, all the oligonucleotides with the exception of the antibody-labeled oligonucleotide were mixed with the scaffold strand and annealed following our standard protocol described above (except a 1:1, rather than 10:1, molar ratio was used for the digoxigenin oligonucleotide). Second, the purified antibody oligonucleotide was added in a 1:1 molar ratio and annealed from 37° C. to 4° C. at 0.5° C./minute to facilitate annealing of the antibody-modified var 4 oligonucleotide. Off-rate measurements were performed by quenching with 335 nM of antibody at various times at room temperature.

Sortase Catalyzed Peptide Ligation Experiments

This construct was created in 3 steps. 1) Var 4 and var 5 oligonucleotides with a 3' and a 5'azide respectively, were functionalized with sortase compatible peptides. 2) These two oligonucleotides were linked together with sortase. 3) The peptide-bridged oligonucleotides were hybridized onto the DNA nanoswitch. All custom peptides were purchased from NeobioLab.

1) To create the sortase-compatible oligonucleotides, sortase-compatible peptides were covalently attached using click chemistry as previously[16], the entire contents of which are incorporated by reference herein. Pra-LPETGHHHHHH, where Pra is a Propargyl glycine which adds an alkyne functionality, was coupled to var 4-azide using copper-catalyzed click chemistry. Azide-var 5 was then functionalized with a Flag-TEV-GGG-Pra peptide, where Flag denotes a Flag-tag and TEV denotes a cleavage site for the Tobaco etch virus protease. After the click chemistry the oligonucleotides were processed with a qiagen nucleotide removal kit and run on a polyacrylamide gel. The bands corresponding to the peptide-oligonucleotide chimeras were cut out and the products were extracted via electroelution as previously described.

2) Once purified the Flag-TEV-GGG-var 5 was treated with TEV (Sigma) and the two oligonucleotides were concentrated as previously[16]. These oligonucleotides were then at a concentration of ~10 uM as judged by running on a precast 4-20% gradient polyacrylamide TBE gel (BioRad). Equal volumes (10 μL each) of the sortase-compatible oligonucleotides were mixed with 5 μL of 14.1 mg/ml sortase (Chen et. al, 2011), and 25 μL of 2× Sortase Reaction buffer (600 mM Tris HCl pH 7.5, 300 mM NaCl, 10 mM MgCl$_2$, and 10 mM CaCl$_2$). This was allowed to sit for 3 hours at room temperature before running on a polyacrylamide gel and purifying the dimer band via electroelution. Yielding var 4-LPETGGG-var 5 (Note that the GGG indicates the amino acid string Gly-Gly-Gly.

3) The var 4-LPETGGG-var 5 was used instead of the normal var 4 and var 5. This was annealed onto the linear M13 backbone at a 1:1 ratio and was added along with the other oligonucleotides at the beginning of the annealing, as peptide denaturation was not a concern. This yielded loops with the peptide LPETGGG bridging variable regions 4 and 5.

With these loops in hand we could observe loop opening as a result of sortase ligating free GGG-X peptide. To accomplish this a mixture was made with the following concentrations. 2 nM DNA nanoswitches, 10 μM sortase, 40 μM GGG-S—S—CH$_3$, 300 mM Tris HCl pH 7.5, 150 mM NaCl, 5 mM CaCl$_2$, and 5 mM MgCl$_2$. Catalysis by sortase is highly calcium dependent thus the transpeptidation could be quenched at different times by adding an equal volume of 100 mM EDTA in water. 10 time points were collected over 20 minutes at room temperature.

Disulfide Reduction:

This construct was created in 3 steps. 1) Var 4 and a truncated version of var 8 with a 3' and a 5' thiol respectively, were reduced in 50 mM TCEP (BondBreaker Thermo Scientific). 2) These two oligonucleotides were linked by a disulfide. 3) The disulfide-bridged oligonucleotides were hybridized onto the DNA nanoswitch.

1) To reduce the thiols on the oligonucleotides they were incubated in 50 mM TCEP for 1 hour at RT.
2) Equal volumes of the two oligonucleotide-TCEP mixtures were then combined. The TCEP was removed using a QIAGEN nucleotide-removal kit. The oligonucleotides were then allowed to form disulfides in the absence of reducing agent in PBS for 1 hour before running the products on a precast 4-20% gradient polyacrylamide TBE gel. As the oligonucleotides were different sizes (60 and 30 nt) the appropriate hetero dimer could be easily identified and purified using electroelution as previously described[5].
3) The var 4-S-S-var 8 was used instead of the normal var 4 and var 8. This was annealed onto the linear M13 backbone at a 1:1 ratio and was added along with the other oligonucleotides at the beginning of the annealing. This yielded loops with a disulfide bridging variable regions 4 and 8.

With these loops in hand we could observe loop opening as a result of TCEP reduction of the disulfide bond. To accomplish this equal volumes of 20 μM TCEP and 160 nM loops, both of which were diluted in NEB buffer 2, were mixed at different time points before running the gel. 7 time points were collected over 10 days at room temperature before running the gel.

MultiState Loops

The bispecific receptor was formed by using a lightning link kit (Innova Biosciences) to attach streptavidin to sheep polyclonal antidig (Roche 11333089001). The antidig, suspended in PBS, was added in a 1:1 ratio to the streptavidin, and the kit protocol was followed exactly. This was then diluted 1:1250 into NEB Buffer 2 with added 150 mM NaCl before use in forming multistate loops. The multistate loop was formed by using var 4 with a 3' biotin, var 8 with a 5' digoxigenin, and var 12 with 3' digoxigenin in place of the normal var 4, 8, and 12 oligonucleotides. On-rate and off-rate measurements were performed using the same procedure used for the biotin-streptavidin experiments with slight modifications. Rather than adding streptavidin, the diluted bispecific receptor was added, samples were quenched with 2 µL of 5 µM digoxigenin-functionalized oligonucleotide (an oligonucleotide was used as digoxigenin is not water soluble) suspended in a saturated biotin solution. Gels were run 6.25 V/cm for 125 minutes with buffer chilled to 4° C. before running.

Gel Image Analysis

We analyzed gel images in one of two ways:
1) All non-multistate (only two bands) gels were analyzed in the following way:

The amount of material in each gel band was quantified by analyzing the scanned gel images with the gel analysis tool in the freely available ImageJ software package. Using rectangular regions of interest that just capture the width of the gel bands, this toolbox produces intensity profiles whose area can be measured to quantify the total brightness in each band. We applied the same rectangular window size to each lane within a single gel. In many gels the highest molecular weight band of the added ladder was used as a normalizing reference lane. This relaxed the constraints of pipetting perfectly across all lanes.

2) All multistate (with 5 bands) gels were analyzed as follows

A custom MATLAB interface was developed for fitting the intensity profiles of the imaged gel bands. The software interface was modeled after the ImageJ interface. Rectangular boxes are drawn around each lane to define a region of interest. Median filtering is a common technique used to remove speckle noise in images. Rather than filtering the entire image, each individual lane was median filtered by row to remove speckle noise without sacrificing resolution in the direction of band migration. After plotting the median-intensity profile the background was subtracted using a 4-6 point piece-wise linear function to outline the background. The background was found to be very similar across lanes and often the same background profile could be subtracted from the majority of the lanes. Once the profiles were extracted, least-squares fitting of each profile to the model was performed in MATLAB. Individual bands run on their own show a skewed Gaussian profile, also known as a skew normal distribution, with a skew parameter of ~-2.5. Thus, the entire multistate median-intensity profile (from just above the highest band to just below lowest) was fit using a sum of 5 skewed Gaussians. A common skew parameter was used for all 5 bands, and a common initial guess of band width was used with a fitting range of ±10 pixels. These input parameters allowed for converging fits across all lanes, and resulted in fits that closely matched the observed intensity profiles. The areas of the individual bands were calculated by integrating the individual skewed Gaussians. Error in the fitted areas was estimated by calculating the areas within the one-sigma confidence interval of the fit parameters. These areas were all normalized by the total area (the sum of all of the skewed Gaussian areas). The identity of the bands were validated by analyzing gels in which individual loop sizes were formed. Accuracy of band quantification was confirmed by mixing these individual loops in known ratios—the measured values of the individual bands were found to be within 10% of their true values.

Equation for a skew normal/skewed Gaussian distribution:

$$A \cdot e^{-\left(\frac{x-b}{c}\right)^2} \cdot \left(1 + \mathrm{erf}\left(a\frac{x-b}{c}\right)\right)$$

Data Analysis

Based on a gel we ran to establish repeatability of pipetting and imaging, we conservatively estimate the error per lane at ±5% plus the detection limit (which will vary by imager). For lanes that used a reference band to normalize brightness, the 5% error per band was propagated to yield roughly 7% error per measurement. Error bars were produced based on this analysis, and all fitting procedures used an error weighted least squares fit. Timed pipetting for on-rate experiments was conservatively assumed to have an error of 2 seconds, which was propagated to overall y-error by multiplying by the derivative of a preliminary fit.

Model

The time evolution of DNA nanoswitch states are modeled using multistep reaction kinetics. On rates are modeled as a two-step process:

Unbound Linear→Singly Bound Linear→Looped

Step 1 represents the binding of a free receptor in solution to a ligand on the scaffold (yielding the solution on-rate), Step 2 represents the subsequent binding of this receptor to another ligand on the same scaffold to form a loop (yielding the loop-closure rate).

Thermodynamic Analysis

The dissociation constant $K_D$ was determined by the ratio of the off- and on-rates, and the equilibrium free energy $\Delta G^0$ was determined by:

$$\Delta G^0 = -RT\ln(\tilde{K}_D)$$

Where R is the gas constant, T is the absolute temperature, and the dissociation constant, which is determined by dividing the off rate by the on rate, and is made dimensionless by dividing it by a reference concentration, i.e. $\tilde{K}_D = K_D/(1M)$. We additionally used Eyring analysis to fit the temperature dependence of the kinetic rates:

$$\ln\left(\frac{k}{T}\right) = \frac{-\Delta H}{R}\left(\frac{1}{T}\right) + \ln\left(\frac{k_B}{h}\right) + \frac{\Delta S}{R}$$

Where k is the kinetic rate constant, $k_B$ is the Boltzman constant, h is Plank's constant, and $\Delta H$ and $\Delta S$ are the enthalpy and entropy of activation, respectively.

For the salt dependence, we used the kinetic salt relationship:

$$\log(k) = \log(k_0) + 2A \cdot Z_A \cdot Z_B \sqrt{I}$$

Where k is the kinetic rate constant, $k_0$ is the rate constant without the salt, A is the Debye-Hückel constant, $Z_A$ and $Z_B$ are the charges on the two interacting species, and I is the ionic strength of the solution.

Results and Discussion

Gel electrophoresis has been a workhorse of biological research for over 50 years, providing a simple way to determine size, topology, and quantity of DNA, RNA, and protein[1,2,3]. However, quantitative kinetic and thermodynamic characterization of molecular interactions on gels remains a challenge. For example, electrophoretic mobility shift assays (EMSA) are primarily used for qualitative analysis of protein-nucleic acid interactions[4]. Quantitative biomolecular interaction analysis typically requires specialized techniques such as Surface Plasmon Resonance (SPR) (e.g. Biacore), radiolabeling, or Isothermal Titration calorimetry (ITC), with cost, required technical expertise, and material requirements sometimes posing barriers to their use. Furthermore, quantitative analysis of long-lived interactions, small molecule interactions, and multi-component complexes are difficult, even with these advanced approaches.

We introduce a new instrument-free platform, based on DNA self-assembly[5,6,7], that meets these challenges by enabling quantitative analysis of molecular interactions using standard gel electrophoresis, for pennies per sample. DNA oligonucleotides (60 nt) are functionalized with interacting molecules, and hybridized to specific locations on a single-stranded DNA scaffold (M13mp18, 7,249 nt). These DNA nanoswitches report molecular associations and dissociations through induced topological changes. Exploiting the ability to separate DNA based on topology[8], the different interaction states can be easily resolved as distinct bands on a gel (FIG. 9a).

These nanoswitches have several important features. Their programmable nature enables precise control over relative concentrations and stoichiometries on a per molecule basis. The large DNA construct causes interaction-triggered topological changes to yield distinct and repeatable gel shifts, even with the integration of large proteins[5]. Additionally, the size of the DNA allows for the incorporation of thousands of dye molecules, dramatically amplifying the signal per interaction, and making readout of the nanoswitches orders of magnitude more sensitive than most other techniques. Together, these features make this a versatile, accessible, and inexpensive tool for studying multimolecular interactions.

By monitoring changes in the nanoswitch states over time, we can determine equilibrium and kinetic rate-constants for a variety of molecular systems using standard gel electrophoresis. Loop closure over time is used to determine association rate-constants, while loop opening over time, in the presence of a competitor, is used to determine the dissociation rate-constant (FIG. 9b, 9c). These kinetic processes take place in solution and are "quenched" to halt kinetics at various time points, with the gel acting as a post-experiment readout, enabling experimental conditions that are independent of gel running conditions. Ease of readout and other nanoswitch characteristics can be optimized by tuning key design parameters, including oligonucleotide length, ligand positioning, reaction concentrations, and temperatures.

We first assessed the nanoswitch platform using the ubiquitous biotin-streptavidin system. At physiological salt conditions and 25° C., we measured a dissociation time of 9.7±0.4 days (all values are reported as the error-weighted fit parameter ±its one-sigma confidence interval), closely matching previously reported values[9]. To demonstrate parallel exploration of a broad range of experimental conditions, we measured off-rates at 16 different conditions, by measuring the fraction dissociated at 6 time points per condition, and running all 96 samples on a single gel. Each condition showed exponential decay over time, yielding 16 uniquely determined off-rates ranging from 0.8 hours to 3 months with an uncertainty typically less than 10%. Dissociation kinetics varied nearly 1,000 fold over our temperature range (4-50° C.) but only about 2 fold over our salt range (25-500 mM) (FIG. 9d). Based on these results, we present a semi-empirical model for dissociation kinetics between streptavidin and biotin-labeled oligonucleotides from 25° C. to 50° C. and 25 mM to 500 mM NaCl:

$$k_{off} \approx Te^{(42.4 - \frac{18300}{T} - 0.033\sqrt{I})}$$

Where $k_{off}$ is the value of the off-rate in $s^{-1}$, T is the value of the absolute temperature in K, and I is the value of the ionic strength of the solution in mM. This model does not describe the behavior at 4° C., presumably due to temperature dependent changes in heat capacity[10].

On-rate kinetics were measured, at a variety of temperatures, by monitoring loop formation over time. Loop closure occurs through two separate binding events, the binding of a molecule from solution to the nanoswitch, and then the closing of the loop. Thus, we fit loop closure data to a two-step kinetic model to extract these rates (FIG. 9b, 9d). At 150 mM salt we measured a room-temperature on-rate of 4.0±0.7×10$^6$ M$^{-1}$s$^{-1}$. Combining our on-rate and off-rate measurements, we calculated a dissociation constant of 2.94±0.51×10$^{-13}$M, an equilibrium free energy change, $\Delta G^0$, of −17.1±0.1 kcal/mol, and an equilibrium enthalpy change, $\Delta H$, of 26.01±0.05 kcal/mol. In general, our measurements are consistent with values reported in the literature. Specifically, we are within 15% of the reported off-rate of a biotin-labelled oligonucleotide[9], within 30% of on-rate measurements from SPR[11], and within 5% of both equilibrium $\Delta H$ measurements by ITC[12] and equilibrium $\Delta G$ measurements made by monitoring kinetics of radiolabeled biotin[13].

Without modifying the DNA construct, we were also able to measure kinetic and equilibrium properties for avidin and Neutravidin. Although Neutravidin's affinity for biotin is 20 times weaker than avidin's, they surprisingly have similar off-rates, underscoring the limitation of relying solely on affinity measurements to characterize an interaction.

To demonstrate the measurement of weaker interactions, we incorporated desthiobiotin, a biosynthetic precursor to biotin that binds streptavidin with far lower affinity[14]. By optimizing gel running conditions, we resolved the looped and unlooped constructs in as little as 6 minutes, measuring the off-rate of streptavidin-desthiobiotin as 35.3±7.5 minutes at 4° C. and 8.6±1.2 minutes at room temperature. We note that while the system is ideal for quantification of long lived interactions, even those out of the range of biacore, the time required to resolve the bands in a gel currently sets the lower limit of detectable dissociation life-times to minutes.

The modularity of the DNA construct facilitates the easy incorporation of different types of molecules. We exploited this feature to measure several biologically relevant interactions including enzymes with time constants of seconds to minutes, DNA, antibodies, small molecules, and even a covalent bond taking weeks to dissociate (FIG. 10). As with many techniques including SPR, assay preparation requires the derivatization of at least one molecule of interest. Here, we attach our molecule to a DNA oligonucleotide, which can be accomplished using a variety of techniques. In addition to SMCC-crosslinking[5], we previously described the use of click-chemistry to attach peptides to oligonucleotides, and the use of the enzyme sortase[15] (see WO2015/006626) to rapidly and efficiently attach proteins to our nano switches while preserving protein function[16].

The platform's versatility is facilitated by its universal readout—even as the molecules, temperatures, and buffer conditions for the interactions change, the "signature" gel readout does not. As an extreme example of this, we characterized the reduction of a disulfide bond at 25° C. in 10 μM TCEP yielding a time constant of 2.6±0.4 weeks (FIG. 10a). Since the signal per molecule is only dependent on the nanoswitch size, this two-atom system yields the same level of signal per interaction as a 150 kDa antibody binding to its antigen (FIG. 10c).

Additionally, the programmability of these nanoswitches enables the design of multiple topological states that are individually distinguished on a gel, facilitating the analysis of complex multicomponent interactions (FIG. 11). We engineered nanoswitches with three integrated ligands, placed strategically to form two asymmetric loops when simultaneously bound by a bi-specific receptor. The resulting nanoswitch adopts 5 resolvable states that can be identified with control experiments (FIG. 11a). We measured bi-directional transitions for all 5 states, thus determining all rate constants (FIG. 11). This ability to monitor the fraction of molecules populating each state over time would be difficult or impossible to achieve with most other measurement techniques.

This new approach expands the biomedical researcher's toolbox, enabling low-cost, accessible, and parallel multicomponent biomolecular interaction analysis using a basic laboratory technique, gel electrophoresis. We have demonstrated our platform's ability to characterize interactions with time constants ranging from seconds to months (~6 orders of magnitude), for a wide variety of molecular interactions, temperatures and buffer conditions (FIG. 9d, 10). The signals are robust and highly amplified, giving detection limits in the range of attomoles and allowing quantitative kinetic- and thermodynamic-analysis of proteins as shown here with femtomoles of material (~1 ng for a 50 kDa protein). In contrast to other techniques that provide one signal to analyze (e.g. SPR, radiolabeling, and ITC), we further differentiate our technique by showing independent measurement of 5 signals simultaneously in a unique multidimensional readout, allowing complete characterization of a complex 5-state system. The modularity and programmability of the nanoswitches affords control over the relative concentrations and stoichiometries of interacting components, independent of the nanoswitch concentration. This feature suggests that in addition to monitoring reactions, this system could be used as a template-directed synthesis technique to control complex reactions. Overall, this unique lab-on-a-molecule platform promises to be a powerful research tool, accessible to anyone able to perform gel electrophoresis.

REFERENCES

1. Thorne, H. V. Virology. 29, 234-239 (1966).
2. Bishop, D. H. L., Claybrook J. R. & Spiegelman S. J. Mol. Bio. 26, 373-387 (1967).
3. Smithies, O. Biochem J. 61, 629-641 (1955).
4. Hellman, L. M. & Fried, M. G. Nat. Prot. 2, 8 (2007).
5. Halvorsen K., Schaak D. & Wong W. P. Nanotechnology. 22, pp. 1-8 (2011).
6. Sacca, B. & Niemeyer, C. M. Angew. Chem. Int. Ed. 51, 58-66 (2012).
7. Seeman, N.C. Annual Reviews Biochemistry. 79, 65-87 (2010).
8. Aaij, C. & Borst P. BIOCHIMICA ET BIOPHYSICA ACTA. 269, 192-200 (1972).
9. Levy, M. & Ellington, A. D. Chemistry & Biology. 15, 979-989 (2008).
10. Prabhu, N. V. & Sharp, K. A. Annual Reviews Physical Chemistry. 56, 521-48 (2005).
11. Qureshi, M. H., Yeung, J. C., Wu, S. C. & Wong, S. L. J Biol Chem. 276, 46422-46428 (2001).
12. Klumb, L. A., Chu, V. & Stayton P. S. Biochemistry. 21, 7657-63 (1998).
13. Chivers, C. E. et al. Nature Methods. 7, 391-393 (2010).
14. Florin, E. L., Moy V. T., and Gaub H. E. Science. 264, 415-417 (1994).
15. Chen I., Don, B. M., and Liu D. R. Proc. Natl. Acad. Sci. USA 108, 11399-11404 (2011).
16. Koussa M. A., Sotomayor M., Wong W. P. Methods. 67 134-141 (2014).
17. Strunz T, Oroszlan K, Schafer R, & Giintherodt H J. Proc. Natl. Acad. Sci. USA 96 11277-11282 (1999).

Example 4: Analyte Detection

Abstract

We have developed a detection platform with single-digit attomole sensitivity, making it orders of magnitude more sensitive than existing techniques, while also being orders of magnitude cheaper than current detection methods. The platform's readout and per-analyte signal-intensity are independent of analyte size. This platform's sensitivity, robust nature, and affordability will allow for a complete transformation of the diagnostic landscape, as this one platform can be used to screen a wide range of analytes in labs, in the field, and even at home. We have developed a prototype that can be used to detect early pregnancy factor (EPF) which is released within hours of fertilization. As current methods for EPF detection are costly and laborious, such a diagnostic will allow for EPF detection to become a routine diagnostic both for detection of pregnancy weeks before existing methods, and for diagnosis of infertility.

Results and Discussion

Clinical diagnostics lead to actionable healthcare choices, however, their use is often limited as current clinical diagnostic assays often require expensive capital equipment investment for multiple different systems to address multiple types of tests, and some tests require large volumes (mL) of blood to be drawn. There is thus an unmet need for inexpensive, extremely sensitive platforms that can be adapted to a broad array of tests in the clinical laboratory, and subsequently adapted for point of care and over the counter applications. Here, we propose the development of an elegant low cost, extremely sensitive platform that can be used for detection of a myriad of analytes.

We have developed a technology for ultra-sensitive detection of a wide array of analytes. The system relies on the ability of a gel to separate DNA based on topology. By functionalizing a large DNA scaffold with ligands, antigens, receptors, antibodies, or nucleic acids we can translate molecular interactions into a change in the DNA's topological state. We term these two-state structures DNA nanoswitches. The two states of these nanoswitches can then be resolved via simple gel electrophoresis (FIG. 12).

This system provides several advantages over current techniques. The large DNA construct causes interaction-triggered topological changes to yield distinct and repeatable gel shifts, even with the integration of large proteins. This constant assay-agnostic readout across many assays will greatly facilitate user training and automation. Thus, one can dramatically lower the cost of POC assays as a single operator could be easily trained to perform a large array of assays. The constant readout would also make development of easy-to-use OTC tests, as a single readout device can be engineered, and different kits could be sold for assays of interest.

Additionally, the large size of the DNA allows for the incorporation of thousands of dye molecules, dramatically amplifying the signal per-interaction, and making readout of the nanoswitches orders of magnitude more sensitive than most other techniques. We have characterized the system's sensitivity showing that we can currently detect single digit attomoles (10-18 moles) of protein, and we are confident this can easily be enhanced an additional order of magnitude allowing for the detection of as few as 10,000 molecules.

We have developed a prototype pregnancy test that detects early pregnancy factor (EPF). EPF is present in the blood and cervical mucus within 8 hours of fertilization (ref. 3), meaning that it can be detected weeks before human chorionic gonadotropin (hCG), the most common indicator of pregnancy, which is not released until implantation. EPF detection is currently done in fertility clinics, but requires very large (20 ml) blood draws, culturing patient leukocytes, and determining the presence of EPF via a qualitative assay of a cell aggregation morphology which is costly and often difficult to interpret (rosette inhibition test) (refs. 4,5). This technique is often used in the bovine and equine industries as an earlier means of pregnancy testing, however this technique is laborious and requires a large amount of time, money, resources, and personnel. These issues have prevented EPF detection from becoming a routine diagnostic for human pregnancy (ref. 6).

Using a system like the one schematized in FIG. 12C, we have been able to detect EPF in a physiological buffer. This will make an ideal test case for the nanoswitch detection platform, providing a simple quantitative assay that is orders of magnitude more sensitive, and orders of magnitude more affordable than existing methods. The platform will enable the incorporation of EPF detection as a standard test both for those who want an earlier means of detecting pregnancy, and for those who are having trouble conceiving, and are trying to determine if conception is failing at fertilization or at implantation. With over 150,000 IVF patients a year, development of an affordable, highly sensitive EPF diagnostic would have a great market, and have a significant impact on the lives of these patients. Additionally, all of the technical advancements and lessons learned in developing the EPF assay will be immediately applicable in the expansion of the system to a wide reaching diagnostic platform for low-cost detection of trace analytes for clinical, food safety, homeland security, and defense purposes.

Proposed Methods and Materials

1. Develop a means to make nanoswitch closure irreversible
   a. Significance: As the nanoswitches can open while running the gel, this limits detection to analytes that have a high affinity for the nanoswitch. Making nanoswitch closure irreversible in the presence of a crosslinking agent will greatly expand the number of analytes that can be detected with the platform. Without a means of crosslinking, the system is limited to detecting things with a Kd lower than 5 nM excluding many biological analytes. The EPF loops, for example, were only observable upon glutaraldehyde-crosslinking.
   b. Timeline=6 months: We have already had some success using glutaraldehyde to crosslink proteins. However, we plan to develop a bioorthogonal crosslinking method using copper-catalyzed click chemistry with click-compatible oligonucleotides for a more controlled and universal solution.
   c. Milestones: Loops formed between streptavidin and desthiobiotin are strong enough to be separated in the gel. If, however, the gel is run longer, in an effort to attain better band resolution, all of the loops open while running in the gel. The ability to lock these loops such that the intensity of the looped band does not decrease over time would indicate that we have accomplished this aim. This would then be applied to the current EPF detection construct in lieu of glutaraldehyde crosslinking.

2. Optimize the stability and sensitivity of the nanoswitches in bodily fluids
   a. Significance: Preliminary testing indicates that the nanoswitches are not highly stable in untreated bodily fluids. In order for the platform to be useful for clinical diagnostics, the nanoswitches must be stable in fluids such as urine, saliva, serum/blood, and mucus.
   b. Timeline=6 months: Upon obtaining human samples a series of preparatory steps need to be assayed including pH buffering, removal of denaturants, and DNAse/protease inhibition. Once nanoswitch stability is achieved we will use non-pregnant (likely male) control samples that we will spike with different levels of EPF to characterize/optimize the sensitivity of the nanoswitches in various bodily fluids.

TABLE 1

| | DNA NanoSwitch | Flow cytometer (e.g., Navlos) | Immunoassay Analyzer (e.g. Bekman coulter) | Rosette Inhibition Test |
|---|---|---|---|---|
| Applications | Broad: small molecules, proteins, nucleic acids, antibodies, viruses | T, B, NK lymphocytes | Flu A + B, RSV, Group A Strep Assays | Early Pregnancy Test (2-3 days into conception for IVF applications) |
| Throughput | 10-20 min for 96-1536 samples* | 1 hour for 80 tubes (high throughput) | 10 min for 1 sample | Low (individual cell culture 1-2 day turnaround) |
| Testing/Processing location | Clinical, may be adapted for POT or OTC | Clinical lab | Clinical lab | Specialized Clinical Lab |
| Equipment cost | 100-200*** | Thousands of dollars** | Thousands of dollars*** | Thousands of dollars** |
| Necessary Training | Low (Pipetting and Gel Electrophoresis) | High (Complex instrument) | Moderate | High (Must be able to detect morphological differences of leukocytes under a microscope) |
| Cost of reagents per test | $0.01-0.05 | $50-60** | $10-15** | $20-50** |
| Detection limit | $10^{-18}$ mol (100,000 molecules)**** | Thousands of cells | ~$10^5$ CFU/ml | Not well established, due to qualitative nature of readout |

*96 samples refers to the number of lanes, this could be 96 samples from one patient or 96 different patient samples.
Additionally we have demonstrated the potential to double the number of lanes and multiplex the system to attain 8 assays per lane. This would yield 1536 simultaneous diagnostic tests.
**List price shown.
***Most labs will already own the necessary equipment for gel electrophoresis.
****Concentration independent.

c. Milestones: We have had some success with this already, but need to optimize treatment of various fluids and demonstrate the ability to detect analytes in these bodily fluids to indicate that we have achieved this aim.

3. Verify the presence of EPF in patient samples a. Significance: The first step in validating this diagnostic tool is demonstrating that the nanoswitches reproduce the results of current assays. This will be the first demonstration of the platform's ability to detect analytes such as EPF in patient samples, and will be an important step in attaining FDA approval and CLIA certification.

b. Time line=1 year: After attaining IRB approval, a large number of samples from pregnant and non-pregnant patients will be blindly screened to verify the ability of the platform to detect EPF in patient samples, these samples will also be subjected to the rosette inhibition test (RIT), and the results will be compared.

a. Milestones: The ability to match or outperform the RIT in detection EPF in samples from pregnant patients and not non-pregnant controls would indicate that we have achieved this aim.

The nanoswitch platform provides the ability to easily and reliably detect extremely low amounts of analytes, which in addition to enabling very early detection of antibodies, pathogens, secreted proteins, and DNA, will be crucial in the move towards small patient samples both for high frequency testing, and for situations such as neonatal and pediatric settings, in which large volume blood draws are simply not feasible. The modular and robust nature of the technology makes it ideal for expansion into a universal detection platform with applications in the clinical diagnostic space and beyond. This great expansion in analyte detection will provide actionable information that can greatly impact lives.

REFERENCES

1. Kalorama Information: The Worldwide Market for In Vitro Diagnostic Tests, 9th Edition
2. Mounir A. Koussa, Ken Halvorsen, Andrew Ward, and Wesley P. Wong. DNA nanoswitches: a quantitative platform for gel-based biomolecular interaction analysis. Nature Methods (in press)
3. Cheng S-J and Zheng Z-Q. Early pregnancy factor in cervical mucus of pregnant women. American Journal of Reproductive Immunology. 2004
4. Halle Morton, Hans-Rudolf Tinneberg, Barbara Rolfe, Marianne Wolf, and Lilo Mettler. Rosette inhibition test: A multicentre investigation of early pregnancy factor in humans. Journal of Reproductive Immunology (1982)
5. Halle Morton et al. Early Pregnancy Factor. Seminars in Reproductive Endocrinology (1992)
6. E. Koch and F. Ellendorff. Prospects and limitations of the rosette inhibition test to detect activity of early pregnancy factor in the pig. Journal of Reproduction and Fertility (1985)

WO 2015/006626 (PCT/US2014/046251) is incorporated by references herein in its entirety.

Halvorsen et al. Nanotechnology. 22, pp. 1-8 (2011) is incorporated by reference herein in its entirety.

Koussa et al. Methods. 67 134-141 (2014) is incorporated by reference herein in its entirety.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:
1. A method comprising
providing a single-stranded scaffold nucleic acid which is capable of hybridizing to a plurality of single-stranded oligonucleotides comprising a first single-stranded oligonucleotide, a second single-stranded oligonucleotide, and a third single-stranded oligonucleotide, wherein the first single-stranded oligonucleotide is linked to a first binding partner, the second single-stranded oligonucleotide is linked to a second binding partner, and the third single-stranded oligonucleotide is linked to a third binding partner,
forming nucleic acid complexes by incubating the single-stranded scaffold nucleic acid with the plurality of single-stranded oligonucleotides under conditions that allow for hybridization of the plurality of single-stranded oligonucleotides to the single-stranded scaffold nucleic acid and binding of the first binding partner, the second binding partner and the third binding partner to each other in the nucleic acid complexes, wherein binding of the first binding partner and the second binding partner to each other is a first molecular interaction that results in a first looped nucleic acid conformation in the nucleic acid complexes, binding of the second binding partner and the third binding partner to each other is a second molecular interaction that results in a second looped nucleic acid conformation in the nucleic acid complexes, binding of the first binding partner and the third binding partner is a third molecular interaction that results in a third looped nucleic acid conformation in the nucleic acid complexes, and binding of the first binding partner, the second binding partner and the third binding partner is a fourth molecular interaction that results in a fourth looped nucleic acid conformation in the nucleic acid complexes, wherein each of the first molecular interaction, the second molecular interaction, the third molecular interaction, and the fourth molecular interaction is an intramolecular interaction, and detecting the presence of the first nucleic acid conformation, the second nucleic acid conformation, the third nucleic acid conformation and/or the fourth looped nucleic acid conformation in the nucleic acid complexes by analyzing the nucleic acid complexes using gel electrophoresis, wherein the first nucleic acid conformation, the second nucleic acid conformation, the third nucleic acid conformation and the fourth looped nucleic acid confirmation have different migration distances on a gel after the gel electrophoresis and are distinguishable from each other based on their migration distances through the gel.

2. The method of claim 1, wherein each of the single-stranded oligonucleotides is about 60 nucleotides in length.

3. The method of claim 1, wherein least one of the first binding partner, the second binding partner, and the third binding partner is a ligand, an antigen, or a receptor.

4. The method of claim 1, wherein least one of the first binding partner, the second binding partner, and the third binding partner is a protein.

5. The method of claim 1, wherein least one of the first binding partner, the second binding partner, and the third binding partner is an antibody or an antibody fragment.

6. The method of claim 1, wherein the method further comprises measuring association and/or dissociation kinetics between (i) the first binding partner and the second binding partner, between (ii) the second binding partner and the third binding partner, between (iii) the first binding partner and the third binding partner, or among (iv) the first binding partner, the second binding partner and the third binding partner.

7. The method of claim 1, wherein the method further comprises measuring association and/or dissociation kinetics among the first binding partner, the second binding partner, and the third binding partner.

8. The method of claim 1, wherein the first molecular interaction, the second molecular interaction, the third molecular interaction, and the fourth molecular interaction comprise direct binding between the first binding partner and the second binding partner, direct binding between the second binding partner and the third binding partner, direct binding between the first binding partner and the third binding partner, and direct binding among the first binding partner, the second binding partner and the third binding partner, respectively.

9. The method of claim 1, wherein the first molecular interaction, the second molecular interaction, the third molecular interaction, and the fourth molecular interaction comprise indirect binding between the first binding partner and the second binding partner, indirect binding between the second binding partner and the third binding partner, indirect binding between the first binding partner and the third binding partner and indirect binding among the first binding partner, the second binding partner and the third binding partner, respectively.

10. The method of claim 1, wherein least one of the first binding partner, the second binding partner, and the third binding partner is a nucleic acid.

11. The method of claim 1, wherein the first binding partner, the second binding partner, or the third binding partner is a bispecific receptor.

* * * * *